United States Patent
Adolfsen et al.

(10) Patent No.: US 11,766,463 B2
(45) Date of Patent: Sep. 26, 2023

(54) MICROORGANISMS ENGINEERED TO REDUCE HYPERPHENYLALANINEMIA

(71) Applicant: SYNLOGIC OPERATING COMPANY, INC., Cambridge, MA (US)

(72) Inventors: Kristin Adolfsen, Emeryville, CA (US); Per Greisen, Seattle, WA (US); Isolde Callihan, Emeryville, CA (US); Adam Lawrence, Emeryville, CA (US); James Spoonamore, Emeryville, CA (US); Jay Konieczka, Emeryville, CA (US)

(73) Assignee: Synlogic Operating Company, Inc., Cambridge, MA (US)

( * ) Notice: Subject to any disclaimer, the term of this patent is extended or adjusted under 35 U.S.C. 154(b) by 0 days.

(21) Appl. No.: 17/832,487

(22) Filed: Jun. 3, 2022

(65) Prior Publication Data

US 2022/0362309 A1 Nov. 17, 2022

Related U.S. Application Data

(63) Continuation of application No. PCT/US2021/023003, filed on Mar. 18, 2021.

(60) Provisional application No. 63/017,755, filed on Apr. 30, 2020, provisional application No. 62/992,637, filed on Mar. 20, 2020.

(51) Int. Cl.
*A61K 35/74* (2015.01)
*A61P 3/00* (2006.01)
*A61K 9/00* (2006.01)

(52) U.S. Cl.
CPC ............ *A61K 35/74* (2013.01); *A61K 9/0053* (2013.01); *A61P 3/00* (2018.01)

(58) Field of Classification Search
None
See application file for complete search history.

(56) References Cited

U.S. PATENT DOCUMENTS

| | | | |
|---|---|---|---|
| 5,589,168 A | 12/1996 | Allen et al. | |
| 5,989,463 A | 11/1999 | Tracy et al. | |
| 6,203,797 B1 | 3/2001 | Perry | |
| 6,835,376 B1 | 12/2004 | Neeser et al. | |
| 7,731,976 B2 | 6/2010 | Cobb et al. | |
| 9,688,967 B2 | 6/2017 | Falb et al. | |
| 9,889,164 B2 | 2/2018 | Falb et al. | |
| 9,943,555 B2 | 4/2018 | Falb et al. | |
| 10,195,234 B2 | 2/2019 | Falb et al. | |
| 10,294,499 B2 | 5/2019 | Simon Vecilla et al. | |
| 10,610,546 B2 | 4/2020 | Falb et al. | |
| 10,883,115 B2 | 1/2021 | Ayal et al. | |
| 11,060,073 B2 | 7/2021 | Falb et al. | |
| 2014/0079701 A1 | 3/2014 | Miller et al. | |
| 2015/0238545 A1 | 8/2015 | Borody | |
| 2015/0246085 A1 | 9/2015 | Al-Hafid et al. | |
| 2015/0359894 A1 | 12/2015 | Weinrich et al. | |
| 2016/0068832 A1 | 3/2016 | Weiner et al. | |
| 2016/0177274 A1 | 6/2016 | Falb et al. | |
| 2017/0136073 A1 | 5/2017 | Falb et al. | |
| 2017/0216370 A1 | 8/2017 | Falb et al. | |
| 2017/0232043 A1 | 8/2017 | Falb et al. | |

FOREIGN PATENT DOCUMENTS

| | | |
|---|---|---|
| CN | 1154845 A | 7/1997 |
| CN | 101586111 A | 11/2009 |
| EP | 1666588 A1 | 6/2006 |
| EP | 1383897 A2 | 7/2011 |
| EP | 2344626 B1 | 7/2011 |
| WO | WO 2006/034373 A2 | 3/2006 |
| WO | WO 2006/079790 A2 | 8/2006 |
| WO | WO 2008/073148 A2 | 6/2008 |
| WO | WO 2009/004595 A2 | 1/2009 |
| WO | WO 2011/106874 A1 | 9/2011 |
| WO | WO 2012/078311 A1 | 6/2012 |
| WO | WO 2013/134174 A2 | 9/2013 |
| WO | WO 2013/175358 A1 | 11/2013 |
| WO | WO 2013/192543 A2 | 12/2013 |
| WO | WO 2014/018832 A1 | 1/2014 |
| WO | WO 2014/066945 A1 | 5/2014 |
| WO | WO 2014/093852 A1 | 6/2014 |
| WO | WO 2014/138324 A1 | 9/2014 |
| WO | WO 2014/172541 A2 | 10/2014 |
| WO | WO 2016/183531 A1 | 11/2016 |
| WO | WO 2016/183532 A1 | 11/2016 |
| WO | WO 2016/210373 A2 | 12/2016 |
| WO | WO 2017216704 A1 | 12/2017 |
| WO | WO 2018237198 A1 | 12/2018 |
| WO | WO 2020013951 A1 | 1/2020 |

OTHER PUBLICATIONS

Adams et al. (Jul. 15, 1990) "Nucleotide sequence and genetic characterization reveal six essential genes for the LIV-I and LS transport systems of *Escherichia coli*" *J Biol Chem*. 265(20):11436-43.

Al Hafid et al. (Jun. 2002) "Phenylketonuria: a Review of Current and Future Treatments" *Transl Pediatr*. 3:49-62.

Al Hafid et al. (Oct. 2015) "Phenylketonuria: a review of current and future treatments" *Transl Pediatr*. 4(4):304-317.

Albiniak et al. (2013) "High-level secretion of a recombinant protein to the culture medium with a Bacillus subtilis twin-arginine translocation system in *Escherichia coli*" *FEBS J*. 280:3810-3821.

Altenhoefer et al. (Apr. 9, 2004) "The probiotic *Escherichia coli* strain Nissle 1917 interferes with invasion of human intestinal epithelial cells by different enteroinvasive bacterial pathogens" *FEMS Immunol Med Microbiol*. 40(3):223-229.

Andersen et al. (Apr. 1995) "Uracil uptake in *Escherichia coli* K-12: isolation of uraA mutants and cloning of the gene" *J Bacteriol*. 177(8):2008-2013.

(Continued)

*Primary Examiner* — Brian Gangle
(74) *Attorney, Agent, or Firm* — McCarter & English, LLP; Marcie B. Clarke, Esq.

(57) ABSTRACT

Genetically engineered bacteria, pharmaceutical compositions thereof, and methods of modulating and treating diseases associated with hyperphenylalaninemia are disclosed.

8 Claims, 8 Drawing Sheets

Specification includes a Sequence Listing.

(56) References Cited

OTHER PUBLICATIONS

Anderson et al. (Apr. 1977) "*Escherichia coli* transport mutants lacking binding protein and other components of the branched-chain amino acid transport systems" *J Bacteriol.* 130(1):384-92.
Anderson et al. (Oct. 1978) "Genetic separation of high- and low-affinity transport systems for branched-chain amino acids in *Escherichia coli* K-12" *J Bacteriol.* 136(1):168-74.
Arai et al. (Aug. 28, 1995) "Expression of the nir and nor genes for denitrification of Pseudomonas aeruginosa requires a novel CRP/FNR-related transcriptional regulator, DNR, in addition to ANR" *FEBS Lett.* 371(1):73-76.
Archer et al. (2012) "Engineered *E. coli* That Detect and Respond to Gut Inflammation through Nitric Oxide Sensing" ACS Synth. Biol. 1(10): 451-457.
Argos (1989) "A possible homology between immunodeficiency virus p24 core protein and picornaviral VP2 coat protein: prediction of HIV p24 antigenic sites" *EMBO J.* 8(3):779-785.
Arrach et al. (Jun. 15, 2008) "*Salmonella* promoters preferentially activated inside tumors" *Cancer Res.* 68(12):4827-32.
Arthur et al. (Oct. 5, 2012) "Intestinal inflammation targets cancer-inducing activity of the microbiota" *Science* 338(6103):120-123. NIH Public Access Author Manuscript; available in PMC May 6, 2013 (11 pages).
Ashida et al. (2012) "Bacteria and host interactions in the gut epithelial barrier" *Nature Chem Biol.* 8: 36-45.
Baek et al. (Apr. 2011) "Expression and characterization of a second L-amino acid deaminase isolated from *Proteus mirabilis* in *Escherichia coil*" *J Basic Microbiol.* 51:129-135.
Barel et al. (Feb. 6, 2015) "The complex amino acid diet of Francisella in infected macrophages" *Front Cell Infect Microbiol.* 5:9. 5 pages.
Bearden et al. (Apr. 1999) "The Yfe system of Yersinia pestis transports iron and manganese and is required for full virulence of plague" *Mol Microbiol.* 32(2):403-14.
Becker et al. (Aug. 1996) "$0_2$ as the regulatory signal for FNR-dependent gene regulation in *Escherichia coli*" *J Bacteriol.* 178(15):4515-21.
Becker et al. (Oct. 1997) "Regulatory $0_2$ tensions for the synthesis of fermentation products in *Escherichia coli* and relation to aerobic respiration" Arch Microbiol. 168(4):290-6.
Bifulco et al. (2013) "A thermostable L-aspartate oxidase: a new tool for biotechnological applications" *Appl Microbiol Biotechnol.* 97:7285-7295.
Bikandi et al. (Mar. 22, 2004) "In Silico Analysis of Complete Bacterial Genomes: PCR, AFLP-PCR and Endonuclease Restriction" Bioinformatics 20 (5), 798-9 2004.
Blau et al. (2015) "Alternative therapies to address the unmet medical needs of patients with phenylketonuria" *Expert Opin Pharmacother.* 16(6):791-800.
Boysen et al. (Apr. 2010) "Translational Regulation of Gene Expression by an Anaerobically Induced Small Non-coding RNA in *Escherichia coli* " *J Biol Chem.* 285(14):10690-10702.
Braat et al. (2006) "A Phase I Trial With Transgenic Bacteria Expressing Interleukin-10 in Crohn's Disease" *Clinical Gastroenterology and Hepatology* 4:754-759.
Brophy et al. (2014) "Principles of Genetic Circuit Design" Nat. Methods 11(5): 508-520.
Bucarey et al. (Oct. 2005) "The *Salmonella enterica* serovar Typhi tsx gene, encoding a nucleoside-specific porin, is essential for prototrophic growth in the absence of nucleosides" *Infect Immun.* 73(10):6210-9.
Cabrita et al. (2002) "Molecular biology and regulation of nucleoside and nucleobase transporter proteins in eukaryotes and prokaryotes" *Biochem Cell Biol.* 80(5):623-38.
Caldara et al. (Oct. 19, 2007) "ArgR-dependent repression of arginine and histidine transport genes in *Escherichia coli*" K-12. J Mol Biol. 373(2):251-67.

Callura et al. (Sep. 7, 2010) "Tracking, tuning, and terminating microbial physiology using synthetic riboregulators" *Proc Natl Acad Sci USA*, 107(36):15898-15903.
Castiglione et al. (Sep. 2009) "The transcription factor DNR from *Pseudomonas aeruginosa* specifically requires nitric oxide and haem for the activation of a target promoter in *Escherichia coli*" *Microbiology*, 155(Pt 9):2838-2844.
Celis (Jun. 1977) "Properties of an *Escherichia coli* K-12 mutant defective in the transport of arginine and ornithine" *J Bacteriol.* 130(3):1234-43.
Cellier et al. (Jun. 1996) "Resistance to intracellular infections: comparative genomic analysis of Nramp" *Trends Genet.* 12(6):201-4.
Chang (2007) "Use of Enzyme Artificial Cells for Genetic Enzyme Defects" In *Artificial Cells: Biotechnology, Nanomedicine, Regenerative Medicine, Blood Substitutes, Bioencapsulation, and Cell/Stem Cell Therapy. Regenerative Medicine, Artificial Cells and Nanomedicine*—vol. 1. Singapore: World Scientific Publishing pp. 147-159.
Charbonneau et al. (Apr. 8, 2020) "Developing a new class of engineered live bacterial therapeutics to treat human diseases" *Nat Commun* 11, 1738 (2020). https://doi.org/10.1038/s41467-020-15508-1.
Chen et al. (Mar. 2006) "High-level Expression of Phenylalanine Ammonia-lyase in *Lactococcus lactis* via Synthesized Sequence Based on Bias Codons" *Chin J Biotech.* 22(2):187-190.
Christodoulou et al. (Nov. 2012) "Enzyme substitution therapy for phenylketonuria delivered orally using a genetically modified probiotic: Proof of principle" $62^{nd}$ Annual Meeting of the American Society of Human Genetics, Nov. 6-10, 2012, San Francisco, CA; Program No. 166, Nov. 8, 2012.
Chye et al. (Jan. 1987) Transcription control of the aroP gene in *Escherichia coli* K-12: analysis of operator mutants. *J Bacteriol.* 169(1):386-93.
Clarkson et al. (1971) "Diaminopimelic Acid and Lysine Auxotrophs of *Pseudomonas aeruginosa* 8602" *J Gen Microbiol.* 66:161-169.
Coban et al. (2014) "Screening of phenylpyruvic acid producers and optimization of culture conditions in bench scale bioreactors" Bioprocess Biosyst Eng. 37:2343-2352.
Collinson et al. (2015) "Channel crossing: how are proteins shipped across the bacterial plasma membrane?" *Philos Trans R Soc B* 370:20150025 [online]. Retrieve from: http://rstb.royalsocietypublishing.org/, on Jun. 16, 2016 (13 pages).
Communication Pursuant to Article 94(3) EPC issued in European Patent Application No. 16728448.8 dated Dec. 20, 2018.
Cosgriff et al. (2000) A Study of AroP-PheP Chimeric Proteins and Identification of a Residue Involved in Tryptophan Transport J. Bacteriol. 182(8): 2207-2217.
Costa et al. (May 2015) "Secretion systems in Gram-negative bacteria: structural and mechanistic insights" *Nat Rev Microbiol.* 13(6):343-359.
Cuevas-Ramos et al. (Jun. 22, 2010) "*Escherichia coli* induces DNA damage in vivo and triggers genomic instability in mammalian cells" *Proc Natl Acad Sci USA*, 107(25):11537-11542.
Danino et al. (May 2015) "Programmable probiotics for detection of cancer in urine" *Sci Transl Med.* 7(289):289ra84 [online]. Retrieved from: www.sciencetranslationalmedicine.org, on Jul. 30, 2015 (11 pages).
Den Hengst et al. (May 2006) "Identification and functional characterization of the Lactococcus lactis CodY-regulated branched-chain amino acid permease BcaP (CtrA)" *J Bacteriol.* 188(9):3280-9.
Deutscher (Apr. 2008) "The mechanisms of carbon catabolite repression in bacteria" *Curr Opin Microbiol.* 11(2):87-93.
Dinleyici et al. (Nov. 2014) "*Saccharomyces boulardii* CNCM i-745 in different clinical conditions" *Expert Opin Biol Ther.* 14(11):1593-1609.
Dobbelaere et al. (2003) "Evaluation of nutritional status and pathophysiology of growth retardation in patients with phenylketonuria" *J Inherit Metab Dis*, 26(1):1-11.
Drouault et al. (Jun. 2002) Oral Treatment with *Lactococcus Lactis* Expressing *Syaphylococcus hyicus* Lipase Enhances lipid Digestion in Pigs with Induced Pancreatic Insufficienty *Applied and Envoronmental Microbiology*, pp. 3166-3168.

(56) References Cited

OTHER PUBLICATIONS

Duan et al. (2008) "Secretion of Insulinotropic Proteins by Commensal Bacteria: Rewiring the Gut To Treat Diabetes" *Appl. Environ. Microbial.* pp. 7437-7438.
Duarte et al. (Feb. 2010) "PerR vs OhrR: selective peroxide sensing in *Bacillus subtilis*" *Mol Biosyst.* 6(2):316-23.
Dubbs et al. (Oct. 2012) "Peroxide-sensing transcriptional regulators in bacteria" *J Bacteriol.* 194(20):5495-503.
Duerre et al. (Feb. 1975) "L-Amino Acid Oxidases of *Proteus rettgeri*" *J Bacteriol.* 121(2):656-663.
Dunn et al. (Jul. 1, 2010) "The alternative oxidase (AOX) gene in Vibrio fischeri is controlled by NsrR and upregulated in response to nitric oxide" *Mol Microbiol.* 77(1):44-55.
Durand et al. (Mar. 2010) "Reprogramming of Anaerobic Metabolism by the FnrS Small RNA" *Mol Microbiol.* 75(5):1215-1231. NIH Public Access Author Manuscript; available in PMC Sep. 17, 2010 (28 pages).
Durrer et al. (May 2017) "Genetically engineered probiotic for the treatment of phenylketonuria (PKU); assessment of a novel treatment in vitro and in the PAHenu2 mouse model of PKU" *Plos One*, 12(5): e0176286.
Eiglmeier et al. (Jul. 1989) "Molecular genetic analysis of FNR-dependent promoters" *Mol Microbiol.* 3(7):869-878.
Elkins et al. (Dec. 2001) "Genes encoding bile salt hydrolases and conjugated bile salt transporters in Lactobacillus johnsonii 100-100 and other *Lactobacillus* species" *Microbiology* 147(Pt 12):3403-12.
Estrem et al. (Aug. 1998) "Identification of an UP element consensus sequence for bacterial promoters" *Proc Natl Acad Sci USA*, 95(17):9761-9766.
Folling (1994) "The Discovery of Phenylketonuria" *Act Paediatr Suppl* 407:4-10.
Forbes (Nov. 2010) "Engineering the perfect (bacterial) cancer therapy" *Nat Rev Cancer* 10(11 ):785-94.
Galimand et al. (Mar. 1991) "Positive FNR-like control of anaerobic arginine degradation and nitrate respiration in *Pseudomonas aeruginosa*" *J Bacteriol.* 173(5):1598-1606.
Gardner et al. (2000) "Construction of a genetic toggle switch in *Escherichia coli*" *Nature*, 403:339-342.
GENBANK Database Accession No. AAA86752 (Feb. 3, 1996) "amino acid deaminase [Proteus mirabilis HI4320" [online]. National Center for Biotechnology Information (NCBI), U.S. National Library of Medicine; http://www.ncbi.nlm.nih.gov/protein/AAA86752 (1 page).
GENBANK Database Accession No. AAH26251.1 (Jul. 15, 2006) "Phenylalanine hydroxylase [*Homo sapiens*]" [online]. National Center for Biotechnology Information (NCBI), U.S. National Library of Medicine; http://www.ncbi.nlm.nih.gov/protein/AAH26251 (2 pages).
GENBANK Database Accession No. ABA23593.1 (Jan. 28, 2014) "histidine ammonia-lyase [Anabaena variabilis ATCC 29413]" [online]. National Center for Biotechnology Information (NCBI), U.S. National Library of Medicine; http://www.ncbi.nlm.nih.gov/protein/ABA23593 (2 pages).
GENBANK Database Accession No. ACD36582.1 (Aug. 15, 2011) "L-amino acid deaminase [Proteus mirabilis]" [online]. National Center for Biotechnology Information (NCBI), U.S. National Library of Medicine; http://www.ncbi.nlm.nih.gov/protein/ACD36582 (1 page).
GENBANK Database Accession No. BAA90864.1 (Feb. 18, 2000) "L-amino acid deaminase [Proteus vulgaris]" [online]. National Center for Biotechnology Information (NCBI), U.S. National Library of Medicine; http://www.ncbi.nlm.nih.gov/protein/BAA90864 (1 page).
GENBANK Database Accession No. CAE15566.1 (Feb. 27, 2015) "Histidine ammonia-lyase (histidase) [*Photorhabdus luminescens* subsp. laumondii TTO1]" [online]. National Center for Biotechnology Information (NCBI), U.S. National Library of Medicine; http://www.ncbi.nlm.nih.gov/protein/CAE15566 (2 pages).
GENBANK Database Accession No. EDV65095.1 (Jun. 20, 2008) "arromatic amino acid transport protein AroP [*Escherichia coli* F11]" [online]. National Center for Biotechnology Information (NCBI), U.S. National Library of Medicine; http://www.ncbi.nlm.nih.gov/protein/EDV65095 (2 pages).
GENBANK Database Accession No. EU669819.1 (Aug. 15, 2011) "Proteus mirabilis L-amino acid deaminase gene, complete cds" [online]. National Center for Biotechnology Information (NCBI), U.S. National Library of Medicine; http://www.ncbi.nlm.nih.gov/nuccore/EU669819 (2 pages).
GENBANK Database Accession No. U35383.1 (Feb. 3, 1996) "Proteus mirabilis amino acid deaminase (aad) gene, complete cds" [online]. National Center for Biotechnology Information (NCBI), U.S. National Library of Medicine; http://www.ncbi.nlm.nih.gov/nuccore/U35383 (2 pages).
Gerdes et al. (Oct. 2006) "Essential genes on metabolic maps" *Curr Opin Biotechnol.* 17(5):448-456.
Gilbert et al. (Jan. 1985) "Molecular cloning of the phenylalanine ammonia lyase gene from *Rhodosporidium toruloides* in *Escherichia coli* K-12" *J Bacteriol.* 161(1):314-320.
Görke et al. (Aug. 2008) "Carbon catabolite repression in bacteria: many ways to make the most out of nutrients" *Nat Rev Microbiol*, 6(8):613-624.
Gouzy et al. (Feb. 20, 2014) "*Mycobacterium tuberculosis* exploits asparagine to assimilate nitrogen and resist acid stress during infection" *PLoS Pathog.* 10{2}:e1003928. 14 pages.
Grothe et al. (Apr. 1986) "Proline transport and osmotic stress response in *Escherichia coli* K-12" *J Bacteriol.* 166(1):253-9.
Guardiola et al. (Feb. 1974) "Mutations affecting the different transport systems for isoleucine, leucine, and valine in *Escherichia coli* K-12" *J Bacteriol.* 117(2):393-405.
Guardiola et al., (Dec. 1971) "*Escherichia coli* K-12 mutants altered in the transport of branched-chain amino acids" *J Bacteriol.* 108{3}:1034-44.
Guarner et al. (Feb. 8, 2003) "Gut flora in health and disease" *Lancet* 361 (9356):512-9.
Haney et al. (Jan. 1992) "Lrp, a leucine-responsive protein, regulates branched-chain amino acid transport genes in *Escherichia coli*" *J Bacteriol.* 174(1):108-15.
Hasegawa et al. (Sep. 15, 1998) "Activation of a consensus FNR-dependent promoter by DNR of *Pseudomonas aeruginosa* in response to nitrite" *FEMS Microbiol Lett.* 166(2):213-217.
He et al. (Apr. 13, 1999) "Noninvasive measurement of anatomic structure and intraluminal oxygenation in the gastrointestinal tract of living mice with spatial and spectral EPR imaging" *Proc Natl Acad Sci USA*, 96(8):4586-4591.
Heatwole et al. (Jun. 1991) The tryptophan-specific permease gene, mtr, is differentially regulated by the tryptophan and tyrosine repressors in *Escherichia coli* K-12 *J Bacteriol.* 173(11):3601-4.
Higgins (1992) "ABC transporters: from microorganisms to man" *Annu Rev Cell Biol.* 8:67-113.
Ho et al. (2014) "Phenylkentonuria: translating research into novel therapies" *Transl Pediatr.* 3:49-62.
Hoeks et al. (Jan. 2009) "Adult issues in phenylketonuria" *Neth J Med.* 67(1):2-7.
Hoeren et al. (Nov. 15, 1993) "Sequence and expression of the gene encoding the respiratory nitrous-oxide reductase from *Paracoccus denitrificans*" *Eur J Biochem.* 218(1):49-57.
Horsburgh et al. (Jun. 2002) "MntR modulates expression of the PerR regulon and superoxide resistance in *Staphylococcus aureus* through control of manganese uptake" *Mol Microbiol.* 44(5):1269-86.
Horsburgh et al. (May 2004) "PheP, a putative amino acid permease of *Staphylococcus aureus*, contributes to survival in vivo and during starvation" *Infect Immun.* 72(5):3073-6.
Hosseini et al. (May 2011) "Propionate as a health-promoting microbial metabolite in the human gut" *Nutr Rev.* 69(5):245-258.
Hou et al. (Oct. 2015) "Production of phenylpyruvic acid from L-phenylalanine using an L-amino acid deaminase from *Proteus mirabilis*: comparison of enzymatic and whole-cell biotransformation approaches" *Appl Microbiol Biotechnol.* 99(20):8391-8402.
Hu et al. (Nov. 15, 1998) "Membrane topology of the *Escherichia coli* gamma-aminobutyrate transporter: implications on the topography and mechanism of prokaryotic and eukaryotic transporters from the APC superfamily" *Biochem J.* 336 (Pt 1):69-76.

(56) References Cited

OTHER PUBLICATIONS

Huibregtse et al (2012) "Genetically Modified *Lactococcus lactis* for Delivery of Human Interleukin-10 to Dendritic Cells" *Gastroenterology Research and Practice*, vol. 2012, Article ID 639291 (7 pages).
International Patent Application No. PCT/US2016/032562, filed May 13, 2016, by Synlogic, Inc.: International Search Report and Written Opinion; dated Aug. 22, 2016.
International Patent Application No. PCT/US2016/032565, filed May 13, 2016, by Synlogic, Inc.: International Search Report and Written Opinion; dated Aug. 5, 2016.
International Patent Application No. PCT/US2016/062369, filed Nov. 16, 2016, by Synlogic, Inc.: International Search Report and Written Opinion; dated Mar. 10, 2017.
International Patent Application No. PCT/US2018/038840, filed Jun. 21, 2018, by Synlogic Operating Company, Inc. International Search Report and Written Opinion; dated Nov. 21, 2018.
Isabella et al. (Jan. 2009) "Functional analysis of NsrR, a nitric oxide-sensing Rrf2 repressor in Neisseria gonorrhoeae" *Mol Microbiol.* 71(1):227-39.
Isabella et al. (Jan. 20, 2011) "Deep sequencing-based analysis of the anaerobic stimulon in *Neisseria gonorrhoeae*" *BMC Genomics*, 12:51 (24 pages).
Isabella et al. (Oct. 2011) "Identification of a conserved protein involved in anaerobic unsaturated fatty acid synthesis in Neiserria gonorrhoeae: implications for facultative and obligate anaerobes that lack FabA" *Mol Microbiol.* 82(2):489-501.
Isabella et al, (2018) "Development of a synthetic live bacterial therapeutic for the human metabolic disease phenylketonuria", Nature Biotechnology,vol. 36, No. 9, 01, p. 857-864.
Ivanovska et al. (2014) "Pediatric Drug Formulations: A Review of Challenges and Progress" *Pediatrics*, 134:361-372.
Jack et al. (Aug. 2000) "The amino acid/polyamine/organocation (APC) superfamily of transporters specific for amino acids, polyamines and organocations" *Microbiology* 146 (Pt 8):1797-814.
Jennings et al. (Jan. 1995) "Cloning and molecular analysis of the *Salmonella enterica* ansP gene, encoding an L-asparagine permease" *Microbiology* 141 (Pt 1):141-6.
Jensen et al. (2015) "Manganese Transport, Trafficking and Function in Invertebrates" Issues in Toxicology No. 22, Manganese in Health and Disease. Lucio G. Costa (Ed.). The Royal Society of Chemistry. Chapter 1, pp. 1-33(2015).
Jia, X. et al. (2000) "A new strategeutics of gene therapy for hyperphenylalaninemia rats" *National Medical Journal of China*, 2000 Issue 06, English Abstract. [online]. Retrieved from: http://en.cnki.com.cn/Article_en/CJFDTOTAL-ZHYX200006029.htm, on Jan. 30, 2017 (3 pages).
Jia, X. et al. (2000) "A new strategeutics of gene therapy for hyperphenylalaninemia rats" *National Medical Journal of China*, 2000 Issue 06. English translation, Phoenix Translations, Elgin, TX: Nov. 2015 (15 pages).
Jolkver et al. (Feb. 2009) "Identification and characterization of a bacterial transport system for the uptake of pyruvate,propionate, and acetate in Corynebacterium glutamicum" *J Bacteriol.* 191(3):940-8.
Kadaba et al. (Jul. 11, 2008) "The high-affinity *E. coli* methionine ABC transporter: structure and allosteric regulation" *Science.* 321(5886):250-3.
Kadner et al. (Aug. 1974) "Methionine transport in *Escherichia coli*: physiological and genetic evidence for two uptake systems" *J Bacteriol.* 119(2):401-9.
Kang et al. (2010) "Converting an injectable protein therapeutic into an oral form: Phenylalanine ammonia lyase for phenylketonuria" *Mol Genet Metabol.* 99:4-9.
Kehres et al. (Jun. 2002) "SilABCD Is the Alkaline Mn2+ Transporter of *Salmonella enterica* Serovar Typhimurium" *Journal of Bacteriology* 184(12):3159-3166.
Kobe et al. (Jun. 1997) "Regulation and crystallization of phosphorylated and dephosphorylated forms of truncated dimeric phenylalanine hydroxylase" *Protein Sci.* 6(6):1352-1357.

Koo et al. (Jun. 2, 2003) "A reducing system of the superoxide sensor SoxR in *Escherichia coli*" *EMBO J* 22(11):2614-22.
Kyndt et al., Characterization of a bacterial tyrosine ammonia lyase, a biosynthetic enzyme for the photoactive yellow protein, FEBS Letters 512 (2002) 240-244.
Kwok et al. (Jan. 29, 1985) "Nucleotide sequence of a full-length complementary DNA clone and amino acid sequence of human phenylalanine hydroxylase" *Biochemistry*, 24(3):556-561.
Landick et al., (Jul. 15, 1985) "The complete nucleotide sequences of the *Escherichia coli* LIV-BP and LS-BP genes. Implications for the mechanism of high-affinity branched-chain amino acid transport" *J Biol Chem.* 260(14):8257-61.
Lee et al. (2011) "Cumulative Number of Cell Divisions as a Meaningful Timescale for Adaptive Laboratory Evolution of *Escherichia coli*" *PLoS One*, 6:e26172, http://dx.doi.org/10.1371/journal.pone.0026172 (8 pages).
Lee et al. (May 17, 2012) "Systems metabolic engineering of microorganisms for natural and non-natural chemicals" *Nat Chem Biol.* 8(6):536-46.
Leonard, "Disorders of the urea cycle and related enzymes" in *Inborn Metabolic Diseases*, 4th ed. Heidelberg: Springer Medizin Verlag, 2006; pp. 263-272.
Levanon et al. (2005) "Effect of oxygen on the *Escherichia coli* ArcA and FNR regulation systems and metabolic responses" *Biotech. Bioeng.* pp. 556-564.
Li et al. (Apr. 13, 2001) "Monomeric state and ligand binding of recombinant GABA transporter from *Escherichia coli*" *FEBS Lett.* 494(3):165-9.
Liu et al. (2002) "Study on a Novel Strategy to Treatment of Phenylketonuria" *Art Cells, Blood Subs, and Immob Biotech.* 30(4):243-257.
Longo et al. (Jul. 5, 2014) "Phase 1 Trial of Subcutaneous rAvPAL-PEG in Subjects with Phenylketonuria" *Lancet*, 384(9937):37-44. HHS Public Access Author Manuscript; available in PMC Jul. 5, 2015 (18 pages).
Lopez et al. (Dec. 2015) "Synthetic Auxotrophs with Ligand-Dependent Essential Genes for a BL21(DE3) Biosafety Strain" *ACS Synthetic Biology*, 4(12):1279-1286.
Ma et al. (2014) Oral Administration of Recombinant Lastococcus Lactis Expressing HSP65 and Tandemly Repeated P277 Reduces the Incidence of Type 1 Diabetes in Non-Obese Diabetic Mice PLoS One 9:105701.
MacDonald et al. (2007) "A modern view of phenylalanine ammonia lyase" *Biochem Cell Biol.* 85(3):273-282.
MacLeod et al. (Jun. 2010) "Nutritional Management of Phenylketonuria" *Ann Nestle Eng.* 68(2):58-69.
Marbach et al. (2012) "lac operon Indcution in *Escherichia Coli*: Systematic Comparison of IPTG and TMG induction and influence of Transacetylase LacA" *Journal of Biotechnology*, 157:82-88.
Matano et al. (Jun. 2014) "Engineering of Corynebacterium glutamicum for growth and L-lysine and lycopene production from N-acetylglucosamine" *Appl Microbiol Biotechnol.* 98(12):5633-43.
McAllister et al. (Aug. 2004) "Molecular analysis of the psa permease complex of *Streptococcus pneumoniae*" *Mol Microbiol.* 53(3):889-901.
McEwen et al. (Mar. 2013) "Engineering Synechococcus elongatus PCC 7942 for continuous growth under diurnal conditions" *Appl Environ Microbiol.* 79(5):1668-75.
Meadow et al. (1959) "Biosynthesis of diaminopimelic acid and lysine in *Escherichia coli*" *Biochem J.* 72(3):396-400.
Mengesha, A. et al. (2006) "Development of a flexible and potent hypoxia-inducible promoter for tumor-targeted gene expression in attenuated *salmonella*" *Cancer Biology & Therapy*, 5:9, 1120-1128.
Menzel et al. (Sep. 25, 1981) "Purification of the putA gene product. A bifunctional membrane-bound protein from *Salmonella typhimurium* responsible for the two-step oxidation of proline to glutamate" *J Biol Chem.* 256(18):9755-61.
Merlin et al. (Oct. 2002) "The *Escherichia coli* metD locus encodes an ABC transporter which includes Abe (MetN), YaeE (MetI), and YaeC (MetQ)" *J Bacteriol.* 184(19):5513-7.
Mironov et al. (Jul. 15, 1999) "Computer analysis of transcription regulatory patterns in completely sequenced bacterial genomes" *Nucleic Acids Res.* 27(14):2981-9.

(56) References Cited

OTHER PUBLICATIONS

Moffitt et al. (Jan. 30, 2007) "Discovery of two cyanobacterial phenylalanine ammonia lyases: kinetic and structural characterization" *Biochemistry*, 46(4):1004-1012.

Moore et al. (Nov. 3, 2006) "Regulation of FNR dimerization by subunit charge repulsion" *J Biol Chem.* 281(44):33268-33275.

Nazos et al. (Sep. 1985) "Identification of livG, a membrane-associated component of the branched-chain amino acid transport in *Escherichia coli*" *J Bacteriol.* 163(3):1196-202.

Nazos et al. (May 1986) Cloning and characterization of livH, the structural gene encoding a component of the leucine transport system in *Escherichia coli. J. Bacteriol.* 166(2):565-73.

Nji et al. (Oct. 2014) Cloning, expression, purification, crystallization and preliminary X-ray diffraction of a lysine-specific permease from Pseudomonas aeruginosa *Acta Crystallogr F Struct Biol Commun.* 70(Pt 10):1362-7.

Norholm et al. (Aug. 2001) "Specificity and topology of the *Escherichia coli* xanthosine permease, a representative of the NHS subfamily of the major facilitator superfamily" *J Bacteriol.* 183(16):4900-4.

Nougayrede et al. (Aug. 11, 2006) "*Escherichia coli* induces DNA double-strand breaks in eukaryotic cells" *Science*, 313(5788):848-851.

Ogawa et al. (Dec. 1997) "Isolation and characterization of an *Escherichia coli* mutant lacking the major serine transporter, and cloning of a serine transporter gene" *J Biochem.* 122(6):1241-5.

Ogawa et al. (Dec. 1998) "Cloning and expression of the gene for the Na+-coupled serine transporter from *Escherichia coli* and characteristics of the transporter" *J Bacteriol.* 180(24):6749-52.

Oh et al. (Oct. 21, 1994) "Structural basis for multiple ligand specificity of the periplasmic lysine-, arginine-, ornithine-binding protein" *J Biol Chem.* 269(42):26323-30.

Ohnishi et al. (Aug. 1988) "Cloning and nucleotide sequence of the brnQ gene, the structural gene for a membrane-associated component of the LIV-II transport system for branched-chain amino acids in *Salmonella typhimurium*" *Jpn J Genet.* 63(4 ):343-57.

Olier et al. (Nov.-Dec. 2012) "Genotoxicity of *Escherichia coli* Nissle 1917 strain cannot be dissociated from its probiotic activity" *Gut Microbes*, 3(6):501-509.

Ortuno-Olea et al. (Aug. 15, 2000) "The L-asparagine operon of Rhizobium elli contains a gene encoding an atypical asparaginase" *FEMS Microbiol Lett.* 189(2):177-82.

Ostrovsky De Spicer et al. (May 1, 1993) "PulA protein, a membrane-associated flavin dehydrogenase, acts as a redox-:lependent transcriptional regulator" *Proc Natl Acad Sci USA.* 90(9):4295-8.

Oxender et al. (Mar. 1980) "Structural and functional analysis of cloned DNA containing genes responsible for branched-chain amino acid transport in *Escherichia coli*" *Proc Natl Acad Sci US A.* 77(3):1412-6.

Pascalle et al. (1996) "Controlled Gene Expression Systems for Lactococcus lactis with the Food-Grade Inducer Nisin" Applied and Environmental Microbiology p. 3662-3667.

Pelmont et al. (1972) "L-aminoacide oxydases des enveloppes de *Proteus mirabilis*: propriétés générales (L-amino acid oxidases of *Proteus mirabilis*: general properties)" *Biochimie* 54(10):1359-1374 (French; English summary on p. 1359).

Pi et al. (Jun. 1991) "Cloning and sequencing of the pheP gene, which encodes the phenylalanine-specific transport system of *Escherichia coil*" *J Bacteriol.* 173(12):3622-3629.

Pi et al. (May 1996) "Topology of the phenylalanine-specific permease of *Escherichia coli*" *J Bacteriol.* 178(9):2650-2655.

Pi et al. (Nov. 1998) "Functional consequences of changing proline residues in the phenylalanine-specific permease of *Escherichia coli*" *J Bacteriol.* 180(21):5515-5519.

Porcheron et al. (Dec. 5, 2013) "Iron, copper, zinc, and manganese transport and regulation in pathogenic Enterobacteria: correlations between strains, site of infection and the relative importance of the different metal transport systems for virulence" *Front Cell infect Microbiol.* 3:90.

Pugsley (Mar. 1993) "The complete general secretory pathway in gram-negative bacteria" *Microbiol Rev.* 57(1):50-108.

Purcell et al. (2013) "Towards a whole-cell modeling approach for synthetic biology" *Chaos*, 23(2):025112 (8 pages).

Quay et al. (Mar. 1977) "Role of transport systems in amino acid metabolism: leucine toxicity and the branched-chain amino acid transport systems" *J Bacteriol.* 129(3):1257-65.

Que et al. (Mar. 2000)"Manganese homeostasis in Bacillus subtilis is regulated by MntR, a bifunctional regulator related to the diphtheria toxin repressor family of proteins" *Mol Microbiol.* 35(6):1454-68.

Rahmanian et al. (Dec. 1973) "Multiplicity of leucine transport systems in *Escherichia coli* K-12" *J Bacteriol.* 116(3):1258-66.

Ray et al. (Nov. 15, 1997) "The effects of mutation of the anr gene on the aerobic respiratory chain of *Pseudomonas aeruginosa*" *FEMS Microbiol Lett.* 156(2):227-232.

Rees et al. (Mar. 2009) "ABC transporters: The power to change" *Nat Rev Mol Cell Biol.* 10(3):218-227.

Reeves et al. (Apr. 2015) "Engineering *E. coli* into a protein delivery system for mammalian cells" *ACS Synth Biol.* Just Accepted Manuscript, DOI: 10.1021/acssynbio.5b00002 [online]. Retrieved from: http://pubs.acs.org, on Apr. 20, 2015 (26 pages). Final publication in vol. 5, pp. 644-654.

REFSEQ Database Accession No. NP_415108.1 (Dec. 16, 2014) "phenylalanine transporter [*Escherichia coli* str. K-12 substr. MG1655]" [online]. National Center for Biotechnology Information (NCBI), U.S. National Library of Medicine; http://www.ncbi.nlm.nih.gov/protein/NP_415108 (3 pages).

REFSEQ Database Accession No. WP_011146484.1 (May 24, 2013) "histidine ammonia-lyase [Photorhabdus luminescens]" [online]. National Center for Biotechnology Information (NCBI), U.S. National Library of Medicine; http://www.ncbi.nlm.nih.gov/protein/WP_011146484 (1 page).

Reister et al. (Oct. 10, 2014) "Complete genome sequence of the Gram-negative probiotic *Escherichia coli* strain Nissle 1917" *J Biotechnol.* 187:106-107.

Rembacken et al. (Aug. 21, 1999) "Non-pathogenic *Escherichia coli* versus mesalazine for the treatment of ulcerative colitis: a randomised trial" *Lancet*, 354(9179):635-639.

Rigel et al. (2008) "A new twist on an old pathway—accessory secretion systems" *Mol Microbiol.* 69(2):291-302.

Rodionov et al. (Dec. 1, 2003) "Regulation of lysine biosynthesis and transport genes in bacteria: yet another RNA riboswitch?" *Nucleic Acids Res.* 31(23):6748-57.

Roquet et al. (2014 ) "Digital and analog gene circuits for biotechnology" Biotechnol. J 9(5): 597-608.

Rosen (Jun. 10, 1971) "Basic amino acid transport in *Escherichia coli*" *J Biol Chem.* 246(11 ):3653-62.

Ryan et al. (May 2007) "The uncoupled chloride conductance of a bacterial glutamate transporter homolog" *Nat Struct Mol Biol.* 14(5):365-71.

Ryan et al. (Mar. 2009) "Bacterial delivery of a novel cytolysin to hypoxic areas of solid tumors" *Gene Ther.* 16(3):329-39.

Saier Jr. (2006) "Protein Secretion and Membrane Insertion Systems in Gram-Negative Bacteria" *J Membrane Biol.* 214:75-90.

Saier Jr., M.H. (2006) "Protein Secretion Systems in Gram-Negative Bacteria. Gram-negative bacteria possess many protein secretion-membrane insertion systems that apparently evolved independently" *Microbe*, 1(9):414-419.

Salmon et al. (Aug. 8, 2003) "Global gene expression profiling in *Escherichia coli* K12. The effects of oxygen availability and FNR" *J Biol Chem.* 278(32):29837-29855.

Sarkissian et al. (Mar. 1999) "A different approach to treatment of phenylketonuria: Phenylalanine degradation with recombinant phenylalanine ammonia lyase" *Proc Natl Acad Sci USA*, 96(5):2339-2344.

Sarkissian et al. (Jun. 2007) "Quantitation of phenylalanine and its trans-cinnamic, benzoic and hippuric acid metabolites in biological fluids in a single GC-MS analysis" *J Mass Spectrom.* 42(6):811-817.

Sarkissian et al. (Nov. 2011) "Evaluation of orally administered PEGylated phenylalanine ammonia lyase in mice for the treatment

(56) References Cited

OTHER PUBLICATIONS of Phenylketonuria" *Mol Genet Metab.* 104(3): 249-254. NIH Public Access Author Manuscript; available in PMC Nov. 1, 2012 (15 pages).
Sat et al. (Mar. 2003) "The *Escherichia coli* mazEF suicide module mediates thymineless death" *J Bacteriol.* 185(6):1803-1807.
Sawers (Jun. 1991) "Identification and molecular characterization of a transcriptional regulator from *Pseudomonas aeruginosa* PAO1 exhibiting structural and functional similarity to the FNR protein of *Escherichia coli*" *Mol Microbiol*, 5(6):1469-1481.
Schultz (Jul. 2008) "Clinical use of *E. coli* Nissle 1917 in inflammatory bowel disease" *Inflamm Bowel Dis*, 14(7):1012-1018.
Seep-Feldhaus et al. (Dec. 1991) "Molecular analysis of the Corynebacterium glutamicum lysI gene involved in lysine uptake" Mol Microbiol. 5(12):2995-3005.
Shao et al. (Jun. 15, 1994) "Sequencing and characterization of the sdaC gene and identification of the sdaCB operon in *Escherichia coli* K12" *Eur J Biochem.* 222(3):901-7.
Sheehan et al.(Mar. 2006) "Heterologous expression of BetL, a belaine uptake system, enhances the stress tolerance of lactobacillus salivarius UCC118" *Appl Environ Microbiol.* 72(3):2170-7.
Silhavy et al. (2010) "The bacterial cell envelope" *Cold Spring Harb Perspect Biol. 2*, a000414 (17 pages).
Siuti et al. (2014) "Engineering genetic circuits that compute and remember" Nat Protoc 9, 1292-1300.
Sleator et al. (2009) "Rational Design of Improved Pharmabiotics" *Journal of Biomedicine and Biotechnology*, vol. 9 (7pages).
Slotboom et al. (Jun. 1999) "Structural features of the glutamate transporter family" *Microbiol Mol Biol Rev.* 63(2):293-307.
Sonnenborn et al. (2009) "The non-pathogenic *Escherichia coli* strain Nissle 1917—features of a versatile probiotic" *Microbial Ecology in Health and Disease*, 21:122-158.
Stanley et al. (Oct. 2003) "Acute infection and macrophage subversion by *Mycobacterium tuberculosis* require a specialized secretion system" *PNAS*, 100(22):13001-13006.
Steele (Jun. 1986) "Blood-brain barrier transport of the alpha-keto acid analogs of amino acids" *Fed Proc.* 45(7):2060-2064.
Steffes et al. (May 1992) "The lysP gene encodes the lysine-specific permease" *J Bacteriol.* 174(10):3242-9.
Steidler et al. (Jul. 1, 2003) "Biological containment of genetically modified Lactococcus lactis for intestinal delivery of human interleukin 10" *Nature Biotechnology*, 21(7)785-789.
Strauch et al (Feb. 1985) "Oxygen Regulation in *Salmonella typhimurium*" *J. Bacteriol.* 161(2):673-680.
Sun et al. (2005) "Genomic peculiarity of coding sequences and metabolic potential of probiotic *Escherichia coli* strain Nissle 1917 inferred from raw genome data" *J Biotechnol.* 117(2):147-61.
Takahashi et al. (Sep. 2015) "Multiple Functions of Glutamate Uptake via Meningococcal GltT-GltM L-Glutamate ABC Transporter in Neisseria meningitidis Internalization into Human Brain Microvascular Endothelial Cells" Infect Immun. 83(9):3555-67.
Tolner et al. (Oct. 1992) "Characterization and functional expression in *Escherichia coli* of the sodium/proton/glutamate symport proteins of Bacillus stearothermophilus and Bacillus caldotenax" *Mol Microbiol.* 6(19):2845-56.
Trip et al. (Jan. 2013;) "Cloning, expression, and functional characterization of secondary amino acid transporters of Lactococcus lactis" *J Bacteriol.* 195(2):340-50.
Trotschel et al. (Jun. 2005) "Characterization of methionine export in Corynebacterium glutamicum" *J Bacteriol.* 187 (11):3786-94.
Trunk et al. (Jun. 2010) "Anaerobic adaptation in *Pseudomonas aeruginosa*: definition of the Anr and Dnr regulons" *Environ Microbiol.* 12(6):1719-1733.
U.S. Appl. No. 62/183,935, filed Jun. 24, 2015, by Kotula et al.
U.S. Appl. No. 62/184,811, filed Jun. 25, 2015, by Falb et al.
U.S. Appl. No. 62/263,329, filed Dec. 4, 2015, by Kotula et al.
Ukena et al. (Dec. 12, 2007) "Probiotic *Escherichia coli* Nissle 1917 inhibits leaky gut by enhancing mucosal integrity" *PLoS One*, 2(12):e1308. [online] DOI: 10.1371/journal.pone.0001308 (11 pages).

Unden et al. (2002) "Control of FNR Function of *Escherichia coli* by $O_2$ and Reducing Conditions" *J. Mol. Microbiol. Biotechnol.* 4(3):263-268.
Unden et al. (Jul. 4, 1997) "Alternative respiratory pathways of *Escherichia coli*: energetics and transcriptional regulation in response to electron acceptors" *Biochim Biophys Acta*, 1320(3):217-234.
UNIPROTKB/SWISS-PROT Database Accession No. Q3M5Z3.1 (Nov. 11, 2015) "RecName: Full=Phenylalanine ammonia-lyase" National Center for Biotechnology Information (NCBI), U.S. National Library of Medicine, http://www.ncbi.nlm.nih.gov/protein/Q3M5Z3 (7 pages).
Van Der Meer et al. (2010) "Where microbiology meets microengineering: design and applications of reporter bacteria" Nat Rev Microbiol, 8(7): 511-522.
Vaziri et al. (Mar. 2013) Use of molecular modelling to probe the mechanism of the nucleoside transporter NupG*Mol Membr Biol.* 30(2):114-28.
Vockley et al. (Feb. 2014) "Phenylalanine hydroxylase deficiency: diagnosis and management guideline" *Genet/Med.* 16(2):188-200.
Wanner et al. (Jan. 1995) "The phenylalanine ammonia-lyase gene family in *Arabidopsis thaliana*" *Plant Mol Biol.* 27(2):327-338.
Weisser et al. (Jun. 1995) "Functional expression of the glucose transporter of Zymomonas mobilis leads to restoration of glucose and fructose uptake in *Escherichia coli* mutants and provides evidence for its facilitator action" *J Bacteriol.* 177(11):3351-4.
Widhalm et al. "Identification of a Plastidial Phenylalanine Exporter the Influences Flux Distribution Through the Phenylalanine Biosynthetic Network" *Nature Comomunications* pp. 1-11.
Williams et al. (Aug. 2005) "The gene stlA encodes a phenylalanine ammonia-lyase that is involved in the production of a stilbene antibiotic in *Photorhabdus luminescens* TT01" *Microbiology*, 151 (Pt 8):2543-2550.
Willis et al. (Sep. 1975) "L-asparagine uptake in *Escherichia coli*" *J Bacteriol.* 123(3):937-45.
Winteler et al. (Mar. 1996) "The homologous regulators ANR of *Pseudomonas aeruginosa* and FNR of *Escherichia coli* have overlapping but distinct specificities for anaerobically inducible promoters" *Microbiology*, 142(Pt 3):685-693.
Wissenbach et al. (Jun. 1993) "Physical map location of the new artPIQMJ genes of *Escherichia coli*, encoding a periplasmic arginine transport system" J Bacteriol. 175(11):3687-8.
Wissenbach et al. (Aug. 1995) "A third periplasmic transport system for L-arginine in *Escherichia coli*: molecular characterization of the artPIQMJ genes, arginine binding and transport" *Mol Microbiol.* 17(4):675-86.
Wolken et al. (Mar. 2006) "The mechanism of the tyrosine transporter TyrP supports a proton motive tyrosine decarboxylation pathway in Lactobacillus brevis" *J Bacteriol.* 188(6):2198-206.
Wood (Jun. 25, 1975) "Leucine transport in *Escherichia coli*. The resolution of multiple transport systems and their coupling to metabolic energy" *J Biol Chem.* 250(12):4477-85.
Wright et al. (Mar. 20, 2015) "GeneGuard: A modular plasmid system designed for biosafety" *ACS Synth Biol.* 4(3):307-316.
Wu et al. (Oct. 7, 2015) "Direct regulation of the natural competence regulator gene tfoX by cyclic AMP (cAMP) and cAMP receptor protein in Vibrios" *Sci Rep.* 5:14921 (15 pages).
Xiang et al. (Jun. 2005) "Biochemical characterization of a prokaryotic phenylalanine ammonia lyase" *J Bacteriol.* 187(12):4286-4289.
Xingyuan et al. (1999) "A New Strategeutics of Gene Therapy for Hyperphenylalaninemia Rats" Beijing Red-Cross Chaoyang Hospital, Capital University of Medical Sciences Beijing, 100020: China.
Yamato et al. (Apr. 1979) "Genetic and biochemical studies of transport systems for branched-chain amino acids in *Escherichia coli*" *J Bacteriol.* 138(1):24-32.
Yamato et al. (Oct. 1980) "Genetic and biochemical studies of transport systems for branched-chain amino acids in *Escherichia coli* K-12: isolation and properties of mutants defective in leucine-repressible transport activities" *J Bacteriol.* 144(1):36-44.
Yanofsky et al. (Oct. 1991) "Physiological studies of tryptophan transport and tryptophanase operon induction in *Escherichia coli*" *J Bacteriol..* 173(19):6009-17.

(56) References Cited

OTHER PUBLICATIONS

Zaprasis et al. (Jan. 2015) "Uptake of amino acids and their metabolic conversion into the compatible solute proline confers osmoprotection to Bacillus subtilis" *Appl Environ Microbiol.* 81(1):250-9.

Zhang et al. (2009) "DEG 5.0, a database of essential genes in both prokaryotes and eukaryotes" *Nucl Acids Res.* 37(suppl. 1):D455-D458.

Zhou et al. (Apr. 1999) "*Salmonella typhimurium* encodes a putative iron transport system within the centisome 63 pathogenicity island" *Infect Immun.* 67(4):1974-81.

Song, Jie et al., 'Molecular cloning, expression and characterization of a phenylalanine ammonia-lyase gene (SmPAL1) from Salvia miltiorrhiza', Molecular Biology Reports. 2009, vol. 36, pp. 939-952, DOI: 10.1007/s11033-008-9266-8.

| PAL Variant | $V_{max}$ (μmol TCA/min) | $K_m$ (mM Phe) | Correlation |
|---|---|---|---|
| Wild Type | 3.19 | 1.67 | 0.96 |
| mPAL1 | 11.95 | 4.03 | 0.983 |
| mPAL2 | 10.7 | 4.39 | 0.974 |
| mPAL3 | 11.46 | 3.72 | 0.981 |

FIG. 3B

MICROORGANISMS ENGINEERED TO REDUCE HYPERPHENYLALANINEMIA

The present application is a continuation of PCT/US2021/023003, filed Mar. 18, 2021, which claims the benefit of priority to U.S. Provisional Patent Application No. 62/992,637, filed on Mar. 20, 2020, and U.S. Provisional Patent Application No. 63/017,755, filed on Apr. 30, 2020, the contents of which are incorporated by reference in their entireties.

SEQUENCE LISTING

The instant application contains a Sequence Listing which has been submitted electronically in ASCII format and is hereby incorporated by reference in its entirety. Said ASCII copy, created on Jul. 25, 2022, is named 12671_0022-00304_SL.txt and is 50,850 bytes in size. The Sequence Listing created on Mar. 28, 2021, which is 50,812 bytes in size, is hereby removed.

This disclosure relates to compositions and therapeutic methods for reducing hyperphenylalaninemia. In certain aspects, the disclosure relates to genetically engineered microorganisms, e.g., bacteria, that are capable of reducing hyperphenylalaninemia in a mammal. In certain aspects, the compositions and methods disclosed herein may be used for treating diseases associated with hyperphenylalaninemia, e.g., phenylketonuria.

Phenylalanine is an essential amino acid primarily found in dietary protein. Typically, a small amount is utilized for protein synthesis, and the remainder is hydroxylated to tyrosine in an enzymatic pathway that requires phenylalanine hydroxylase (PAH) and the cofactor tetrahydrobiopterin. Hyperphenylalaninemia is a group of diseases associated with excess levels of phenylalanine, which can be toxic and cause brain damage. Primary hyperphenylalaninemia is caused by deficiencies in PAH activity that result from mutations in the PAH gene and/or a block in cofactor metabolism.

Phenylketonuria (PKU) is a severe form of hyperphenylalaninemia caused by mutations in the PAH gene. PKU is an autosomal recessive genetic disease that ranks as the most common inborn error of metabolism worldwide (1 in 3,000 births) and affects approximately 13,000 patients in the United States. More than 400 different PAH gene mutations have been identified (Hoeks et al., 2009). A buildup of phenylalanine (phe) in the blood can cause profound damage to the central nervous system in children and adults. If untreated in newborns, PKU can cause irreversible brain damage. Treatment for PKU currently involves complete exclusion of phenylalanine from the diet. Most natural sources of protein contain phenylalanine which is an essential amino acid and necessary for growth. In patients with PKU, this means that they rely on medical foods and phe-free protein supplements together with amino acid supplements to provide just enough phenylalanine for growth. This diet is difficult for patients and has an impact on quality of life.

As discussed, current PKU therapies require substantially modified diets consisting of protein restriction. Treatment from birth generally reduces brain damage and mental retardation (Hoeks et al., 2009; Sarkissian et al., 1999). However, the protein-restricted diet must be carefully monitored, and essential amino acids as well as vitamins must be supplemented in the diet. Furthermore, access to low protein foods is a challenge as they are more costly than their higher protein, nonmodified counterparts (Vockley et al., 2014).

In children with PKU, growth retardation is common on a low-phenylalanine diet (Dobbelaere et al., 2003). In adulthood, new problems such as osteoporosis, maternal PKU, and vitamin deficiencies may occur (Hoeks et al., 2009). Excess levels of phenylalanine in the blood, which can freely penetrate the blood-brain barrier, can also lead to neurological impairment, behavioral problems (e.g., irritability, fatigue), and/or physical symptoms (e.g., convulsions, skin rashes, musty body odor). International guidelines recommend lifelong dietary phenylalanine restriction, which is widely regarded as difficult and unrealistic (Sarkissian et al., 1999), and "continued efforts are needed to overcome the biggest challenge to living with PKU— lifelong adherence to the low-phe diet" (Macleod et al., 2010).

In a subset of patients with residual PAH activity, oral administration of the cofactor tetrahydrobiopterin (also referred to as THB, BH4, Kuvan, or sapropterin) may be used together with dietary restriction to lower blood phenylalanine levels. However, cofactor therapy is costly and only suitable for mild forms of phenylketonuria. The annual cost of Kuvan, for example, may be as much as $57,000 per patient. Additionally, the side effects of Kuvan can include gastritis and severe allergic reactions (e.g., wheezing, lightheadedness, nausea, flushing of the skin).

The enzyme phenylalanine ammonia lyase (PAL) is capable of metabolizing phenylalanine to non-toxic levels of ammonia and transcinnamic acid. Unlike PAH, PAL does not require THB cofactor activity in order to metabolize phenylalanine. Studies of oral enzyme therapy using PAL have been conducted, but "human and even the animal studies were not continued because PAL was not available in sufficient amounts at reasonable cost" (Sarkissian et al., 1999). A pegylated form of recombinant PAL (PEG-PAL) is also in development as an injectable form of treatment. However, most subjects dosed with PEG-PAL have suffered from injection site reactions and/or developed antibodies to this therapeutic enzyme (Longo et al., 2014). Thus, there is significant unmet need for effective, reliable, and/or long-term treatment for diseases associated with hyperphenylalaninemia, including PKU. There is an unmet need for a treatment that will control blood Phe levels in patients while allowing consumption of more natural protein.

In some embodiments, the disclosure provides mutant PAL polypeptides and polynucleotides. In some embodiments, the mutant PAL exhibits increased stability and/or increased ability to metabolize phenylalanine and/or reduce hyperphenylalaninemia compared to a wild type PAL, e.g., *P. luminescens* PAL. In some embodiments, the mutant PAL polypeptide comprises one or more mutations at amino acid positions 92, 133, 167, 432, 470, 433, 263, 366 and/or 396 compared to a wild type PAL, e.g., *P. luminescens* PAL. In some embodiments, the mutant PAL polypeptide comprises one or more mutations at amino acid positions S92, H133, I167, L432, V470, A433, A263, K366, and/or L396 compared to a wild type PAL, e.g., *P. luminescens* PAL.

In some embodiments, the disclosure provides genetically engineered microorganisms, e.g., bacteria, that produce the mutant PAL. In some embodiments, the engineered microorganisms further comprise a gene encoding a phenylalanine transporter, e.g., PheP. In some embodiments, the engineered microorganisms may also comprise a gene encoding L-amino acid deaminase (LAAD). The engineered microorganisms may also contain one or more gene sequences relating to biosafety and/or biocontainment. The expression of any these gene sequence(s) in a gene expression system may be regulated using a suitable promoter or promoter system.

In certain embodiments, the genetically engineered microorganisms are non-pathogenic and may be introduced into the gut in order to reduce toxic levels of phenylalanine. The disclosure also provides pharmaceutical compositions comprising the genetically engineered microorganisms, and methods of modulating and treating disorders associated with hyperphenylalaninemia. In some embodiments, the genetically engineered bacterium comprising the mutant PAL comprises one or more phage genome(s), wherein one or more of the phage genomes are defective, e.g., such that lytic phage is not produced.

BRIEF DESCRIPTION OF THE FIGURES

FIGS. 3A-B depict Michaelis-Menten graphs of wild type PAL3, mPAL1, mPAL2, and mPAL3.

DETAILED DESCRIPTION

Figure 1:
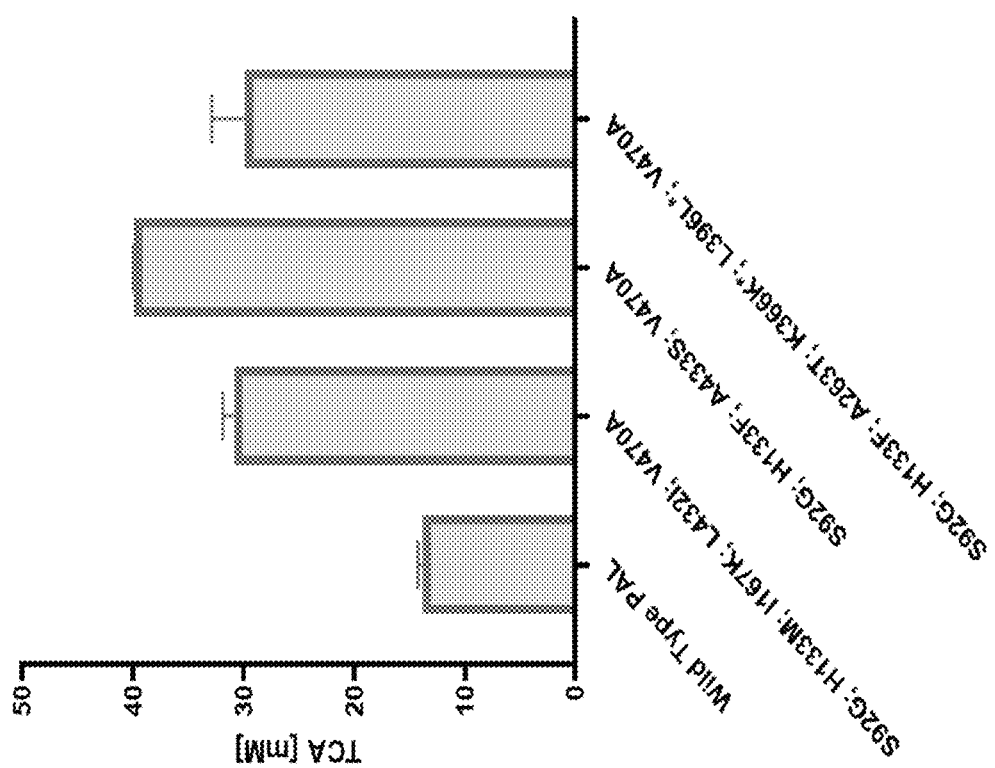
FIG. 1 depicts phenylalanine metabolism by mPAL1, mPAL2 and mPAL3 as measured by TCA.

The present disclosure includes, inter alia, mutant PAL polypeptides and polynucleotides. In some embodiments, the mutant PAL exhibits increased stability and/or increased ability to metabolize phenylalanine and/or reduce hyperphenylalaninemia compared to a wild type PAL, e.g., *P. luminescens* PAL. The present disclosure also includes genetically engineered microorganisms comprising the mutant PAL, pharmaceutical compositions thereof, and methods of modulating and treating disorders associated with hyperphenylalaninemia, e.g., PKU.

In order that the disclosure may be more readily understood, certain terms are first defined. These definitions should be read in light of the remainder of the disclosure and as understood by a person of ordinary skill in the art. Unless defined otherwise, all technical and scientific terms used herein have the same meaning as commonly understood by a person of ordinary skill in the art. Additional definitions are set forth throughout the detailed description.

"Hyperphenylalaninemia," "hyperphenylalaninemic," and "excess phenylalanine" are used interchangeably herein to refer to increased or abnormally high concentrations of phenylalanine in the body. In some embodiments, a diagnostic signal of hyperphenylalaninemia is a blood phenylalanine level of at least 2 mg/dL, at least 4 mg/dL, at least 6 mg/dL, at least 8 mg/dL, at least 10 mg/dL, at least 12 mg/dL, at least 14 mg/dL, at least 16 mg/dL, at least 18 mg/dL, at least 20 mg/dL, or at least 25 mg/dL. As used herein, diseases associated with hyperphenylalaninemia include, but are not limited to, phenylketonuria, classical or typical phenylketonuria, atypical phenylketonuria, permanent mild hyperphenylalaninemia, nonphenylketonuric hyperphenylalaninemia, phenylalanine hydroxylase deficiency, cofactor deficiency, dihydropteridine reductase deficiency, tetrahydropterin synthase deficiency, and Segawa's disease. Affected individuals can suffer progressive and irreversible neurological deficits, mental retardation, encephalopathy, epilepsy, eczema, reduced growth, microcephaly, tremor, limb spasticity, and/or hypopigmentation (Leonard 2006). Hyperphenylalaninemia can also be secondary to other conditions, e.g., liver diseases.

"Phenylalanine ammonia lyase" and "PAL" are used to refer to a PME that converts or processes phenylalanine to trans-cinnamic acid and ammonia. Trans-cinnamic acid has low toxicity and is converted by liver enzymes in mammals to hippuric acid, which is secreted in the urine. PAL may be substituted for the enzyme PAH to metabolize excess phenylalanine. PAL enzyme activity does not require THB cofactor activity. In some embodiments, PAL is encoded by a PAL gene from or derived from a prokaryotic species. In alternate embodiments, PAL is encoded by a PAL gene derived from or from a eukaryotic species. In some embodiments, PAL is encoded by a PAL gene from or derived from a bacterial species, including but not limited to, *Achromobacter xylosoxidans, Pseudomonas aeruginosa, Photorhabdus luminescens, Anabaena variabilis,* and *Agrobacterium tumefaciens.* In some embodiments, PAL is encoded by a PAL gene derived from *Anabaena variabilis* and referred to as "PAL1" herein (Moffitt et al., 2007). In some embodiments, PAL is encoded by a PAL gene derived from *Photorhabdus luminescens* and referred to as "PAL3" herein (Williams et al., 2005). In some embodiments, PAL is encoded by a PAL gene derived from a yeast species, e.g., Rhodosporidium toruloides (Gilbert et al., 1985). In some embodiments, PAL is encoded by a PAL gene derived from a plant species, e.g., *Arabidopsis thaliana* (Wanner et al., 1995). Any suitable nucleotide and amino acid sequences of PAL, or functional fragments thereof, may be used.

As used herein, PAL encompasses wild type, naturally occurring PAL as well as mutant, non-naturally occurring PAL. As used herein, a "mutant PAL" or "PAL mutant" refers to a non-naturally occurring and/or synthetic PAL that has been modified, e.g., mutagenized, compared to a wild type, naturally occurring PAL polynucleotide or polypeptide sequence. In some embodiments, the modification is a silent mutation, e.g., a change in the polynucleotide sequence without a change in the corresponding polypeptide sequence. In some embodiments, the mutant PAL exhibits increased stability and/or increased ability to metabolize phenylalanine and/or reduce hyperphenylalaninemia as compared to the wild type PAL. In some embodiments the mutant PAL is derived from *Photorhabdus luminescens* PAL. In some embodiments, the mutant PAL polypeptide comprises one or more mutations at amino acid positions 92, 133, 167, 432, 470, 433, 263, 366 and/or 396 compared to a wild type PAL, e.g., *P. luminescens* PAL. In some embodiments, the mutant PAL polypeptide comprises one or more mutations at amino acid positions S92, H133, I167, L432, V470, A433, A263, K366, and/or L396 compared to a wild type PAL, e.g., *P. luminescens* PAL. In some embodiments, the mutant PAL polypeptide comprises one or more mutations at amino acid positions S92G, H133F, I167K, L432I, V470A, A433S, A263T, K366K (e.g., silent mutation in polynucleotide sequence), and/or L396L (e.g., silent mutation in polynucleotide sequence) compared to the positions in a wild type PAL, e.g., *P. luminescens* PAL. In some embodiments, the mutant PAL polypeptide comprises S92G; H133M; I167K; L432I; V470A compared to the positions in a wild type PAL, e.g., *P. luminescens* PAL. In some embodiments, the mutant PAL polypeptide comprises S92G; H133F; A433S; V470A compared to the positions in a wild type PAL, e.g., *P. luminescens* PAL. In some embodiments, the mutant PAL polypeptide comprises S92G; H133F; A263T; K366K (e.g., silent mutation in polynucleotide sequence); L396L (e.g., silent mutation in polynucleotide sequence); V470A compared to the positions in a wild type PAL, e.g., *P. luminescens* PAL.

"Phenylalanine hydroxylase" and "PAH" are used to refer to an enzyme that catalyzes the hydroxylation of the aromatic side chain of phenylalanine to create tyrosine in the human body in conjunction with the cofactor tetrahydrobiopterin. The human gene encoding PAH is located on the long (q) arm of chromosome 12 between positions 22 and 24.2. The amino acid sequence of PAH is highly conserved among mammals. Nucleic acid sequences for human and mammalian PAH are well known and widely available. The full-length human cDNA sequence for PAH was reported in 1985 (Kwok et al. 1985). Active fragments of PAH are also well known (e.g., Kobe et al. 1997).

"L-Aminoacid Deaminase" and "LAAD" are used to refer to an enzyme that catalyzes the stereospecific oxidative deamination of L-amino acids to generate their respective keto acids, ammonia, and hydrogen peroxide. For example, LAAD catalyzes the conversion of phenylalanine to phenylpyruvate. Multiple LAAD enzymes are known in the art, many of which are derived from bacteria, such as *Proteus, Providencia*, and *Morganella*, or venom. LAAD is characterized by fast reaction rate of phenylalanine degradation (Hou et al., Appl Microbiol Technol. 2015 October; 99(20): 8391-402; "Production of phenylpyruvic acid from L-phenylalanine using an L-amino acid deaminase from *Proteus mirabilis*: comparison of enzymatic and whole-cell biotransformation approaches"). Most eukaryotic and prokaryotic L-amino acid deaminases are extracellular; however, *Proteus* species LAAD are localized to the plasma membrane (inner membrane), facing outward into the periplasmic space, in which the enzymatic activity resides. As a consequence of this localization, phenylalanine transport through the inner membrane into the cytoplasm is not required for *Proteus* LAAD mediated phenylalanine degradation. Phenylalanine is readily taken up through the outer membrane into the periplasm without a transporter, eliminating the need for a transporter to improve substrate availability. In some embodiments, the genetically engineered microorganisms comprise a LAAD gene derived from a bacterial species, including but not limited to, *Proteus, Providencia*, and *Morganella* bacteria. In some embodiments, the bacterial species is *Proteus mirabilis*. In some embodiments, the bacterial species is *Proteus vulgaris*. In some embodiments, the LAAD encoded by the genetically engineered microorganisms is localized to the plasma membrane, facing into the periplasmic space and with the catalytic activity occurring in the periplasmic space.

"Phenylalanine metabolizing enzyme" or "PME" are used to refer to an enzyme which is able to degrade phenylalanine, e.g., into a non-toxic metabolite. Any phenylalanine metabolizing enzyme known in the art may be encoded by the genetically engineered microorganisms, e.g., bacteria, of the disclosure. PMEs include, but are not limited to, phenylalanine hydroxylase (PAH), phenylalanine ammonia lyase (PAL), aminotransferase, L-amino acid deaminase (LAAD), and phenylalanine dehydrogenases.

Reactions with phenylalanine hydroxylases, phenylalanine dehydrogenases or aminotransferases require cofactors, while LAAD and PAL do not require any additional cofactors. In some embodiments, the PME encoded by the genetically engineered microorganisms requires a cofactor. In some embodiments, this cofactor is provided concurrently or sequentially with the administration of the genetically engineered microorganisms. In other embodiments, the genetically engineered microorganisms can produce the cofactor. In some embodiments, the genetically engineered microorganisms encode a phenylalanine hydroxylase. In some embodiments, the genetically engineered microorganisms encode a phenylalanine dehydrogenase. In some embodiments, the genetically engineered microorganisms encode an aminotransferase. Without wishing to be bound by theory, the lack of need for a cofactor means that the rate of phenylalanine degradation by the enzyme is dependent on the availability of the substrate and is not limited by the availability of the cofactor. In some embodiments, the PME produced by the genetically engineered microorganisms is PAL. In some embodiments, the PME produced by the genetically engineered microorganisms is LAAD. In some embodiments, the genetically engineered microorganisms encode combinations of PMEs.

In some embodiments, the catalytic activity of the PME is dependent on oxygen levels. In some embodiments, the PME is catalytically active under microaerobic conditions. As a non-limiting example, LAAD catalytic activity is dependent on oxygen. In some embodiments, LAAD is active under low oxygen conditions, such as microaerobic conditions. In some embodiments, the PME functions at very low levels of oxygen or in the absence of oxygen, e.g., as found in the colon.

"Phenylalanine metabolite" refers to a metabolite that is generated as a result of the degradation of phenylalanine. The metabolite may be generated directly from phenylalanine, by the enzyme using phenylalanine as a substrate, or indirectly by a different enzyme downstream in the metabolic pathway, which acts on a phenylalanine metabolite substrate. In some embodiments, phenylalanine metabolites are produced by the genetically engineered bacteria encoding a PME. In some embodiments, the phenylalanine metabolite results directly or indirectly from PAL action, e.g., from PAL produced by the genetically engineered microorganisms. Non-limiting examples of such PAL metabolites are trans-cinnamic acid and hippuric acid. In some embodiments, the phenylalanine metabolite results directly or indirectly from LAAD action, e.g., from LAAD produced by the genetically engineered microorganisms. Examples of such LAAD metabolites are phenylpyruvate and phenyllactic acid.

"Phenylalanine transporter" is used to refer to a membrane transport protein that is capable of transporting phenylalanine into bacterial cells (see, e.g., Pi et al., 1991). In *Escherichia coli*, the pheP gene encodes a high affinity phenylalanine-specific permease responsible for phenylalanine transport (Pi et al., 1998). In some embodiments, the phenylalanine transporter is encoded by a pheP gene derived from a bacterial species, including but not limited to, *Acinetobacter calcoaceticus, Salmonella enterica*, and *Escherichia coli*. Other phenylalanine transporters include Aageneral amino acid permease, encoded by the aroP gene, transports three aromatic amino acids, including phenylalanine, with high affinity, and is thought, together with PheP, responsible for the lion share of phenylalanine import. Additionally, a low level of phenylalanine transport activity has been traced to the activity of the LIV-I/LS system, which is a branched-chain amino acid transporter consisting of two periplasmic binding proteins, the LIV-binding protein (LIV-I system) and LS-binding protein (LS system), and membrane components, LivHMGF. In some embodiments, the phenylalanine transporter is encoded by an aroP gene derived from a bacterial species. In some embodiments, the phenylalanine transporter is encoded by LIV-binding protein and LS-binding protein and LivHMGF genes derived from a bacterial species. In some embodiments, the genetically engineered microorganisms comprise more than one type of phenylalanine transporter, selected from pheP, aroP, and the LIV-I/LS system. Exemplary phenylalanine transporters are known in the art, see, e.g., PCT/US2016/032562 and PCT/US2016/062369, the contents of which are hereby incorporated by reference.

"Phenylalanine" and "Phe" are used to refer to an amino acid with the formula $C_6H_5CH_2CH(NH_2)COOH$. Phenylalanine is a precursor for tyrosine, dopamine, norepinephrine, and epinephrine. L-phenylalanine is an essential amino acid and the form of phenylalanine primarily found in dietary protein; the stereoisomer D-phenylalanine is found is lower amounts in dietary protein; DL-phenylalanine is a combination of both forms. Phenylalanine may refer to one or more of L-phenylalanine, D-phenylalanine, and DL-phenylalanine.

As used herein, "gene expression system" refers to a combination of gene(s) and regulatory element(s) that enable or regulate gene expression. A gene expression system may comprise gene(s), e.g., encoding a mutant PAL polypeptide, together with one or more promoters, terminators, enhancers, insulators, silencers and other regulatory sequences to facilitate gene expression. In some embodiments, a gene expression system may comprise a gene encoding a mutant PAL and a promoter to which it is operably linked to facilitate gene expression. In some embodiment, a gene expression system may comprise multiple genes operably linked to one or more promoters to facilitate gene expression. In some embodiments, the multiple genes may be on the same plasmid or chromosome, e.g., in cis and operably linked to the same promoter. In some embodiments, the multiple genes may be on the different plasmid(s) or chromosome(s) and operably linked to the different promoters.

"Operably linked" refers a nucleic acid sequence, e.g., a gene encoding PAL, that is joined to a regulatory region sequence in a manner which allows expression of the nucleic acid sequence, e.g., acts in cis. A regulatory region is a nucleic acid that can direct transcription of a gene of interest and may comprise promoter sequences, enhancer sequences, response elements, protein recognition sites, inducible elements, promoter control elements, protein binding sequences, 5' and 3' untranslated regions, transcriptional start sites, termination sequences, polyadenylation sequences, and introns.

As used herein, a "non-native" nucleic acid sequence refers to a nucleic acid sequence not normally present in a microorganism, e.g., an extra copy of an endogenous sequence, or a heterologous sequence such as a sequence from a different species, strain, or substrain of microorganism, or a sequence that is modified and/or mutated as compared to the unmodified sequence from microorganisms of the same subtype. In some embodiments, the non-native nucleic acid sequence is a synthetic, non-naturally occurring sequence (see, e.g., Purcell et al., 2013). The non-native nucleic acid sequence may be a regulatory region, a promoter, a gene, and/or one or more genes in a gene cassette. In some embodiments, "non-native" refers to two or more nucleic acid sequences that are not found in the same relationship to each other in nature. The non-native nucleic acid sequence may be present on a plasmid or chromosome. In addition, multiple copies of any regulatory region, promoter, gene, and/or gene cassette may be present in the microorganism, wherein one or more copies of the regulatory region, promoter, gene, and/or gene cassette may be mutated or otherwise altered as described herein. In some embodiments, the genetically engineered microorganisms are engineered to comprise multiple copies of the same regulatory region, promoter, gene, and/or gene cassette in order to enhance copy number or to comprise multiple different components of a gene cassette performing multiple different functions. In some embodiments, the genetically engineered microorganisms of the invention comprise a gene encoding a phenylalanine-metabolizing enzyme that is operably linked to an inducible promoter that is not associated with said gene in nature, e.g., an FNR promoter operably linked to a gene encoding PAL or a $P_{araBAD}$ promoter operably linked to LAAD.

An "inducible promoter" refers to a regulatory region that is operably linked to one or more genes, wherein expression of the gene(s) is increased in the presence of an inducer of said regulatory region.

"Exogenous environmental condition(s)" or "environmental conditions" refer to settings or circumstances under which the promoter described herein is induced. The phrase is meant to refer to the environmental conditions external to the engineered microorganism, but endogenous or native to the host subject environment. Thus, "exogenous" and "endogenous" may be used interchangeably to refer to environmental conditions in which the environmental conditions are endogenous to a mammalian body, but external or exogenous to an intact microorganism cell. In some embodiments, the exogenous environmental conditions are specific to the gut of a mammal. In some embodiments, the exogenous environmental conditions are specific to the upper gastrointestinal tract of a mammal. In some embodiments, the exogenous environmental conditions are specific to the lower gastrointestinal tract of a mammal. In some embodiments, the exogenous environmental conditions are specific to the small intestine of a mammal. In some embodiments, the exogenous environmental conditions are low oxygen, microaerobic, or anaerobic conditions, such as the environment of the mammalian gut. In some embodiments, exogenous environmental conditions refer to the presence of molecules or metabolites that are specific to the mammalian gut in a healthy or disease-state, e.g., propionate. In some embodiments, the exogenous environmental condition is a tissue-specific or disease-specific metabolite or molecule(s). In some embodiments, the exogenous environmental condition is a low-pH environment. In some embodiments, the genetically engineered microorganism of the disclosure comprises a pH-dependent promoter. In some embodiments, the genetically engineered microorganism of the disclosure comprises an oxygen level-dependent promoter. In some aspects, bacteria have evolved transcription factors that are capable of sensing oxygen levels. Different signaling pathways may be triggered by different oxygen levels and occur with different kinetics.

As used herein, "exogenous environmental conditions" or "environmental conditions" also refer to settings or circumstances or environmental conditions external to the engineered microorganism, which relate to in vitro culture conditions of the microorganism. "Exogenous environmental conditions" may also refer to the conditions during growth, production, and manufacture of the organism. Such conditions include aerobic culture conditions, anaerobic culture conditions, low oxygen culture conditions and other conditions under set oxygen concentrations. Such conditions also include the presence of a chemical and/or nutritional inducer, such as tetracycline, arabinose, IPTG, rhamnose, and the like in the culture medium. Such conditions also include the temperatures at which the microorganisms are grown prior to in vivo administration. For example, using certain promoter systems, certain temperatures are permissive to expression of a payload, while other temperatures are non-permissive. Oxygen levels, temperature and media composition influence such exogenous environmental conditions. Such conditions affect proliferation rate, rate of induction of the PME (e.g., PAL or LAAD), rate of induction of the transporter (e.g., PheP) and/or other regulators (e.g., FNRS24Y), and overall viability and metabolic activity of the strain during strain production.

An "oxygen level-dependent promoter" or "oxygen level-dependent regulatory region" refers to a nucleic acid sequence to which one or more oxygen level-sensing transcription factors is capable of binding, wherein the binding and/or activation of the corresponding transcription factor activates downstream gene expression. Examples of oxygen level-dependent transcription factors include, but are not limited to, FNR, ANR, and DNR. Corresponding FNR-responsive promoters, ANR-responsive promoters, and DNR-responsive promoters are known in the art (see, e.g., Castiglione et al., 2009; Eiglmeier et al., 1989; Galimand et al., 1991; Hasegawa et al., 1998; Hoeren et al., 1993; Salmon et al., 2003). Non-limiting examples are shown in Table 1. In a non-limiting example, a promoter (PfnrS) was derived from the *E. coli* Nissle fumarate and nitrate reductase gene S (fnrS) that is known to be highly expressed under conditions of low or no environmental oxygen (Durand and Storz, 2010; Boysen et al, 2010). The PfnrS promoter is activated under anaerobic and/or low oxygen conditions by the global transcriptional regulator FNR that is naturally found in Nissle. Under anaerobic and/or low oxygen conditions, FNR forms a dimer and binds to specific sequences in the promoters of specific genes under its control, thereby activating their expression. However, under aerobic conditions, oxygen reacts with iron-sulfur clusters in FNR dimers and converts them to an inactive form. In this way, the PfnrS inducible promoter is adopted to modulate the expression of proteins or RNA. PfnrS is used interchangeably in this application as FNRS, fnrS, FNR, P-FNRS promoter and other such related designations to indicate the promoter PfnrS.

TABLE 1

Examples of transcription factors and responsive genes and regulatory regions

| Transcription factor | Examples of responsive genes, promoters, and/or regulatory regions: |
|---|---|
| FNR | nirB, ydfZ, pdhR, focA, ndH, hlyE, narK, narX, narG, yfiD, tdcD |
| ANR | arcDABC |
| DNR | norb, norC |

Exemplary oxygen-level dependent promoters, e.g., FNR promoters, are well known in the art and exemplary FNR promoters are provided in Table 2. See, e.g., PCT/US2016/032562 and PCT/US2016/062369, the contents of which are hereby incorporated by reference.

TABLE 2

Examples of FNR-responsive regulatory region sequences

| SEQ ID NO | FNR-responsive regulatory region sequences |
|---|---|
| SEQ ID NO: 9 | ATCCCCATCACTCTTGATGGAGATCAATTCCCCAAGCTGCTAGA GCGTTACCTTGCCCTTAAACATTAGCAATGTCGATTTATCAGAG GGCCGACAGGCTCCCACAGGAGAAACCG |
| SEQ ID NO: 10 | CTCTTGATCGTTATCAATTCCCACGCTGTTTCAGAGCGTTACCTT GCCCTTAAACATTAGCAATGTCGATTTATCAGAGGGCCGACAGG CTCCCACAGGAGAAACCG |
| nirB1 SEQ ID NO: 11 | GTCAGCATAACACCCTGACCTCTCATTAATTGTTCATGCCGGGC GGCACTATCGTCGTCCGGCCTTTTCCTCTCTTACTCTGCTACGTA CATCTATTTCTATAAATCCGTTCAATTTGTCTGTTTTTTGCACAA ACATGAAATATCAGACAATTCCGTGACTTAAGAAAATTTATACA AATCAGCAATATACCCCTTAAGGAGTATATAAAGGTGAATTTGA TTTACATCAATAAGCGGGGTTGCTGAATCGTTAAGGTAGGCGGT AATAGAAAAGAAATCGAGGCAAAA |
| nirB2 SEQ ID NO: 12 | CGGCCCGATCGTTGAACATAGCGGTCCGCAGGCGGCACTGCTTA CAGCAAACGGTCTGTACGCTGTCGTCTTTGTGATGTGCTTCCTGT TAGGTTTCGTCAGCCGTCACCGTCAGCATAACACCCTGACCTCT CATTAATTGCTCATGCCGGACGGCACTATCGTCGTCCGGCCTTTT CCTCTCTTCCCCCGCTACGTGCATCTATTTCTATAAACCCGCTCA TTTTGTCTATTTTTTGCACAAACATGAAATATCAGACAATTCCGT GACTTAAGAAAATTTATACAAATCAGCAATATACCCATTAAGGA GTATATAAAGGTGAATTTGATTTACATCAATAAGCGGGGTTGCT GAATCGTTAAGGTAGGCGGTAATAGAAAAGAAATCGAGGCAAA Aatgtttgtttaactttaagaaggagatatacat |
| nirB3 SEQ ID NO: 13 | GTCAGCATAACACCCTGACCTCTCATTAATTGCTCATGCCGGAC GGCACTATCGTCGTCCGGCCTTTTCCTCTCTTCCCCCGCTACGTG CATCTATTTCTATAAACCGCTCATTTTGTCTATTTTTTGCACAA ACATGAAATATCAGACAATTCCGTGACTTAAGAAAATTTATACA AATCAGCAATATACCCATTAAGGAGTATATAAAGGTGAATTTGA TTTACATCAATAAGCGGGGTTGCTGAATCGTTAAGGTAGGCGGT AATAGAAAAGAAATCGAGGCAAAA |
| ydfZ SEQ ID NO: 14 | ATTTCCTCTCATCCCATCCGGGGTGAGAGTCTTTTCCCCCGACTT ATGGCTCATGCATGCATCAAAAAAGATGTGAGCTTGATCAAAA ACAAAAAATATTTCACTCGACAGGAGTATTTATATTGCGCCCGT TACGTGGGCTTCGACTGTAAATCAGAAAGGAGAAAACACCT |

TABLE 2-continued

Examples of FNR-responsive regulatory region sequences

| SEQ ID NO | FNR-responsive regulatory region sequences |
|---|---|
| nirB+RBS SEQ ID NO: 15 | GTCAGCATAACACCCTGACCTCTCATTAATTGTTCATGCCGGGC GGCACTATCGTCGTCCGGCCTTTTCCTCTCTTACTCTGCTACGTA CATCTATTTCTATAAATCCGTTCAATTTGTCTGTTTTTTGCACAA ACATGAAATATCAGACAATTCCGTGACTTAAGAAAATTTATACA AATCAGCAATATACCCCTTAAGGAGTATATAAAGGTGAATTTGA TTTACATCAATAAGCGGGGTTGCTGAATCGTTAAGGATCCCTCT AGAAATAATTTTGTTTAACTTTAAGAAGGAGATATACAT |
| ydfZ+RBS SEQ ID NO: 16 | CATTTCCTCTCATCCCATCCGGGGTGAGAGTCTTTTCCCCCGACT TATGGCTCATGCATGCATCAAAAAAGATGTGAGCTTGATCAAAA ACAAAAAATATTTCACTCGACAGGAGTATTTATATTGCGCCCGG ATCCCTCTAGAAATAATTTTGTTTAACTTTAAGAAGGAGATATA CAT |
| fnrS1 SEQ ID NO: 17 | AGTTGTTCTTATTGGTGGTGTTGCTTTATGGTTGCATCGTAGTAA ATGGTTGTAACAAAAGCAATTTTTCCGGCTGTCTGTATACAAAA ACGCCGTAAAGTTTGAGCGAAGTCAATAAACTCTCTACCCATTC AGGGCAATATCTCTCTTGGATCCCTCTAGAAATAATTTTGTTTA ACTTTAAGAAGGAGATATACAT |
| fnrS2 SEQ ID NO: 18 | AGTTGTTCTTATTGGTGGTGTTGCTTTATGGTTGCATCGTAGTAA ATGGTTGTAACAAAAGCAATTTTTCCGGCTGTCTGTATACAAAA ACGCCGCAAAGTTTGAGCGAAGTCAATAAACTCTCTACCCATTC AGGGCAATATCTCTCTTGGATCCAAAGTGAACTCTAGAAATAAT TTTGTTTAACTTTAAGAAGGAGATATACAT |
| nirB+crp SEQ ID NO: 19 | TCGTCTTTGTGATGTGCTTCCTGTTAGGTTTCGTCAGCCGTCACC GTCAGCATAACACCCTGACCTCTCATTAATTGCTCATGCCGGAC GGCACTATCGTCGTCCGGCCTTTTCCTCTCTTCCCCCGCTACGTG CATCTATTTCTATAAACCCGCTCATTTTGTCTATTTTTTGCACAA ACATGAAATATCAGACAATTCCGTGACTTAAGAAAATTTATACA AATCAGCAATATACCCATTAAGGAGTATATAAAGGTGAATTTGA TTTACATCAATAAGCGGGGTTGCTGAATCGTTAAGGTAGaaatgtgat ctagttcacattGCGGTAATAGAAAAGAAATCGAGGCAAAA*atgtttgtttaac tttaagaaggagatatacat* |
| fnrS+crp SEQ ID NO: 20 | AGTTGTTCTTATTGGTGGTGTTGCTTTATGGTTGCATCGTAGTAA ATGGTTGTAACAAAAGCAATTTTTCCGGCTGTCTGTATACAAAA ACGCCGCAAAGTTTGAGCGAAGTCAATAAACTCTCTACCCATTC AGGGCAATATCTCTC*aaatgtgatctagttcacattttttgtttaactttaaga aggagatatacat* |

As used herein, the term "low oxygen" is meant to refer to a level, amount, or concentration of oxygen ($O_2$) that is lower than the level, amount, or concentration of oxygen that is present in the atmosphere (e.g., <21% $O_2$; <160 torr $O_2$)). Thus, the term "low oxygen condition or conditions" or "low oxygen environment" refers to conditions or environments containing lower levels of oxygen than are present in the atmosphere. In some embodiments, the term "low oxygen" is meant to refer to the level, amount, or concentration of oxygen ($O_2$) found in a mammalian gut, e.g., lumen, stomach, small intestine, duodenum, jejunum, ileum, large intestine, cecum, colon, distal sigmoid colon, rectum, and anal canal. In some embodiments, the term "low oxygen" is meant to refer to a level, amount, or concentration of $O_2$ that is 0-60 mmHg $O_2$ (0-60 torr $O_2$) (e.g., 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, and 60 mmHg $O_2$), including any and all incremental fraction(s) thereof (e.g., 0.2 mmHg, 0.5 mmHg $O_2$, 0.75 mmHg $O_2$, 1.25 mmHg $O_2$, 2.175 mmHg $O_2$, 3.45 mmHg $O_2$, 3.75 mmHg $O_2$, 4.5 mmHg $O_2$, 6.8 mmHg $O_2$, 11.35 mmHg $O_2$, 46.3 mmHg $O_2$, 58.75 mmHg, etc., which exemplary fractions are listed here for illustrative purposes and not meant to be limiting in any way). In some embodiments, "low oxygen" refers to about 60 mmHg $O_2$ or less (e.g., 0 to about 60 mmHg $O_2$). The term "low oxygen" may also refer to a range of $O_2$ levels, amounts, or concentrations between 0-60 mmHg $O_2$ (inclusive), e.g., 0-5 mmHg $O_2$, <1.5 mmHg $O_2$, 6-10 mmHg, <8 mmHg, 47-60 mmHg, etc. which listed exemplary ranges are listed here for illustrative purposes and not meant to be limiting in any way. See, for example, Albenberg et al., Gastroenterology, 147 (5): 1055-1063 (2014); Bergofsky et al., J Clin. Invest., 41(11): 1971-1980 (1962); Crompton et al., J Exp. Biol., 43: 473-478 (1965); He et al., PNAS (USA), 96: 4586-4591 (1999); McKeown, Br. J. Radiol., 87:20130676 (2014) (doi: 10.1259/brj.20130676), each of which discusses the oxygen levels found in the mammalian gut of various species and each of which are incorporated by reference herewith in their entireties. In some embodiments, the term "low oxygen" is meant to refer to the level, amount, or concentration of oxygen ($O_2$) found in a mammalian organ or tissue other than the gut, e.g., urogenital tract, tumor tissue, etc. in which oxygen is present at a reduced level, e.g., at a hypoxic or anoxic level. In some embodiments, "low oxygen" is meant to refer to the level, amount, or concentration of oxygen ($O_2$) present in partially aerobic, semi aerobic, microaerobic, nanoaerobic, microoxic, hypoxic, anoxic, and/or anaerobic conditions. Summaries of the amount of oxygen present in various organs and tissues are provided in PCT/US2016/062369, the contents of which is herein incorporated by reference in its entirety. In some embodiments, the level, amount, or concentration of oxygen ($O_2$) is expressed as the amount of dissolved oxygen ("DO") which refers to the level of free, non-compound oxygen ($O_2$) present in liquids and is typically reported in milligrams per liter (mg/L), parts per million (ppm; 1 mg/L=1 ppm), or in micromoles (umole) (1 umole $O_2$=0.022391 mg/L $O_2$). Fondriest Environmental, Inc., "Dissolved Oxygen", Fundamentals of Environmental Measurements, 19 Nov. 2013, www.fondriest.com/environ-mental-measurements/parameters/water-quality/dissolved-oxygen/>. In some embodiments, the term "low oxygen" is meant to refer to a level, amount, or concentration of oxygen ($O_2$) that is about 6.0 mg/L DO or less, e.g., 6.0 mg/L, 5.0 mg/L, 4.0 mg/L, 3.0 mg/L, 2.0 mg/L, 1.0 mg/L, or 0 mg/L, and any fraction therein, e.g., 3.25 mg/L, 2.5 mg/L, 1.75 mg/L, 1.5 mg/L, 1.25 mg/L, 0.9 mg/L, 0.8 mg/L, 0.7 mg/L, 0.6 mg/L, 0.5 mg/L, 0.4 mg/L, 0.3 mg/L, 0.2 mg/L and 0.1 mg/L DO, which exemplary fractions are listed here for illustrative purposes and not meant to be limiting in any way. The level of oxygen in a liquid or solution may also be reported as a percentage of air saturation or as a percentage of oxygen saturation (the ratio of the concentration of dissolved oxygen ($O_2$) in the solution to the maximum amount of oxygen that will dissolve in the solution at a certain temperature, pressure, and salinity under stable equilibrium). Well-aerated solutions (e.g., solutions subjected to mixing and/or stirring) without oxygen producers or consumers are 100% air saturated. In some embodiments, the term "low oxygen" is meant to refer to 40% air saturation or less, e.g., 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, 1%, and 0% air saturation, including any and all incremental fraction(s) thereof (e.g., 30.25%, 22.70%, 15.5%, 7.7%, 5.0%, 2.8%, 2.0%, 1.65%, 1.0%, 0.9%, 0.8%, 0.75%, 0.68%, 0.5%. 0.44%, 0.3%, 0.25%, 0.2%, 0.1%, 0.08%, 0.075%, 0.058%, 0.04%. 0.032%, 0.025%, 0.01%, etc.) and any range of air saturation levels between 0-40%, inclusive (e.g., 0-5%, 0.05-0.1%, 0.1-0.2%, 0.1-0.5%, 0.5-2.0%, 0-10%, 5-10%, 10-15%, 15-20%, 20-25%, 25-30%, etc.). The exemplary fractions and ranges listed here are for illustrative purposes and not meant to be limiting in any way. In some embodiments, the term "low oxygen" is meant to refer to 9% $O_2$ saturation or less, e.g., 9%, 8%, 7%, 6%, 5%, 4%, 3%, 2%, 1%, 0%, $O_2$ saturation, including any and all incremental fraction(s) thereof (e.g., 6.5%, 5.0%, 2.2%, 1.7%, 1.4%, 0.9%, 0.8%, 0.75%, 0.68%, 0.5%. 0.44%, 0.3%, 0.25%, 0.2%, 0.1%, 0.08%, 0.075%, 0.058%, 0.04%. 0.032%, 0.025%, 0.01%, etc.) and any range of $O_2$ saturation levels between 0-9%, inclusive (e.g., 0-5%, 0.05-0.1%, 0.1-0.2%, 0.1-0.5%, 0.5-2.0%, 0-8%, 5-7%, 0.3-4.2% 02, etc.). The exemplary fractions and ranges listed here are for illustrative purposes and not meant to be limiting in any way.

"Constitutive promoter" refers to a promoter that is capable of facilitating continuous transcription of a coding sequence or gene under its control and/or to which it is operably linked.

Constitutive promoters, inducible promoters, and variants thereof are well known in the art and described in PCT/US2016/032562 and PCT/US2016/062369, the contents of which are hereby incorporated by reference.

"Gut" refers to the organs, glands, tracts, and systems that are responsible for the transfer and digestion of food, absorption of nutrients, and excretion of waste. In humans, the gut comprises the gastrointestinal (GI) tract, which starts at the mouth and ends at the anus, and additionally comprises the esophagus, stomach, small intestine, and large intestine. The gut also comprises accessory organs and glands, such as the spleen, liver, gallbladder, and pancreas. The upper gastrointestinal tract comprises the esophagus, stomach, and duodenum of the small intestine. The lower gastrointestinal tract comprises the remainder of the small intestine, i.e., the jejunum and ileum, and all of the large intestine, i.e., the cecum, colon, rectum, and anal canal. Bacteria can be found throughout the gut, e.g., in the gastrointestinal tract, and particularly in the intestines. In some embodiments, the genetically engineered microorganisms are active (e.g., express one or more PMEs) in the gut. In some embodiments, the genetically engineered microorganisms are active (e.g., express one or more PMEs) in the large intestine. In some embodiments, the genetically engineered microorganisms are active (e.g., express one or more PMEs) in the small intestine. In some embodiments, the genetically engineered microorganisms are active in the small intestine and in the large intestine. Without wishing to be bound by theory, phenylalanine degradation may be every effective in the small intestine, because amino acid absorption, e.g., phenylalanine absorption, occurs in the small intestine. Through the prevention or reduction of phenylalanine uptake into the blood, increased levels and resulting Phe toxicity can be avoided. Additionally, extensive enterorecirculation of amino acids between the intestine and the body may allow the removal of systemic phenylalanine in PKU (e.g., described by Chang et al., in a rat model of PKU (Chang et al., A new theory of enterorecirculation of amino acids and its use for depleting unwanted amino acids using oral enzyme-artificial cells, as in removing phenylalanine in phenylketonuria; Artif Cells Blood Substit Immobil Biotechnol. 1995; 23(1):1-21)). Phenylalanine from the blood circulates into the small intestine and can be cleared by microorganisms which are active at this location. In some embodiments, the genetically engineered microorganisms transit through the small intestine. In some embodiments, the genetically engineered microorganisms have increased residence time in the small intestine. In some embodiments, the genetically engineered microorganisms colonize the small intestine. In some embodiments, the genetically engineered microorganisms do not colonize the small intestine. In some embodiments, the genetically engineered microorganisms have increased residence time in the gut. In some embodiments, the genetically engineered microorganisms colonize the gut. In some embodiments, the genetically engineered microorganisms do not colonize the gut.

"Microorganism" refers to an organism or microbe of microscopic, submicroscopic, or ultramicroscopic size that typically consists of a single cell. Examples of microorganisms include bacteria, yeast, viruses, parasites, fungi, certain algae, and protozoa. In some aspects, the microorganism is engineered ("engineered microorganism") to produce one or more therapeutic molecules or proteins of interest. In certain aspects, the microorganism is engineered to take up and catabolize certain metabolites or other compounds from its environment, e.g., the gut. In certain aspects, the microorganism is engineered to synthesize certain beneficial metabolites or other compounds (synthetic or naturally occurring) and release them into its environment. In certain embodiments, the engineered microorganism is an engineered bacterium. In certain embodiments, the engineered microorganism is an engineered virus.

"Non-pathogenic bacteria" refer to bacteria that are not capable of causing disease or harmful responses in a host. In some embodiments, non-pathogenic bacteria are Gram-negative bacteria. In some embodiments, non-pathogenic bacteria are Gram-positive bacteria. In some embodiments, non-pathogenic bacteria are commensal bacteria, which are present in the indigenous microbiota of the gut. Examples of non-pathogenic bacteria include, but are not limited to, *Bacillus, Bacteroides, Bifidobacterium, Brevibacteria, Clostridium, Enterococcus, Escherichia, Lactobacillus, Lactococcus, Saccharomyces*, and *Staphylococcus*, e.g., *Bacillus coagulans, Bacillus subtilis, Bacteroides fragilis, Bacteroides subtilis, Bacteroides thetaiotaomicron, Bifidobacterium bifidum, Bifidobacterium infantis, Bifidobacterium lactis, Bifidobacterium longum, Clostridium butyricum, Enterococcus faecium, Escherichia coli, Lactobacillus acidophilus, Lactobacillus bulgaricus, Lactobacillus casei, Lactobacillus johnsonii, Lactobacillus paracasei, Lactobacillus plantarum, Lactobacillus reuteri, Lactobacillus rhamnosus, Lactococcus lactis*, and *Saccharomyces boulardii* (Sonnenborn et al., 2009; Dinleyici et al., 2014; U.S. Pat. Nos. 6,835,376; 6,203,797; 5,589,168; 7,731,976). Naturally pathogenic bacteria may be genetically engineered to provide reduce or eliminate pathogenicity.

"Probiotic" is used to refer to live, non-pathogenic microorganisms, e.g., bacteria, which can confer health benefits to a host organism that contains an appropriate amount of the microorganism. In some embodiments, the host organism is a mammal. In some embodiments, the host organism is a human. Some species, strains, and/or subtypes of non-pathogenic bacteria are currently recognized as probiotic. Examples of probiotic bacteria include, but are not limited to, Bifidobacteria, *Escherichia, Lactobacillus*, and *Saccharomyces*, e.g., *Bifidobacterium bifidum, Enterococcus faecium, Escherichia coli, Escherichia coli* strain Nissle, *Lactobacillus acidophilus, Lactobacillus bulgaricus, Lactobacillus paracasei, Lactobacillus plantarum*, and *Saccharomyces boulardii* (Dinleyici et al., 2014; U.S. Pat. Nos. 5,589,168; 6,203,797; 6,835,376). The probiotic may be a variant or a mutant strain of bacterium (Arthur et al., 2012; Cuevas-Ramos et al., 2010; Olier et al., 2012; Nougayrede et al., 2006). Non-pathogenic bacteria may be genetically engineered to enhance or improve desired biological properties, e.g., survivability. Non-pathogenic bacteria may be genetically engineered to provide probiotic properties. Probiotic bacteria may be genetically engineered to enhance or improve probiotic properties.

As used herein, "stable" microorganism is used to refer to a microorganism host cell carrying non-native genetic material, e.g., a PAL gene, which is incorporated into the host genome or propagated on a self-replicating extra-chromosomal plasmid, such that the non-native genetic material is retained, expressed, and/or propagated, e.g., under particular conditions. The stable microorganism is capable of survival and/or growth in vitro, e.g., in medium, and/or in vivo, e.g., in the gut. For example, the stable microorganisms may be a genetically modified bacterium comprising a PAL gene, e.g., mutant PAL, in which the plasmid or chromosome carrying the PAL gene is stably maintained in the host cell, such that PAL can be expressed in the host cell, and the host cell is capable of survival and/or growth in vitro and/or in vivo. In some embodiments, copy number affects the stability of expression of the non-native genetic material, e.g., a PAL gene or a PAH gene. In some embodiments, copy number affects the level of expression of the non-native genetic material, e.g., a PAL gene or a PAH gene.

As used herein, the terms "modulate" and "treat" and their cognates refer to an amelioration of a disease, disorder, and/or condition, or at least one discernible symptom thereof. In another embodiment, "modulate" and "treat" refer to an amelioration of at least one measurable physical parameter, not necessarily discernible by the patient. In another embodiment, "modulate" and "treat" refer to inhibiting the progression of a disease, disorder, and/or condition, either physically (e.g., stabilization of a discernible symptom), physiologically (e.g., stabilization of a physical parameter), or both. In another embodiment, "modulate" and "treat" refer to slowing the progression or reversing the progression of a disease, disorder, and/or condition. As used herein, "prevent" and its cognates refer to delaying the onset or reducing the risk of acquiring a given disease, disorder and/or condition or a symptom associated with such disease, disorder, and/or condition. Those in need of treatment may include individuals already having a particular medical disease, as well as those at risk of having, or who may ultimately acquire the disease. The need for treatment is assessed, for example, by the presence of one or more risk factors associated with the development of a disease, the presence or progression of a disease, or likely receptiveness to treatment of a subject having the disease. Primary hyperphenylalaninemia, e.g., PKU, is caused by inborn genetic mutations for which there are no known cures. Hyperphenylalaninemia can also be secondary to other conditions, e.g., liver diseases. Treating hyperphenylalaninemia may encompass reducing or eliminating excess phenylalanine and/or associated symptoms and does not necessarily encompass the elimination of the underlying disease.

As used herein a "pharmaceutical composition" refers to a preparation of genetically engineered bacteria of the invention with other components such as a physiologically suitable carrier and/or excipient.

The phrases "physiologically acceptable carrier" and "pharmaceutically acceptable carrier" which may be used interchangeably refer to a carrier or a diluent that does not cause significant irritation to an organism and does not abrogate the biological activity and properties of the administered bacterial compound. An adjuvant is included under these phrases.

The term "excipient" refers to an inert substance added to a pharmaceutical composition to further facilitate administration of an active ingredient. Examples include, but are not limited to, calcium bicarbonate, calcium phosphate, various sugars and types of starch, cellulose derivatives, gelatin, vegetable oils, polyethylene glycols, and surfactants, including, for example, polysorbate 20.

The terms "therapeutically effective dose" and "therapeutically effective amount" are used to refer to an amount of a compound that results in prevention, delay of onset of symptoms, or amelioration of symptoms of a condition, e.g., hyperphenylalaninemia. A therapeutically effective amount may, for example, be sufficient to treat, prevent, reduce the severity, delay the onset, and/or reduce the risk of occurrence of one or more symptoms of a disease or condition associated with excess phenylalanine levels. A therapeutically effective amount, as well as a therapeutically effective frequency of administration, can be determined by methods known in the art and discussed below.

As used herein, the term "polypeptide" includes "polypeptide" as well as "polypeptides," and refers to a molecule composed of amino acid monomers linearly linked by amide bonds (i.e., peptide bonds). The term "polypeptide" refers to any chain or chains of two or more amino acids and does not refer to a specific length of the product. Thus, "peptides," "dipeptides," "tripeptides," "oligopeptides," "protein," "amino acid chain," or any other term used to refer to a chain or chains of two or more amino acids, are included within the definition of "polypeptide," and the term "polypeptide" may be used instead of, or interchangeably with any of these terms. The term "dipeptide" refers to a peptide of two linked amino acids. The term "tripeptide" refers to a peptide of three linked amino acids. The term "polypeptide" is also intended to refer to the products of post-expression modifications of the polypeptide, including but not limited to glycosylation, acetylation, phosphorylation, amidation, derivatization, proteolytic cleavage, or modification by non-naturally occurring amino acids. A polypeptide may be derived from a natural biological source or produced by recombinant technology. In other embodiments, the polypeptide is produced by the genetically engineered microorganism of the current invention.

The terms "phage" and "bacteriophage" are used interchangeably herein. Both terms refer to a virus that infects and replicates within a bacterium. As used herein "phage" or "bacteriophage" collectively refers to prophage, lysogenic, dormant, temperate, intact, defective, cryptic, and satellite phage, phage tail bacteriocins, tailiocins, and gene transfer agents.

As used therein the term "prophage" refers to the genomic material of a bacteriophage, which is integrated into a replicon of the host cell and replicates along with the host. The prophage may be able to produce phages if specifically activated. In some cases, the prophage is not able to produce phages or has never done so (i.e., defective or cryptic prophages). In some cases, prophage also refers to satellite phages. The terms "prophage" and "endogenous phage" are used interchangeably herein.

"Endogenous phage" or "endogenous prophage" also refers to a phage that is present in the natural state of a bacterium (and its parental strain).

As used herein the term "phage knockout" or "inactivated phage" refers to a phage which has been modified so that it can either no longer produce and/or package phage particles or it produces fewer phage particles than the wild type phage sequence. In some embodiments, the inactivated phage or phage knockout refers to the inactivation of a temperate phage in its lysogenic state, i.e., to a prophage. Such a modification refers to a mutation in the phage; such mutations include insertions, deletions (partial or complete deletion of phage genome), substitutions, inversions, at one or more positions within the phage genome, e.g., within one or more genes within the phage genome.

As used herein the adjectives "phage-free", "phage free" and "phageless" are used interchangeably to characterize a bacterium or strain which contains one or more prophages, one or more of which have been modified. The modification can result in a loss of the ability of the prophage to be induced or release phage particles. Alternatively, the modification can result in less efficient or less frequent induction or less efficient or less frequent phage release as compared to the isogenic strain without the modification. Ability to induce and release phage can be measured using a plaque assay as described herein.

As used herein phage induction refers to the part of the life cycle of a lysogenic prophage, in which the lytic phage genes are activated, phage particles are produced and lysis occurs.

PAL Mutants

The present disclosure provides mutant PAL polypeptides and polynucleotides encoding the same. In some embodiments, the mutant PAL is encoded by a gene derived from a prokaryotic species. In some embodiments, the mutant PAL is encoded by a gene derived from a eukaryotic species. In some embodiments, the mutant PAL is encoded by a PAL gene derived from a bacterial species, including but not limited to, *Achromobacter xylosoxidans, Pseudomonas aeruginosa, Photorhabdus luminescens, Anabaena variabilis,* and *Agrobacterium tumefaciens.* In some embodiments, the mutant PAL is encoded by a PAL gene derived from *Anabaena variabilis.* In some embodiments, the mutant PAL is encoded by a PAL gene derived from *Photorhabdus luminescens.* In some embodiments, the mutant PAL is encoded by a PAL gene derived from a yeast species, e.g., *Rhodosporidium toruloides.* In some embodiments, the mutant PAL is encoded by a PAL gene derived from a plant species, e.g., *Arabidopsis thaliana.* Any suitable nucleotide and amino acid sequences of PAL, or functional fragments thereof, may be used to derive the mutant PAL. In some embodiments, the mutant PAL exhibits increased stability and/or activity compared to the wild type PAL. Non-limiting examples of PAL genes are shown in Table 3.

TABLE 3

Sequences of Exemplary Phenylalanine Metabolizing Enzymes

| Description | Sequence |
| --- | --- |
| Phenylalanine ammonia-lyase (*Anabaena variabilis*) Acc. No.: Q3M5Z3.1 | MKTLSQAQSKTSSQQFSFTGNSSANVIIGNQKLTINDVARVARN GTLVSLTNNTDILQGIQASCDYINNAVESGEPIYGVTSGFGGMAN VAISREQASELQTNLVWFLKTGAGNKLPLADVRAAMLLRANSH MRGASGIRLELIKRMEIFLNAGVTPYVYEFGSIGASGDLVPLSYIT GSLIGLDPSFKVDFNGKEMDAPTALRQLNLSPLTLLPKEGLAMM NGTSVMTGIAANCVYDTQILTAIAMGVHALDIQALNGTNQSFHP FIHNSKPHPGQLWAADQMISLLANSQLVRDELDGKHDYRDHELI QDRYSLRCLPQYLGPIVDGISQIAKQIEIEINSVTDNPLIDVDNQA SYHGGNFLGQYVGMGMDHLRYYIGLLAKHLDVQIALLASPEFS NGLPPSLLGNRERKVNMGLKGLQICGNSIMPLLTFYGNSIADRFP THAEQFNQNINSQGYTSATLARRSVDIFQNYVAIALMFGVQAVD LRTYKKTGHYDARACLSPATERLYSAVRHVVGQKPTSDRPYIW NDNEQGLDEHIARISADIAAGGVIVQAVQDILPCLH (SEQ ID NO: 21) |
| histidine ammonia-lyase [*Anabaena variabilis* ATCC 29413] (Acc. NO: ABA23593.1) | MKTLSQAQSKTSSQQFSFTGNSSANVIIGNQKLTINDVARVARN GTLVSLTNNTDILQGIQASCDYINNAVESGEPIYGVTSGFGGMAN VAISREQASELQTNLVWFLKTGAGNKLPLADVRAAMLLRANSH MRGASGIRLELIKRMEIFLNAGVTPYVYEFGSIGASGDLVPLSYIT GSLIGLDPSFKVDFNGKEMDAPTALRQLNLSPLTLLPKEGLAMM NGTSVMTGIAANCVYDTQILTAIAMGVHALDIQALNGTNQSFHP FIHNSKPHPGQLWAADQMISLLANSQLVRDELDGKHDYRDHELI QDRYSLRCLPQYLGPIVDGISQIAKQIEIEINSVTDNPLIDVDNQA SYHGGNFLGQYVGMGMDHLRYYIGLLAKHLDVQIALLASPEFS |

TABLE 3-continued

Sequences of Exemplary Phenylalanine Metabolizing Enzymes

| Description | Sequence |
|---|---|
| | NGLPPSLLGNRERKVNMGLKGLQICGNSIMPLLTFYGNSIADRFP<br>THAEQFNQNINSQGYTSATLARRSVDIFQNYVAIALMFGVQAVD<br>LRTYKKTGHYDARACLSPATERLYSAVRHVVGQKPTSDRPYIW<br>NDNEQGLDEHIARISADIAAGGVIVQAVQDILPCLH (SEQ ID NO: 21) |
| histidine<br>ammonia-lyase<br>[Photorhabdus<br>luminescens]<br>(WP_011146484) | MKAKDVQPTIIINKNGLISLEDIYDIAIKQKKVEISTEITELLTHGR<br>EKLEEKLNSGEVIYGINTGFGGNANLVVPPFEKIAEHQQNLLTFLS<br>AGTGDYMSKPCIKASQFTMLLSVCKGWSATRPIVAQAIVDHINH<br>DIVPLVPRYGSVGASGDLIPLSYIARALCGIGKVYYMGAEIDAAE<br>AIKRAGLTPLSLKAKEGLALINGTRVMSGISAITVIKLEKLFKASI<br>SAIALAVEALLASHEHYDARIQQVKNHPGQNAVASALRNLLAG<br>STQVNLLSGVKEQANKACRHQEITQLNDTLQEVYSIRCAPQVLG<br>IVPESLATARKILEREVISANDNPLIDPENGDVLHGGNFMGQYVA<br>RTMDALKLDIALIANHLHAIVALMMDNRFSRGLPNSLSPTPGMY<br>QGFKGVQLSQTALVAAIRHDCAASGIHTLATEQYNQDIVSLGLH<br>AAQDVLEMEQKLRNIVSMTILVVCQAIHLRGNISEIAPETAKFYH<br>AVREISSPLITDRALDEDIIRIADAIINDQLPLPEIMLEE (SEQ ID NO: 1) |
| Histidine<br>ammonia lyase<br>(Photorhabdus<br>luminescens)<br>Acc. NO:<br>CAE15566 | MKQLTIYPGKLTLDELRQVYLQPVKITLDSQIFPAIERSVECVNAI<br>LAENRTAYGINTGFGLLASTRIEEDNLEKLQRSLVVSHAAGVGK<br>ALDDNMTRLIMVLKINSLSRGYSGIRLAVIQALIALVNAEIYPHIP<br>CKGSVGASGDLAPLAHMSLLLLGEGQARYQGEWLPAKEALAK<br>ANLQPITLAAKEGLALLNGTQVSTAFALRGLFEAEDLLAAAIVC<br>GSLSVEAALGSRKPFDARVHVVRGQQGQIDVAALYRHVLEESS<br>ELSDSHINCPKVQDPYSLRCQPQVMGACLTQLRHAADVILTEAN<br>AVSDNPLVFAEQGEVISGGNFHAEPVAMASDNLALVLAEIGALS<br>ERRIALLMDSHMSQLPPFLVENGGVNSGFMIAQVTAAALASENK<br>ALAHPASVDSLPTSANQEDHVSMAPAAGRRLWEMAENTRGILA<br>IEWLSACQGIDFRNGLKSSPILEEARVILRAKVDYYDQDRFFAPD<br>IDAAVKLLAEQHLSSLLPSGQILQRKNNR (SEQ ID NO: 22) |
| amino acid<br>deaminase<br>(Proteus<br>mirabilis) Acc.<br>No: ACD36582 | MAISRRKFILGGTVVAVAAGAGVLTPMLTREGRFVPGTPRHGFV<br>EGTGGPLPKQDDVVVIGAGILGIMTAINLAERGLSVTIVEKGNIA<br>GEQSSRFYGQAISYKMPDETFLLHHLGKHRWREMNAKVGIDTT<br>YRTQGRVEVPLDEEDLENVRKWIDAKSKDVGSDIPFRTKMIEGA<br>ELKQRLRGATTDWKIAGFEEDSGSFDPEVATFVMAEYAKKMGI<br>KIFTNCAARGLETQAGVISDVVTEKGPIKTSRVVVAGGVGSRLF<br>MQNLNVDVPTLPAYQSQQLISAAPNAPGGNVALPGGIFFRDQAD<br>GTYATSPRVIVAPVVKESFTYGYKYLPLLALPDFPVHISLNEQLI<br>NSFMQSTHWDLNEESPFEKYRDMTALPDLPELNASLEKLKKEFP<br>AFKESTLIDQWSGAMAIAPDENPIISDVKEYPGLVINTATGWGM<br>TESPVSAEITADLLLGKKPVLDAKPFSLYRF (SEQ ID NO: 23) |
| amino acid<br>deaminase<br>[Proteus<br>mirabilis<br>HI4320]) Acc.<br>No.:<br>AAA86752.1 | MNISRRKLLLGVGAAGVLAGGAALVPMVRRDGKFVEAKSRASF<br>VEGTQGALPKEADVVIIGAGIQGIMTAINLAERGMSVTILEKGQI<br>AGEQSGRAYSQIISYQTSPEIFPLHHYGKILWRGMNEKIGADTSY<br>RTQGRVEALADEKALDKAQAWIKTAKEAAGFDTPLNTRIIKGEE<br>LSNRLVGAQTPWTVAAFEEDSGSVDPETGTPALARYAKQIGVKI<br>YTNCAVRGIETAGGKISDVVSEKGAIKTSQVVLAGGIWSRLFMG<br>NMGIDIPTLNVYLSQQRVSGVPGAPRGNVHLPNGIHFREQADGT<br>YAVAPRIFTSSIVKDSFLLGPKFMHLLGGGELPLEFSIGEDLFNSF<br>KMPTSWNLDEKTPFEQFRVATATQNTQHLDAVFQRMKTEFPVF<br>EKSEVVERWGAVVSPTFDELPIISEVKEYPGLVINTATVWGMTE<br>GPAAGEVTADIVMGKKPVIDPTPFSLDRFKK (SEQ ID NO: 24) |
| L-AAD from<br>Proteus vulgaris;<br>(Acc. NO:<br>BAA90864) | MAISRRKFIIGGTVVAVAAGAGILTPMLTREGRFVPGTPRHGFVE<br>GTEGALPKQADVVVVGAGILGIMTAINLVERGLSVVIVEKGNIA<br>GEQSSRFYGQAISYKMPDETFLLHHLGKHRWREMNAKVGIDTT<br>YRTQGRVEVPLDEEDLVNVRKWIDERSKNVGSDIPFKTRIIEGAE<br>LNQRLRGATTDWKIAGFEEDSGSFDPEVATFVMAEYAKKMGVR<br>IYTQCAARGLETQAGVISDVVTEKGAIKTSQVVVAGGVWSRLF<br>MQNLNVDVPTLPAYQSQQLISGSPTAPGGNVALPGGIFFREQAD<br>GTYATSPRVIVAPVVKESFTYGYKYLPLLALPDFPVHISLNEQLI<br>NSFMQSTHWNLDEVSPFEQFRNMTALPDLPELNASLEKLKAEFP<br>AFKESKLIDQWSGAMAIAPDENPIISEVKEYPGLVINTATGWGM<br>TESPVSAELTADLLLGKKPVLDPKPFSLYRF (SEQ ID NO: 25) |
| Phenylalanine<br>hydroxylase<br>[Homo sapiens]<br>(Acc. No.<br>AAH26251] | MSTAVLENPGLGRKLSDFGQETSYIEDNCNQNGAISLIFSLKEEV<br>GALAKVLRLFEENDVNLTHIESRPSRLKKDEYEFFTHLDKRSLPA<br>LTNIIKILRHDIGATVHELSRDKKKDTVPWFPRTIQELDRFANQIL<br>SYGAELDADHPGFKDPVYRARRKQFADIAYNYRHGQPIPRVEY<br>MEEGKKTWGTVFKTLKSLYKTHACYEYNHIFPLLEKYCGFHED<br>NIPQLEDVSQFLQTCTGFRLRPVAGLLSSRDFLGGLAFRVFHCTQ<br>YIRHGSKPMYTPEPDICHELLGHVPLFSDRSFAQFSQEIGLASLGA |

TABLE 3-continued

Sequences of Exemplary Phenylalanine Metabolizing Enzymes

| Description | Sequence |
|---|---|
| | PDEYIEKLATIYWFTVEFGLCKQGDSIKAYGAGLLSSFGELQYCL SEKPKLLPLELEKTAIQNYTVTEFQPLYYVAESFNDAKEKVRNF AATIPRPFSVRYDPYTQRIEVLDNTQQLKILADSINSEIGILCSALQ KIK (SEQ ID NO: 26) |

In some embodiments, the mutant PAL is encoded by a PAL gene derived from wild-type *Photorhabdus luminescens* PAL, e.g., SEQ ID NO: 1. In some embodiments, the mutant PAL comprises mutations in one or more amino acid positions selected from 92, 133, 167, 432, 470, 433, 263, 366 and 396 compared to positions in wild type PAL, e.g., *Photorhabdus luminescens* PAL, e.g., SEQ ID NO: 1. In some embodiments, the mutant PAL comprises mutations in one or more amino acid positions selected from S92, H133, I167, L432, V470, A433, A263, K366, and/or L396 compared to positions in wild type PAL, e.g., *Photorhabdus luminescens* PAL, e.g., SEQ ID NO: 1. In some embodiments, the amino acid mutations are silent mutations, e.g., a change in the polynucleotide sequence without a corresponding change in the amino acid coding sequence. In some embodiments, the mutant PAL comprises mutations in one or more amino acid positions selected from S92G, H133M, H133F, I167K, L432I, V470A, A433S, A263T, K366K (e.g., silent mutation in polynucleotide sequence), and/or L396L (e.g., silent mutation in polynucleotide sequence) compared to positions in wild type PAL, e.g., *Photorhabdus luminescens* PAL, e.g., SEQ ID NO: 1.

In some embodiments, the mutant PAL comprises mutations in one or more amino acid positions selected from S92G, H133M, I167K, L432I, and V470A compared to positions in wild type PAL, e.g., *Photorhabdus luminescens* PAL, e.g., SEQ ID NO: 1. This mutant is referred to herein as "mPAL1" (SEQ ID NO: 2; Table 4).

In some embodiments, the mutant PAL comprises mutations in one or more amino acid positions selected from S92G, H133F, A433S, and V470A compared to positions in wild type PAL, e.g., *Photorhabdus luminescens* PAL, e.g., SEQ ID NO: 1. This mutant is referred to herein as "mPAL2" (SEQ ID NO: 3; Table 4).

In some embodiments, the mutant PAL comprises mutations in one or more amino acid positions selected from S92G, H133F, A263T, K366K (e.g., silent mutation in polynucleotide sequence), L396L (e.g., silent mutation in polynucleotide sequence), and V470A compared to positions in wild type PAL, e.g., *Photorhabdus luminescens* PAL, e.g., SEQ ID NO: 1. This mutant is referred to herein as "mPAL3" (SEQ ID NO: 4; Table 4).

TABLE 4

Sequences of Exemplary PAL Mutants

| Name | Amino Acid Sequence |
|---|---|
| *Photorhabdus luminescens* PAL3 Wild Type (SEQ ID NO: 1) | MKAKDVQPTIIINKNGLISLEDIYDIAIKQKKVEISTEITELLTHGRE KLEEKLNSGEVIYGINTGFGGNANLVVPFEKIAEHQQNLLTFLSAG TGDYMSKPCIKASQFTMLLSVCKGWSATRPIVAQAIVDHINHDIVP LVPRYGSVGASGDLIPLSYIARALCGIGKVYYMGAEIDAAEAIKRA GLTPLSLKAKEGLALINGTRVMSGISAITVIKLEKLFKASISAIALAV EALLASHEHYDARIQQVKNHPGQNAVASALRNLLAGSTQVNLLS GVKEQANKACRHQEITQLNDTLQEVYSIRCAPQVLGIVPESLATA RKILEREVISANDNPLIDPENGDVLHGGNFMGQYVARTMDALKLD IALIANHLHAIVALMMDNRFSRGLPNSLSPTPGMYQGFKGVQLSQ TALVAAIRHDCAASGIHTLATEQYNQDIVSLGLHAAQDVLEMEQK LRNIVSMTILVVCQAIHLRGNISEIAPETAKFYHAVREISSPLITDRA LDEDIIRIADAIINDQLPLPEIMLEE |
| mPAL1 (SEQ ID NO: 2) | MKAKDVQPTIIINKNGLISLEDIYDIAIKQKKVEISTEITELLTHGRE KLEEKLNSGEVIYGINTGFGGNANLVVPFEKIAEHQQNLLTFLGAG TGDYMSKPCIKASQFTMLLSVCKGWSATRPIVAQAIVDMINHDIV PLVPRYGSVGASGDLIPLSYIARALCGKGKVYYMGAEIDAAEEAIK RAGLTPLSLKAKEGLALINGTRVMSGISAITVIKLEKLFKASISAIAL AVEALLASHEHYDARIQQVKNHPGQNAVASALRNLLAGSTQVNL LSGVKEQANKACRHQEITQLNDTLQEVYSIRCAPQVLGIVPESLAT ARKILEREVISANDNPLIDPENGDVLHGGNFMGQYVARTMDALKL DIALIANHLHAIVALMMDNRFSRGLPNSLSPTPGMYQGFKGVQLS QTALVAAIRHDCAASGIHTIATEQYNQDIVSLGLHAAQDVLEMEQ KLRNIVSMTILVACQAIHLRGNISEIAPETAKFYHAVREISSPLITDR ALDEDIIRIADAIINDQLPLPEIMLEE |
| mPAL2 (SEQ ID NO: 3) | MKAKDVQPTIIINKNGLISLEDIYDIAIKQKKVEISTEITELLTHGRE KLEEKLNSGEVIYGINTGFGGNANLVVPFEKIAEHQQNLLTFLGAG TGDYMSKPCIKASQFTMLLSVCKGWSATRPIVAQAIVDFINHDIVP LVPRYGSVGASGDLIPLSYIARALCGIGKVYYMGAEIDAAEAIKRA GLTPLSLKAKEGLALINGTRVMSGISAITVIKLEKLFKASISAIALAV EALLASHEHYDARIQQVKNHPGQNAVASALRNLLAGSTQVNLLS GVKEQANKACRHQEITQLNDTLQEVYSIRCAPQVLGIVPESLATA RKILEREVISANDNPLIDPENGDVLHGGNFMGQYVARTMDALKLD IALIANHLHAIVALMMDNRFSRGLPNSLSPTPGMYQGFKGVQLSQ |

TABLE 4-continued

Sequences of Exemplary PAL Mutants

| Name | Amino Acid Sequence |
|---|---|
|  | TALVAAIRHDCAASGIHTLSTEQYNQDIVSLGLHAAQDVLEMEQK LRNIVSMTILVACQAIHLRGNISEIAPETAKFYHAVREISSPLITDRA LDEDIIRIADAIINDQLPLPEIMLEE |
| mPAL3 (SEQ ID NO: 4) | MKAKDVQPTIIINKNGLISLEDIYDIAIKQKKVEISTEITELLTHGRE KLEEKLNSGEVIYGINTGFGGNANLVVPFEKIAEHQQNLLTFLGAG TGDYMSKPCIKASQFTMLLSVCKGWSATRPIVAQAIVDFINHDIVP LVPRYGSVGASGDLIPLSYIARALCGIGKVYYMGAEIDAAEAIKRA GLTPLSLKAKEGLALINGTRVMSGISAITVIKLEKLFKASISAIALAV EALLASHEHYDARIQQVKNHPGQNAVASTLRNLLAGSTQVNLLS GVKEQANKACRHQEITQLNDTLQEVYSIRCAPQVLGIVPESLATA RKILEREVISANDNPLIDPENGDVLHGGNFMGQYVARTMDALKLD IALIANHLHAIVALMMDNRFSRGLPNSLSPTPGMYQGFKGVQLSQ TALVAAIRHDCAASGIHTLATEQYNQDIVSLGLHAAQDVLEMEQK LRNIVSMTILVACQAIHLRGNISEIAPETAKFYHAVREISSPLITDRA LDEDIIRIADAIINDQLPLPEIMLEE |

In some embodiments, the mutant PAL exhibits increased stability compared to wild type PAL, e.g., *P. luminescens* PAL. In some embodiments, the mutant PAL exhibits about 5%, 10%, 15%, 20%, 25%, 30%, 35%, 40%, 45%, 50%, 60%, 70%, 80%, 90% or more than 100% increased stability compared to wild type PAL, e.g., *P. luminescens* PAL. In some embodiments, the mutant PAL exhibits about two-, three-, four-, or five-fold increased stability compared to wild type PAL, e.g., *P. luminescens* PAL. In some embodiments, the mutant PAL exhibits increased activity or ability to metabolize phenylalanine and/or reduce hyperphenylalaninemia compared to a wild type PAL, e.g., *P. luminescens* PAL. In some embodiments, the mutant PAL exhibits about 5%, 10%, 15%, 20%, 25%, 30%, 35%, 40%, 45%, 50%, 60%, 70%, 80%, 90% or more than 100% increased activity or ability to metabolize phenylalanine and/or reduce hyperphenylalaninemia compared to wild type PAL, e.g., *P. luminescens* PAL. In some embodiments, the mutant PAL exhibits about two-, three-, four-, or five-fold increased activity or ability to metabolize phenylalanine and/or reduce hyperphenylalaninemia compared to wild type PAL, e.g., *P. luminescens* PAL. In some embodiments, the mutant PAL exhibits at least a two-fold increase in activity compared to wild type PAL, e.g., *Photorhabdus luminescens* PAL. In some embodiments, the mutant exhibits at least a three-fold increase in activity compared to the wild type PAL, e.g., *Photorhabdus luminescens* PAL. In some embodiments, the mutant exhibits at least a four-fold increase in activity compared to the wild type PAL, e.g., *Photorhabdus luminescens* PAL. In some embodiments, the mutant exhibits at least a five-fold increase in activity compared to the wild type PAL, e.g., *Photorhabdus luminescens* PAL. In some embodiments, the increase in PAL ability to metabolize phenylalanine is measured by detecting levels of phenylalanine, hippurate and/or transcinnamic acid in vitro or in vivo.

Gene Expression Systems

In some embodiments, a gene expression system comprises gene(s), e.g., encoding a mutant PAL polypeptide, together with one or more promoters, terminators, enhancers, insulators, silencers and other regulatory sequences to facilitate gene expression.

In some embodiments, the present disclosure provides gene expression systems comprising one or more copies of a gene encoding PAL, e.g., mutant PAL.

In some embodiments, the gene expression system comprises a mutant PAL derived from wild-type *Photorhabdus luminescens* PAL, e.g., SEQ ID NO: 1. In some embodiments, the gene expression system comprises a mutant PAL with mutations in one or more amino acid positions selected from 92, 133, 167, 432, 470, 433, 263, 366 and 396 compared to positions in wild type PAL, e.g., *Photorhabdus luminescens* PAL, e.g., SEQ ID NO: 1. In some embodiments, the gene expression system comprises a mutant PAL with mutations in one or more amino acid positions selected from S92, H133, I167, L432, V470, A433, A263, K366, and/or L396 compared to positions in wild type PAL, e.g., *Photorhabdus luminescens* PAL, e.g., SEQ ID NO: 1. In some embodiments, the gene expression system comprises a mutant PAL with mutations in one or more amino acid positions selected from 592G, H133F, H133M, I167K, L432I, V470A, A433S, A263T, K366K (e.g., silent mutation in polynucleotide sequence), and/or L396L (e.g., silent mutation in polynucleotide sequence) compared to positions in wild type PAL, e.g., *Photorhabdus luminescens* PAL, e.g., SEQ ID NO: 1.

In some embodiments, the gene expression system comprises a mutant PAL with mutations in one or more amino acid positions selected from 592G, H133M, I167K, L432I, and V470A compared to positions in wild type PAL, e.g., *Photorhabdus luminescens* PAL, e.g., SEQ ID NO: 1. In some embodiments, the gene expression system comprises a mutant PAL with mutations in one or more amino acid positions selected from S92G, H133F, A433S, and V470A compared to positions in wild type PAL, e.g., *Photorhabdus luminescens* PAL, e.g., SEQ ID NO: 1. In some embodiments, the gene expression system comprises a mutant PAL with mutations in one or more amino acid positions selected from S92G, H133F, A263T, K366K (e.g., silent mutation in polynucleotide sequence), L396L (e.g., silent mutation in polynucleotide sequence), and V470A compared to positions in wild type PAL, e.g., *Photorhabdus luminescens* PAL, e.g., SEQ ID NO: 1. In some embodiments, the gene expression system comprises mPAL1. In some embodiments, the gene expression system comprises mPAL2. In some embodiments, the gene expression system comprises mPAL3.

In some embodiments, the gene expression system comprises a mutant PAL and exhibits increased stability compared to a suitable control, e.g. a gene expression system comprising wild type PAL, e.g., *P. luminescens* PAL. In some embodiments, the gene expression system comprising the mutant PAL exhibits about 5%, 10%, 15%, 20%, 25%, 30%, 35%, 40%, 45%, 50%, 60%, 70%, 80%, 90% or more than 100% increased stability as compared to a suitable control, e.g. a gene expression system comprising wild type PAL, e.g., *P. luminescens* PAL. In some embodiments, the gene expression system comprising the mutant PAL exhibits about two-, three-, four-, or five-fold increased stability as compared to a suitable control, e.g. a gene expression system comprising wild type PAL, e.g., *P. luminescens* PAL. In some embodiments, the gene expression system comprises a mutant PAL and exhibits increased activity or ability to metabolize phenylalanine and/or reduce hyperphenylalaninemia compared to a suitable control, e.g. a gene expression system comprising a wild type PAL, e.g., *P. luminescens* PAL. In some embodiments, the gene expression system comprising the mutant PAL exhibits about 5%, 10%, 15%, 20%, 25%, 30%, 35%, 40%, 45%, 50%, 60%, 70%, 80%, 90% or more than 100% increased activity or ability to metabolize phenylalanine and/or reduce hyperphenylalaninemia as compared to a suitable control, e.g. a gene expression system comprising wild type PAL, e.g., *P. luminescens* PAL. In some embodiments, the gene expression system comprising the mutant PAL exhibits about two-, three-, four-, or five-fold increased activity or ability to metabolize phenylalanine and/or reduce hyperphenylalaninemia as compared to a suitable control, e.g. a gene expression system comprising wild type PAL, e.g., *P. luminescens* PAL. In some embodiments, the gene expression system comprises a mutant PAL and exhibits at least a two-fold increase in activity as compared to a suitable control, e.g. a gene expression system comprising wild type PAL, e.g., *Photorhabdus luminescens* PAL. In some embodiments, the gene expression system comprises a mutant PAL and exhibits at least a three-fold increase in activity as compared to a suitable control, e.g. a gene expression system comprising wild type PAL, e.g., *Photorhabdus luminescens* PAL. In some embodiments, the gene expression system comprises a mutant PAL and exhibits at least a four-fold increase in activity as compared to a suitable control, e.g. a gene expression system comprising wild type PAL, e.g., *Photorhabdus luminescens* PAL. In some embodiments, the gene expression system comprises a mutant PAL and exhibits at least a five-fold increase in activity as compared to a suitable control, e.g. a gene expression system comprising wild type PAL, e.g., *Photorhabdus luminescens* PAL.

In some embodiments, the gene expression system further comprises additional PME(s), e.g., PAH, LAAD. Exemplary PMEs and combinations thereof are known the in art, see, e.g., PCT/US2016/032562 and PCT/US2016/062369, the contents of which are hereby incorporated by reference. In some embodiments, the gene expression system comprises a mutant PAL and a wild type PAL.

In some embodiments, the gene expression system comprises one or more genes encoding a phenylalanine transporter, in addition to the one or more PMEs. In some embodiments, the phenylalanine transporter is encoded by a pheP gene derived from a bacterial species, including but not limited to, *Acinetobacter calcoaceticus*, *Salmonella enterica*, and *Escherichia coli*. Examples of phenylalanine transporters include Aageneral amino acid permease, encoded by the aroP gene, transports three aromatic amino acids, including phenylalanine, with high affinity, and is thought, together with PheP, responsible for the lion share of phenylalanine import. Additionally, a low level of phenylalanine transport activity has been traced to the activity of the LIV-I/LS system, which is a branched-chain amino acid transporter consisting of two periplasmic binding proteins, the LIV-binding protein (LIV-I system) and LS-binding protein (LS system), and membrane components, LivHMGF. In some embodiments, the phenylalanine transporter is encoded by an aroP gene derived from a bacterial species. In some embodiments, the phenylalanine transporter is encoded by LIV-binding protein and LS-binding protein and LivHMGF genes derived from a bacterial species. In some embodiments, the genetically engineered bacteria comprise more than one type of phenylalanine transporter, selected from pheP, aroP, and the LIV-I/LS system.

In some embodiments, the gene expression system comprises one or more genes encoding a transcriptional regulator, e.g., a transcription factor.

In some embodiments, the one or more PMEs and/or phenylalanine transporter and/or transcriptional regulator are operably linked to a promoter. In some embodiments, the promoter is a constitutive promoter. In some embodiments, the one or more PMEs and/or phenylalanine transporter and/or transcriptional regulator is operably linked to an inducible promoter. In some embodiments, the one or more PME and/or phenylalanine transporter and/or transcriptional regulator is under the control of a promoter that is induced by exogenous environmental conditions, as described herein. In some embodiments, the one or more PMEs and/or phenylalanine transporter and/or transcriptional regulator is in under the control of a promoter that is induced by exogenous environmental conditions, such as in the presence of molecules or metabolites specific to the gut of a mammal. In one embodiment, the one or more PMEs and/or phenylalanine transporter and/or transcriptional regulator is expressed under the control of a promoter that is induced by low-oxygen, microaerobic, or anaerobic conditions, wherein expression of the gene, is activated under low-oxygen or anaerobic environments, such as the environment of the mammalian gut. In some embodiments, the promoter is an FNR, an ANR, or a DNR promoter. Non-limiting examples of FNR promoter sequences are provided in Table 2. In other embodiments, one or more PME(s) and/or phenylalanine transporter and/or transcriptional regulator are expressed under the control of an oxygen level-dependent promoter fused to a binding site for a transcriptional activator, e.g., CRP. CRP (cyclic AMP receptor protein or catabolite activator protein or CAP) plays a major regulatory role in bacteria by repressing genes responsible for the uptake, metabolism, and assimilation of less favorable carbon sources when rapidly metabolizable carbohydrates, such as glucose, are present (Wu et al., 2015).

In alternate embodiments, the one or more PMEs and/or phenylalanine transporter and/or transcriptional regulator is under the control of a $P_{araBAD}$ promoter, which is activated in the presence of the sugar arabinose. In one embodiment, LAAD expression is under the control of the $P_{araBAD}$ promoter. In one embodiment, expression of LAAD occurs under aerobic or microaerobic conditions. In one embodiment, PAL expression is under the control of the $P_{araBAD}$ promoter. In one embodiment, PAL expression occurs under aerobic or microaerobic conditions. In one embodiment, PAL expression occurs under anaerobic or low oxygen conditions and LAAD expression occurs under aerobic or microaerobic conditions. In one embodiment, PAL expression occurs under anaerobic or low oxygen conditions and LADD expression is under the control of the $P_{araBAD}$ promoter. In some embodiments, the one or more PMEs and/or phenylalanine transporter gene are expressed under the control of a promoter that is induced by exposure to a chemical and/or nutritional inducer. In some embodiments, the one or more PMEs and/or phenylalanine transporter and/or transcriptional regulator gene are expressed under the control of a promoter that is induced by exposure to tetracycline. In some embodiments, the one or more PMEs and/or phenylalanine transporter and/or transcriptional regulator gene are expressed under the control of a promoter that is induced by exposure to arabinose. In some embodiments the one or more PMEs and/or phenylalanine transporter and/or transcriptional regulator gene are expressed under the control of a promoter that is induced by exposure to IPTG or other LacI inducer. In some embodiments, the one or more PMEs and/or phenylalanine transporter and/or transcriptional regulator gene are expressed under the control of a promoter that is induced by exposure to rhamnose. In some embodiments, the one or more PMEs and/or phenylalanine transporter and/or transcriptional regulator gene are expressed under the control of a promoter that is induced by exposure to teracycline. In some embodiments, more than one PME gene is expressed, e.g., PAL and LAAD gene, and each gene is expressed under the control of different promoters, such as any of the promoters discussed herein.

In some embodiments, the gene expression system comprises one or more gene sequence(s) whose expression is controlled by a temperature sensitive mechanism. Thermoregulators are advantageous because of strong transcriptional control without the use of external chemicals or specialized media (see, e.g., Nemani et al., Magnetic nanoparticle hyperthermia induced cytosine deaminase expression in microencapsulated *E. coli* for enzyme-prodrug therapy; J Biotechnol. 2015 Jun. 10; 203: 32-40, and references therein). Thermoregulated protein expression using the mutant cI857 repressor and the pL and/or pR phage 2 promoters have been used to engineer recombinant bacterial strains. The gene of interest cloned downstream of the 2 promoters can then be efficiently regulated by the mutant thermolabile cI857 repressor of bacteriophage 2. At temperatures below 37° C., cI857 binds to the oL or oR regions of the pR promoter and blocks transcription by RNA polymerase. At higher temperatures, e.g. 37-42° C., the functional cI857 dimer is destabilized, binding to the oL or oR DNA sequences is abrogated, and mRNA transcription is initiated. Inducible expression from the ParaBad can be controlled or further fine-tuned through the optimization of the ribosome binding site (RBS), as described herein.

In one embodiment, expression of the one or more PME(s) and/or Phe transporter, e.g., PheP, and/or transcriptional regulator(s), is driven by one or more thermoregulated promoter(s). In one embodiment, expression of PAL is driven by a thermoregulated promoter. In one embodiment, expression of PheP is driven by a thermoregulated promoter. In one embodiment, expression of LAAD is driven by a thermoregulated promoter.

In some embodiments, more than one PME gene is expressed, e.g., PAL and LAAD gene, and each gene is expressed under the control of the same promoter, such as any of the promoters discussed herein. In some embodiments, the PME gene(s) and/or phenylalanine transporter gene and/or transcriptional regulator are expressed under the control of different promoters, such as any of the promoters discussed herein. In some embodiments, the PME gene(s) and/or phenylalanine transporter gene and/or transcriptional regulator are expressed under the control of the same promoter, such as any of the promoters discussed herein.

In another embodiment, one or more inducible promoter(s), e.g., thermoregulated, arabinose-inducible, tet-inducible, and IPTG-inducible promoters, drive the expression of one or more bicistronic message(s). Bicistronic messages may include one or more PME(s), e.g. PAL or LAAD, and/or one or more Phe transporter(s) e.g., PheP, and/or one or more transcriptional regulator(s). In one embodiment, one or more inducible promoter(s) drive the expression of tri-cistronic messages. Tri-cistronic messages may include one or more PME(s), e.g. PAL or LAAD, and/or one or more Phe transporter(s) e.g., PheP, and/or one or more transcriptional regulator(s). In one embodiment, one or more inducible promoter(s) drive the expression of multi-cistronic messages. Multi-cistronic messages induced may include one or more PME(s), e.g. PAL or LAAD, and/or one or more Phe transporter(s) e.g., PheP, and/or one or more transcriptional regulator(s).

In some embodiments, the gene expression system may also comprise one or more gene sequences relating to biosafety and/or biocontainment, e.g., a kill-switch, gene guard system, and/or auxotrophy. The expression of these gene sequence(s) may be regulated using the promoters or promoter systems described herein. The promoter may be the same promoter to regulate one or more different genes, may be a different copy of the same promoter to regulate different genes, or may involve the use of different promoters used in combination to regulate the expression of different genes. The use of different regulatory or promoter systems to control gene expression provides flexibility (e.g., the ability to differentially control gene expression under different environmental conditions and/or the ability to differentially control gene expression temporally) and also provides the ability to "fine-tune" gene expression, any or all of which regulation may serve to optimize gene expression and/or growth of the microorganism. Examples and combinations are known the in art, see, e.g., PCT/US2016/032562 and PCT/US2016/062369, the contents of which are hereby incorporated by reference.

Microorganisms Engineered to Reduce Hyperphenylalaninemia

The genetically engineered microorganisms capable of reducing excess phenylalanine are provided herein. In some embodiments, the genetically engineered microorganisms are bacteria. In some embodiments, the bacteria are non-pathogenic bacteria. In some embodiments, the bacteria are commensal bacteria. In some embodiments, the bacteria are probiotic bacteria. In some embodiments, the genetically engineered bacteria are naturally pathogenic bacteria that are modified or mutated to reduce or eliminate pathogenicity. In some embodiments, non-pathogenic bacteria are Gram-negative bacteria. In some embodiments, non-pathogenic bacteria are Gram-positive bacteria. Exemplary bacteria include, but are not limited to, *Bacillus, Bacteroides, Bifidobacterium, Brevibacteria, Clostridium, Enterococcus, Escherichia coli, Lactobacillus, Lactococcus, Saccharomyces*, and *Staphylococcus*, e.g., *Bacillus coagulans, Bacillus subtilis, Bacteroides fragilis, Bacteroides subtilis, Bacteroides thetaiotaomicron, Bifidobacterium bifidum, Bifidobacterium infantis, Bifidobacterium lactis, Bifidobacterium longum, Clostridium butyricum, Enterococcus faecium, Lactobacillus acidophilus, Lactobacillus bulgaricus, Lactobacillus casei, Lactobacillus johnsonii, Lactobacillus paracasei, Lactobacillus plantarum, Lactobacillus reuteri, Lactobacillus rhamnosus, Lactococcus lactis*, and *Saccharomyces boulardii*. In certain embodiments, the genetically engineered bacteria are selected from the group consisting of *Bacteroides fragilis, Bacteroides thetaiotaomicron, Bacteroides subtilis, Bifidobacterium bifidum, Bifidobacterium infantis, Bifidobacterium lactis, Clostridium butyricum, Escherichia coli* Nissle, *Lactobacillus acidophilus, Lactobacillus plantarum, Lactobacillus reuteri*, and *Lactococcus lactis*.

In some embodiments, the genetically engineered bacteria are *Escherichia coli* strain Nissle 1917 (*E. coli* Nissle), a Gram-negative bacterium of the Enterobacteriaceae family that has evolved into one of the best characterized probiotics (Ukena et al., 2007). The strain is characterized by its complete harmlessness (Schultz, 2008), and has GRAS (generally recognized as safe) status (Reister et al., 2014, emphasis added).

One of ordinary skill in the art would appreciate that the genetic modifications disclosed herein may be adapted for other species, strains, and subtypes of bacteria. Furthermore, genes from one or more different species can be introduced into one another, e.g., the PAL gene from Rhodosporidium toruloides can be expressed in *Escherichia coli* (Sarkissian et al., 1999), and it is known that prokaryotic and eukaryotic phenylalanine ammonia lyases share sequence homology (Xiang and Moore, 2005).

Unmodified *E. coli* Nissle and the genetically engineered bacteria of the invention may be destroyed, e.g., by defense factors in the gut or blood serum (Sonnenbom et al., 2009) or by activation of a kill switch, several hours or days after administration. Thus, the genetically engineered bacteria may require continued administration. In some embodiments, the residence time is calculated for a human subject. Residence time in vivo may be calculated for the genetically engineered bacteria.

In some embodiments, the genetically engineered microorganisms, e.g., bacteria, comprise one or more gene(s) encoding PAL, e.g., mutant PAL. In some embodiments, the genetically engineered microorganisms, e.g., bacteria, comprise a PAL derived from a prokaryotic species. In some embodiments, the genetically engineered microorganisms, e.g., bacteria, comprise a PAL derived from a eukaryotic species. In some embodiments, the genetically engineered microorganisms, e.g., bacteria, comprise a PAL derived from a bacterial species, including but not limited to, *Achromobacter xylosoxidans, Pseudomonas aeruginosa, Photorhabdus luminescens, Anabaena variabilis,* and *Agrobacterium tumefaciens*.

In some embodiments, the genetically engineered microorganisms, e.g., bacteria, comprise a mutant PAL derived from wild-type *Photorhabdus luminescens* PAL, e.g., SEQ ID NO: 1. In some embodiments, the genetically engineered microorganisms, e.g., bacteria, comprise a mutant PAL with mutations in one or more amino acid positions selected from 92, 133, 167, 432, 470, 433, 263, 366 and 396 compared to positions in wild type PAL, e.g., *Photorhabdus luminescens* PAL, e.g., SEQ ID NO: 1. In some embodiments, the genetically engineered microorganisms, e.g., bacteria, comprise a mutant PAL with mutations in one or more amino acid positions selected from S92, H133, I167, L432, V470, A433, A263, K366, and/or L396 compared to positions in wild type PAL, e.g., *Photorhabdus luminescens* PAL, e.g., SEQ ID NO: 1. In some embodiments, the genetically engineered microorganisms, e.g., bacteria, comprise a mutant PAL with mutations in one or more amino acid positions selected from S92G, H133M, H133F, I167K, L432I, V470A, A433S, A263T, K366K (e.g., silent mutation in polynucleotide sequence), and/or L396L (e.g., silent mutation in polynucleotide sequence) compared to positions in wild type PAL, e.g., *Photorhabdus luminescens* PAL, e.g., SEQ ID NO: 1.

In some embodiments, the genetically engineered microorganisms, e.g., bacteria, comprise a mutant PAL with mutations in one or more amino acid positions selected from S92G, H133M, I167K, L432I, and V470A compared to positions in wild type PAL, e.g., *Photorhabdus luminescens* PAL, e.g., SEQ ID NO: 1. In some embodiments, the genetically engineered microorganisms, e.g., bacteria, comprise a mutant PAL with mutations in one or more amino acid positions selected from 592G, H133F, A433S, and V470A compared to positions in wild type PAL, e.g., *Photorhabdus luminescens* PAL, e.g., SEQ ID NO: 1. In some embodiments, the genetically engineered microorganisms, e.g., bacteria, comprise a mutant PAL with mutations in one or more amino acid positions selected from S92G, H133F, A263T, K366K (e.g., silent mutation in polynucleotide sequence), L396L (e.g., silent mutation in polynucleotide sequence), and V470A compared to positions in wild type PAL, e.g., *Photorhabdus luminescens* PAL, e.g., SEQ ID NO: 1. In some embodiments, the genetically engineered microorganisms, e.g., bacteria, comprise mPAL1. In some embodiments, the genetically engineered microorganisms, e.g., bacteria, comprise mPAL2. In some embodiments, the genetically engineered microorganisms, e.g., bacteria, comprise mPAL3.

In some embodiments, the genetically engineered microorganisms, e.g., bacteria, comprise a mutant PAL and exhibit increased stability compared to a suitable control, e.g. a genetically engineered microorganism, e.g. bacteria, comprising wild type PAL, e.g., *P. luminescens* PAL. In some embodiments, the genetically engineered microorganism, e.g. bacteria, comprising the mutant PAL exhibits about 5%, 10%, 15%, 20%, 25%, 30%, 35%, 40%, 45%, 50%, 60%, 70%, 80%, 90% or more than 100% increased stability as compared to a suitable control, e.g. a genetically engineered microorganism, e.g. bacteria, comprising wild type PAL, e.g., *P. luminescens* PAL. In some embodiments, the genetically engineered microorganism, e.g. bacteria, comprising the mutant PAL exhibits about two-, three-, four-, or five-fold increased stability as compared to a suitable control, e.g. a genetically engineered microorganism, e.g. bacteria, comprising wild type PAL, e.g., *P. luminescens* PAL. In some embodiments, the genetically engineered microorganism, e.g. bacteria, comprises a mutant PAL and exhibits increased activity or ability to metabolize phenylalanine and/or reduce hyperphenylalaninemia as compared to a suitable control, e.g. a genetically engineered microorganism, e.g. bacteria, comprising wild type PAL, e.g., *P. luminescens* PAL. In some embodiments, the genetically engineered microorganism, e.g. bacteria, comprising the mutant PAL exhibits about 5%, 10%, 15%, 20%, 25%, 30%, 35%, 40%, 45%, 50%, 60%, 70%, 80%, 90% or more than 100% increased activity or ability to metabolize phenylalanine and/or reduce hyperphenylalaninemia as compared to a suitable control, e.g. a genetically engineered microorganism, e.g. bacteria, comprising wild type PAL, e.g., *P. luminescens* PAL. In some embodiments, the genetically engineered microorganism, e.g. bacteria, comprising the mutant PAL exhibits about two-, three-, four-, or five-fold increased activity or ability to metabolize phenylalanine and/or reduce hyperphenylalaninemia as compared to a suitable control, e.g. a genetically engineered microorganism, e.g. bacteria, comprising wild type PAL, e.g., *P. luminescens* PAL. In some embodiments, the genetically engineered microorganisms, e.g., bacteria, comprise a mutant PAL and exhibits at least a two-fold increase in activity as compared to a suitable control, e.g. a genetically engineered microorganism, e.g. bacteria, comprising wild type PAL, e.g., *Photorhabdus luminescens* PAL. In some embodiments, the genetically engineered microorganisms, e.g., bacteria, comprise a mutant PAL and exhibits at least a three-fold increase in activity as compared to a suitable control, e.g. a genetically engineered microorganism, e.g. bacteria, comprising the wild type PAL, e.g., *Photorhabdus luminescens* PAL. In some embodiments, the genetically engineered microorganisms, e.g., bacteria, comprise a mutant PAL and exhibits at least a four-fold increase in activity as compared to a suitable control, e.g. a genetically engineered microorganism, e.g. bacteria, comprising wild type PAL, e.g., *Photorhabdus luminescens* PAL. In some embodiments, the genetically engineered microorganisms, e.g., bacteria, comprise a mutant PAL and exhibits at least a five-fold increase in activity as compared to a suitable control, e.g. a genetically engineered microorganism, e.g. bacteria, comprising wild type PAL, e.g., *Photorhabdus luminescens* PAL.

In some embodiments, the genetically engineered microorganisms, e.g., bacteria, comprise additional PME(s), e.g., PAH, LAAD. Exemplary PMEs and combinations thereof are known the in art, see, e.g., PCT/US2016/032562 and PCT/US2016/062369, the contents of which are hereby incorporated by reference. In some embodiments, the genetically engineered microorganisms, e.g., bacteria, comprise a mutant PAL and a wild type PAL.

In some embodiments, the genetically engineered microorganisms, e.g., bacteria, comprise a mutant PAL as described herein and a phenylalanine transporter as described herein, e.g., PheP. In some embodiments, the genetically engineered microorganisms, e.g., bacteria, comprise a mutant PAL as described herein, a LAAD as described herein, and a phenylalanine transporter as described herein, e.g., PheP.

In some embodiments, the genetically engineered microorganisms, e.g., bacteria, comprise a transcriptional regulator, e.g., a non-native transcriptional regulator as described herein.

In these embodiments, the PME, e.g., mutant PAL, phenylalanine transporter, and/or transcriptional regulator present in the genetically engineered microorganism, e.g. bacteria, may be operably linked to one or more promoters. The promoters may be the same or different for each gene or each copy of each gene. In some embodiments, the promoter is a constitutive promoter or an inducible promoter. In some embodiments, the promoter is induced by exogenous environmental conditions. In some embodiments, the promoter is induced by exogenous environmental conditions, such as in the presence of molecules or metabolites specific to the gut of a mammal. In some embodiments, the promoter is induced by low-oxygen, microaerobic, or anaerobic conditions, wherein expression of the gene, is activated under low-oxygen or anaerobic environments, such as the environment of the mammalian gut. In some embodiments, the promoter is an FNR, an ANR, or a DNR promoter. In some embodiments, the oxygen level-dependent promoter is fused to a binding site for a transcriptional activator, e.g., CRP. In some embodiments, the promoter is a $P_{araBAD}$ promoter, which is activated in the presence of the sugar arabinose. In one embodiment, LAAD expression is under the control of the $P_{araBAD}$ promoter. In one embodiment, expression of LAAD occurs under aerobic or microaerobic conditions. In one embodiment, PAL expression is under the control of the $P_{araBAD}$ promoter. In one embodiment, PAL expression occurs under aerobic or microaerobic conditions. In one embodiment, PAL expression occurs under anaerobic or low oxygen conditions and LAAD expression occurs under aerobic or microaerobic conditions. In one embodiment, PAL expression occurs under anaerobic or low oxygen conditions and LAAD expression is under the control of the $P_{araBAD}$ promoter. In some embodiments, the one or more PME and/or phenylalanine transporter and/or transcriptional regulator gene is expressed under the control of a promoter that is induced by exposure to a chemical and/or nutritional inducer. In some embodiments, the one or more PMEs and/or phenylalanine transporter and/or transcriptional regulator gene is expressed under the control of a promoter that is induced by exposure to tetracycline. In some embodiments, the one or more PMEs and/or phenylalanine transporter gene and/or transcriptional regulator is expressed under the control of a promoter that is induced by exposure to arabinose. In some embodiments the one or more PMEs and/or phenylalanine transporter gene and/or transcriptional regulator is expressed under the control of a promoter that is induced by exposure to IPTG or other LacI inducer. In some embodiments, the one or more PMEs and/or phenylalanine transporter and/or transcriptional regulator gene is expressed under the control of a promoter that is induced by exposure to rhamnose. In some embodiments, the one or more PMEs and/or phenylalanine transporter and/or transcriptional regulator gene is expressed under the control of a promoter that is induced by exposure to teracycline. In some embodiments, more than one PME gene is expressed, e.g., PAL and LAAD gene, and each gene is expressed under the control of different promoters, such as any of the promoters discussed herein.

In some embodiments, the PME, e.g., mutant PAL, phenylalanine transporter, and/or transcriptional regulator expression is controlled by a temperature sensitive mechanism, e.g., the mutant cI857 repressor, the pL and/or pR phage promoters. In some embodiments, at temperatures below 37° C., cI857 binds to the oL or oR regions of the pR promoter and blocks transcription by RNA polymerase. At higher temperatures, e.g. 37-42° C., the functional cI857 dimer is destabilized, binding to the oL or oR DNA sequences is abrogated, and mRNA transcription is initiated. Inducible expression from the ParaBad can be controlled or further fine-tuned through the optimization of the ribosome binding site (RBS), as described herein.

In one embodiment, expression of one or more PME(s), and/or Phe transporter(s), e.g., PheP, and/or transcriptional regulator(s), in the genetically engineered microorganisms, e.g., bacteria, is driven by one or more thermoregulated promoter(s). In one embodiment, expression of PAL is driven by a thermoregulated promoter. In one embodiment, expression of PheP is driven by a thermoregulated promoter. In one embodiment, expression of LAAD is driven by a thermoregulated promoter.

In some embodiments, more than one PME gene is expressed in the genetically engineered microorganisms, e.g., bacteria, and each gene is expressed under the control of the same promoter, such as any of the promoters discussed herein. In some embodiments, more than one PME gene is expressed in the genetically engineered microorganisms, e.g., bacteria, and each gene is expressed under the control of the same promoter, such as any of the promoters discussed herein. In some embodiments, the PME gene(s) and/or phenylalanine transporter and/or transcriptional regulator gene in the genetically engineered microorganisms, e.g., bacteria is expressed under the control of different promoters, such as any of the promoters discussed herein. In some embodiments, the PME gene(s) and/or phenylalanine transporter and/or transcriptional regulator gene in the genetically engineered microorganisms, e.g., bacteria is expressed under the control of the same promoter, such as any of the promoters discussed herein.

In another embodiment, one or more inducible promoter(s), e.g., thermoregulated, arabinose-inducible, tet-inducible, and IPTG-inducible promoters, in the genetically engineered microorganisms, e.g., bacteria drive the expression of one or more bicistronic message(s). Bicistronic messages may include one or more PME(s), e.g. PAL or LAAD, and/or one or more Phe transporter(s) e.g., PheP, and/or one or more transcriptional regulator(s). In one embodiment, one or more inducible promoter(s) drive the expression of tri-cistronic messages. Tri-cistronic messages may include one or more PME(s), e.g. PAL or LAAD, and/or one or more Phe transporter(s) e.g., PheP, and/or one or more transcriptional regulator(s). In one embodiment, one or more inducible promoter(s) drive the expression of multi-cistronic messages. Multi-cistronic messages induced may include one or more PME(s), e.g. PAL or LAAD, and/or one or more Phe transporter(s) e.g., PheP, and/or one or more transcriptional regulator(s).

The one or more PMEs, phenylalanine transporter and transcriptional regulator gene(s) may be present on a plasmid or chromosome in the genetically engineered microorganism, e.g. bacteria. In some embodiments, expression from the chromosome may be useful for increasing stability of expression of the PME and/or phenylalanine transporter and/or transcriptional regulator. In some embodiments, the one or more PME and/or phenylalanine transporter and/or transcriptional regulator gene(s) is integrated into the chromosome of the microorganism at one or more integration sites in the genetically engineered microorganism. In some embodiments, the one or more PME and/or phenylalanine transporter and/or transcriptional regulator gene(s) is expressed on a plasmid. In some embodiments, the plasmid is a low copy plasmid. In other embodiments, the plasmid is a high copy plasmid.

In some embodiments, the genetically engineered microorganism, e.g., bacteria, may also comprise one or more gene sequences relating to biosafety and/or biocontainment, e.g., a kill-switch, gene guard system, essential gene for cell growth and/or survival, thyA, dapA, and/or auxotrophy. The expression of these gene sequence(s) may be regulated using the promoters or promoter systems described herein. The promoter may be the same promoter to regulate one or more different genes, may be a different copy of the same promoter to regulate different genes, or may involve the use of different promoters used in combination to regulate the expression of different genes. The use of different regulatory or promoter systems to control gene expression provides flexibility (e.g., the ability to differentially control gene expression under different environmental conditions and/or the ability to differentially control gene expression temporally) and also provides the ability to "fine-tune" gene expression, any or all of which regulation may serve to optimize gene expression and/or growth of the microorganism. Examples and combinations are known the in art, see, e.g., PCT/US2016/032562 and PCT/US2016/062369, U.S. Provisional Application No. 62/184,811, PCT/US2016/062369, the contents of which are hereby incorporated by reference.

In some embodiments, the genetically engineered microorganisms further comprise a native secretion mechanism or non-native secretion mechanism that is capable of secreting a molecule from the cytoplasm in the extracellular environment. Many microorganisms have evolved sophisticated secretion systems to transport substrates across the ell envelope. Substrates, such as small molecules, proteins, and DNA, may be released into the extracellular space or periplasm (such as the gut lumen or other space), injected into a target cell, or associated with the membrane of the microorganism. Examples of secretion systems are disclosed in PCT/US2016/062369.

In some embodiments, wherein the genetically engineered microorganism is a bacterium, the disclosure provides a bacterium comprising one or more phage genome(s), wherein one or more of the phage genomes are defective. In some embodiments, the disclosure provides a bacterium comprising one or more phage genome(s), wherein one or more of the phage genomes are defective such that lytic phage is not produced. In some embodiments, the disclosure provides a bacterium comprising one or more phage genome(s), wherein one or more of the phage genomes are defective in that one or more phage genes are not expressed. In some embodiments, the disclosure provides a bacterium comprising one or more phage genome(s), wherein one or more phage genes in the one or more phage genome(s) comprise one or more mutations. In some embodiments, the one or more phage genome(s) are present in the natural state of the probiotic bacterium. In some embodiments, the bacteria encode one or more lysogenic phage(s). In some embodiments, the bacteria encode one or more defective or cryptic phage(s) or satellite phage(s). In some embodiments, the bacteria encode one or more tailiocins or gene transfer agents. In some embodiments, the one or more mutations affect the ability of the phage to undergo the lytic cycle, e.g., reduce the frequency or reduce the number of bacteria in a given population that can undergo the lytic stage. In some embodiments, the one or more mutations prevent the phage from infecting other bacteria. In some embodiments, the one or more mutations alters, e.g., increases or reduces, bacterial fitness.

In some embodiments, one or more of the phage genomes of the genetically engineered bacteria are mutated. Such mutations may include one or more deletion(s) of a part of or the complete sequence of one or more phage genes. Alternatively, the mutations may include one or more insertion(s) of one or more nucleotides into one or more phage genes. In another example, the mutations may include one or more substitution(s) of a part of or the complete sequence of one or more phage genes. In another example, the mutations include one or more inversion(s) of a part of or the complete sequence of one or more phage genes in the phage genome. Additionally, the mutations may include any combination of one or more deletions, insertions, substitutions or inversions. In certain embodiments, the one or more mutations reduce or prevent the production and release of phage particles from the bacterium relative to the same bacterium not having the one or more targeted mutations in the one or more phage genomes. In some embodiments, the bacterium is *Escherichia coli* strain Nissle. In some embodiments, the phage genome which is mutated is *E. coli* Nissle Phage 1 genome, the *E. coli* Nissle Phage 2 genome and/or the *E. coli* Nissle Phage 3 genome. In one embodiment, the mutated phage genome is the *E. coli* Nissle Phage 3 genome. In one embodiment, the mutations are located in or comprise one or more genes selected from ECOLIN_09965, ECOLIN_09970, ECOLIN_09975, ECOLIN_09980, ECOLIN_09985, ECOLIN_09990, ECOLIN_09995, ECOLIN_10000, ECOLIN_10005, ECOLIN_10010, ECOLIN_10015, ECOLIN_10020, ECOLIN_10025, ECOLIN_10030, ECOLIN_10035, ECOLIN_10040, ECOLIN_10045, ECOLIN_10050, ECOLIN_10055, ECOLIN_10065, ECOLIN_10070, ECOLIN_10075, ECOLIN_10080, ECOLIN_10085, ECOLIN_10090, ECOLIN_10095, ECOLIN_10100, ECOLIN_10105, ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, ECOLIN_10175, ECOLIN_10180, ECOLIN_10185, ECOLIN_10190, ECOLIN_10195, ECOLIN_10200, ECOLIN_10205, ECOLIN_10210, ECOLIN_10220, ECOLIN_10225, ECOLIN_10230, ECOLIN_10235, ECOLIN_10240, ECOLIN_10245, ECOLIN_10250, ECOLIN_10255, ECOLIN_10260, ECOLIN_10265, ECOLIN_10270, ECOLIN_10275, ECOLIN_10280, ECOLIN_10290, ECOLIN_10295, ECOLIN_10300, ECOLIN_10305, ECOLIN_10310, ECOLIN_10315, ECOLIN_10320, ECOLIN_10325, ECOLIN_10330, ECOLIN_10335, ECOLIN_10340, and ECOLIN_10345. In one embodiment, the mutations, e.g., one or more deletions, are located in or comprise one or more genes selected from ECOLIN_10110, ECOLIN_10115, ECOLIN_10120, ECOLIN_10125, ECOLIN_10130, ECOLIN_10135, ECOLIN_10140, ECOLIN_10145, ECOLIN_10150, ECOLIN_10160, ECOLIN_10165, ECOLIN_10170, and ECOLIN_10175. pharmaceutically acceptable composition comprising the bacterium disclosed herein and a pharmaceutically acceptable carrier.

Modifications of phage genomes are known in the art, see, e.g., PCT/US18/38840, the contents of which are hereby incorporated by reference.

In some embodiments, the mutations are located within or encompass one or more genes encoding lytic genes. In some embodiments, the mutations are located within or encompass one or more genes encoding one or more proteases or lysins. In some embodiments, the mutations are located within or encompass one or more genes encoding one or more toxins. In some embodiments, the mutations are located within or encompass one or more genes encoding one or more antibiotic resistance related proteins. In some embodiments, the mutations are located within or encompass one or more genes encoding one or phage translation related proteins. In some embodiments, the one or more mutations are located within or encompass one or more genes encoding structural proteins. Such structural genes include genes encoding polypeptides of the head, tail, collar, or coat. In some embodiments, the one or more mutations are located within or encompass one or more genes encoding polypeptides of the head structure. In some embodiments, the one or more mutations are located within or encompass one or more genes encoding polypeptides of the tail structure. In some embodiments, the one or more mutations are located within or encompass one or more genes encoding polypeptides of the collar structure. In some embodiments, the one or more mutations are located within or encompass one or more genes encoding tail proteins. In some embodiments, the one or more mutations are located within or encompass one or more genes encoding polypeptides of the coat structure. In some embodiments, the mutations are located within or encompass one or more genes encoding one or more plate proteins. In some embodiments, the mutations are located within or encompass one or more genes encoding one or more proteins require for assembly of the bacteriophage. In some embodiments, the mutations are located within or encompass one or more genes encoding one or more portal proteins. In some embodiments, the mutations are located within or encompass one or more genes encoding one or more polypeptides involved in recombination. In some embodiments, the mutations are located within or encompass one or more genes encoding one or more integrases. In some embodiments, the mutations are located within or encompass one or more genes encoding one or more invertases. In some embodiments, the mutations are located within or encompass one or more genes encoding one or more transposases. In some embodiments, the mutations are located with within or encompass one or more genes encoding one or more polypeptides involved in replication or translation. In some embodiments, the mutations are located within or encompass one or more genes encoding one or more primases. In some embodiments, the mutations are located within or encompass one or more genes encoding one or more tRNA related proteins. In some embodiments, the mutations are located within or encompass one or more genes encoding one or more polypeptides involved in phage insertion. In some embodiments, the mutations are located within or encompass one or more genes encoding an attachment site. In some embodiments, the mutations are located within or encompass one or more genes encoding one or more polypeptides involved in packaging. In some embodiments, the mutations are located within or encompass one or more genes encoding one or more terminases. In some embodiments, the mutations are located within or encompass one or more genes encoding one or more tailiocins. In some embodiments, the mutations are located within one or more genes associated with lytic growth, horizontal gene transfer, cell lysis, phage structure, phage assembly, phage packaging, recombination, replication, translation, phage insertion, or combinations thereof. In some embodiments, the mutations are located within or encompass one or more genes encoding one or more host genes. In some embodiments, the mutation is in a gene encoding lipid A biosynthesis (KDO)2-(lauroyl)-lipid IVA acyltransferase, peptidase, zinc ABC transporter substrate-binding protein, zinc ABC transporter ATPase, high-affinity zinc transporter membrane component, ATP-dependent DNA helicase RuvB, ATP-dependent DNA helicase RuvA, Holliday junction resolvase, dihydroneopterin triphosphate pyrophosphatase, aspartyl-tRNA synthetase, hydrolase, DNA polymerase V, MsgA, phage tail protein, tail protein, host specificity protein, peptidase P60, tail protein, tail fiber protein, Minor tail protein U, DNA breaking-rejoining protein, peptidase S14, capsid protein, DNA packaging protein, terminase, lysozyme, holin, DNA adenine methylase, serine protease, antitermination protein, antirepressor, crossover junction endodeoxyribonuclease, adenine methyltransferase, DNA methyltransferase ECOLIN_10240, GntR family transcriptional regulator ECOLIN_10245, cI repressor, Domain of unknown function (DUF4222); DNA recombinase, Multiple Antibiotic Resistance Regulator (MarR), unknown ead like protein in P22, Protein of unknown function (DUF550); 3'-5' exonuclease, excisionase, integrase, tRNA methyltransferase, and combinations thereof.

In some embodiments, the mutations are located within or encompass genes encoding one or more polypeptides involved in one or more of cell lysis, phage structure, phage assembly, phage packaging recombination, replication or translation, phage insertion, or are host proteins, and combinations thereof.

In some embodiments, described herein genetically engineered bacteria are engineered *Escherichia coli* strain Nissle 1917. Bioinformatics assessment, as described in PCT/US2018/038840, which is incorporated in herein by reference in its entirety, uncovered three high-confidence, predicted prophage sequences in the *E. coli* Nissle genome, referred herein to as Phage 1, Phage 2, and Phage 3. The longest predicted phage in *E. coli* Nissle (Phage 3) contains a total of 68 proteins, and includes a phage tail, head, portal, terminase, lysin, capsid, and integrase, all of which appear to be intact. Phage 2 contains a total of 69 proteins, and includes phage transposase, lysis, terminase, head, portal, capsid, and tail proteins. Closer inspection of Phage 2 revealed that the int/xis gene pair have been disrupted by a mobile genetic element, and that the cI repressor has been fragmented into separate DNA-binding and sensing peptides, which would be expected to prevent induction of this phage. The shortest of the intact phages predicted in *E. coli* Nissle, Phage 1, contains a total of 32 proteins, and includes lysis and transposase functionality. However, the absence of many structural genes within the putative prophage element termed Phage 1 calls into question its potential to release viable phage particles. In some embodiments, the genetically engineered bacteria comprise one or more *E. coli* Nissle bacteriophage, e.g., Phage 1, Phage 2, and Phage 3. In some embodiments, the genetically engineered bacteria comprise Phage 3 of *E. coli* Nissle bacteriophage. PCT/US18/38840, the contents of which are hereby incorporated by reference, provides genes of exemplary phage.

Pharmaceutical Compositions

Pharmaceutical compositions comprising the genetically engineered microorganisms, e.g., the genetically engineered bacteria comprising mutant PAL, disclosed herein may be used to treat, manage, ameliorate, and/or prevent diseases associated with hyperphenylalaninemia, e.g., PKU. Pharmaceutical compositions of the invention comprising one or more genetically engineered microorganisms, alone or in combination with prophylactic agents, therapeutic agents, and/or and pharmaceutically acceptable carriers are provided. In certain embodiments, the pharmaceutical composition comprises one species, strain, or subtype of microorganism that are engineered to comprise the genetic modifications described herein. In alternate embodiments, the pharmaceutical composition comprises two or more species, strains, and/or subtypes of microorganism that are each engineered to comprise the genetic modifications described herein.

The pharmaceutical compositions described herein may be formulated in a conventional manner using one or more physiologically acceptable carriers comprising excipients and auxiliaries, which facilitate processing of the active ingredients into compositions for pharmaceutical use. Methods of formulating pharmaceutical compositions are known in the art (see, e.g., "Remington's Pharmaceutical Sciences," Mack Publishing Co., Easton, Pa.). In some embodiments, the pharmaceutical compositions are subjected to tabletting, lyophilizing, direct compression, conventional mixing, dissolving, granulating, levigating, emulsifying, encapsulating, entrapping, or spray drying to form tablets, granulates, nanoparticles, nanocapsules, microcapsules, microtablets, pellets, or powders, which may be enterically coated or uncoated. Appropriate formulation depends on the route of administration.

The genetically engineered microorganisms described herein may be formulated into pharmaceutical compositions in any suitable dosage form (e.g., liquids, capsules, sachet, hard capsules, soft capsules, tablets, enteric coated tablets, suspension powders, granules, or matrix sustained release formations for oral administration) and for any suitable type of administration (e.g., oral, topical, injectable, immediate-release, pulsatile-release, delayed-release, or sustained release). In some embodiments, the genetically engineered microorganism is a bacterium. Suitable dosage amounts for the genetically engineered bacteria may range from about $10^5$ to $10^{12}$ bacteria, e.g., approximately $10^5$ bacteria, approximately $10^6$ bacteria, approximately $10^7$ bacteria, approximately $10^8$ bacteria, approximately $10^9$ bacteria, approximately $10^{10}$ bacteria, approximately $10^{11}$ bacteria, or approximately $10^{11}$ bacteria. The composition may be administered once or more daily, weekly, or monthly. The composition may be administered before, during, or following a meal. In one embodiment, the pharmaceutical composition is administered before the subject eats a meal. In one embodiment, the pharmaceutical composition is administered currently with a meal. In one embodiment, the pharmaceutical composition is administered after the subject eats a meal.

The genetically engineered microorganisms may be formulated into pharmaceutical compositions comprising one or more pharmaceutically acceptable carriers, thickeners, diluents, buffers, buffering agents, surface active agents, neutral or cationic lipids, lipid complexes, liposomes, penetration enhancers, carrier compounds, and other pharmaceutically acceptable carriers or agents. For example, the pharmaceutical composition may include, but is not limited to, the addition of calcium bicarbonate, sodium bicarbonate, calcium phosphate, various sugars and types of starch, cellulose derivatives, gelatin, vegetable oils, polyethylene glycols, and surfactants, including, for example, polysorbate 20. In some embodiments, the genetically engineered microorganisms of the invention may be formulated in a solution of sodium bicarbonate, e.g., 1 molar solution of sodium bicarbonate (to buffer an acidic cellular environment, such as the stomach, for example). The genetically engineered microorganisms may be administered and formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The genetically engineered microorganisms disclosed herein may be administered topically and formulated in the form of an ointment, cream, transdermal patch, lotion, gel, shampoo, spray, aerosol, solution, emulsion, or other form well-known to one of skill in the art. See, e.g., "Remington's Pharmaceutical Sciences," Mack Publishing Co., Easton, Pa. In an embodiment, for non-sprayable topical dosage forms, viscous to semi-solid or solid forms comprising a carrier or one or more excipients compatible with topical application and having a dynamic viscosity greater than water are employed. Suitable formulations include, but are not limited to, solutions, suspensions, emulsions, creams, ointments, powders, liniments, salves, etc., which may be sterilized or mixed with auxiliary agents (e.g., preservatives, stabilizers, wetting agents, buffers, or salts) for influencing various properties, e.g., osmotic pressure. Other suitable topical dosage forms include sprayable aerosol preparations wherein the active ingredient in combination with a solid or liquid inert carrier, is packaged in a mixture with a pressurized volatile (e.g., a gaseous propellant, such as freon) or in a squeeze bottle. Moisturizers or humectants can also be added to pharmaceutical compositions and dosage forms. Examples of such additional ingredients are well known in the art. In one embodiment, the pharmaceutical composition comprising the recombinant microorganism of the invention may be formulated as a hygiene product. For example, the hygiene product may be an antimicrobial formulation, or a fermentation product such as a fermentation broth. Hygiene products may be, for example, shampoos, conditioners, creams, pastes, lotions, and lip balms.

The genetically engineered microorganisms disclosed herein may be administered orally and formulated as tablets, pills, dragees, capsules, liquids, gels, syrups, slurries, suspensions, etc. Pharmacological compositions for oral use can be made using a solid excipient, optionally grinding the resulting mixture, and processing the mixture of granules, after adding suitable auxiliaries if desired, to obtain tablets or dragee cores. Suitable excipients include, but are not limited to, fillers such as sugars, including lactose, sucrose, mannitol, or sorbitol; cellulose compositions such as maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP) or polyethylene glycol (PEG). Disintegrating agents may also be added, such as cross-linked polyvinylpyrrolidone, agar, alginic acid or a salt thereof such as sodium alginate.

Tablets or capsules can be prepared by conventional means with pharmaceutically acceptable excipients such as binding agents (e.g., pregelatinised maize starch, polyvinylpyrrolidone, hydroxypropyl methylcellulose, carboxymethylcellulose, polyethylene glycol, sucrose, glucose, sorbitol, starch, gum, kaolin, and tragacanth); fillers (e.g., lactose, microcrystalline cellulose, or calcium hydrogen phosphate); lubricants (e.g., calcium, aluminum, zinc, stearic acid, polyethylene glycol, sodium lauryl sulfate, starch, sodium benzoate, L-leucine, magnesium stearate, talc, or silica); disintegrants (e.g., starch, potato starch, sodium starch glycolate, sugars, cellulose derivatives, silica powders); or wetting agents (e.g., sodium lauryl sulphate). The tablets may be coated by methods well known in the art. A coating shell may be present, and common membranes include, but are not limited to, polylactide, polyglycolic acid, polyanhydride, other biodegradable polymers, alginate-polylysine-alginate (APA), alginate-polymethylene-co-guanidine-alginate (A-PMCG-A), hydroymethylacrylate-methyl methacrylate (HEMA-MMA), multilayered HEMA-MMA-MAA, polyacrylonitrilevinylchloride (PAN-PVC), acrylonitrile/sodium methallylsulfonate (AN-69), polyethylene glycol/poly pentamethylcyclopentasiloxane/polydimethylsiloxane (PEG/PD5/PDMS), poly N,N-dimethyl acrylamide (PDMAAm), siliceous encapsulates, cellulose sulphate/sodium alginate/polymethylene-co-guanidine (CS/A/PMCG), cellulose acetate phthalate, calcium alginate, k-carrageenan-locust bean gum gel beads, gellan-xanthan beads, poly(lactide-co-glycolides), carrageenan, starch poly-anhydrides, starch polymethacrylates, polyamino acids, and enteric coating polymers.

In some embodiments, the genetically engineered microorganisms are enterically coated for release into the gut or a particular region of the gut, for example, the large intestine. The typical pH profile from the stomach to the colon is about 1-4 (stomach), 5.5-6 (duodenum), 7.3-8.0 (ileum), and 5.5-6.5 (colon). In some diseases, the pH profile may be modified. In some embodiments, the coating is degraded in specific pH environments in order to specify the site of release. In some embodiments, at least two coatings are used. In some embodiments, the outside coating and the inside coating are degraded at different pH levels.

Liquid preparations for oral administration may take the form of solutions, syrups, suspensions, or a dry product for constitution with water or other suitable vehicle before use. Such liquid preparations may be prepared by conventional means with pharmaceutically acceptable agents such as suspending agents (e.g., sorbitol syrup, cellulose derivatives, or hydrogenated edible fats); emulsifying agents (e.g., lecithin or acacia); non-aqueous vehicles (e.g., almond oil, oily esters, ethyl alcohol, or fractionated vegetable oils); and preservatives (e.g., methyl or propyl-p-hydroxybenzoates or sorbic acid). The preparations may also contain buffer salts, flavoring, coloring, and sweetening agents as appropriate. Preparations for oral administration may be suitably formulated for slow release, controlled release, or sustained release of the genetically engineered microorganisms described herein.

In certain embodiments, the genetically engineered microorganisms may be orally administered, for example, with an inert diluent or an assimilable edible carrier. The compound may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound by other than parenteral administration, it may be necessary to coat the compound with, or co-administer the compound with, a material to prevent its inactivation.

In another embodiment, the pharmaceutical composition comprising the recombinant microorganisms of the invention may be a comestible product, for example, a food product. In one embodiment, the food product is milk, concentrated milk, fermented milk (yogurt, sour milk, frozen yogurt, lactic acid bacteria-fermented beverages), milk powder, ice cream, cream cheeses, dry cheeses, soybean milk, fermented soybean milk, vegetable-fruit juices, fruit juices, sports drinks, confectionery, candies, infant foods (such as infant cakes), nutritional food products, animal feeds, or dietary supplements. In one embodiment, the food product is a fermented food, such as a fermented dairy product. In one embodiment, the fermented dairy product is yogurt. In another embodiment, the fermented dairy product is cheese, milk, cream, ice cream, milk shake, or kefir. In another embodiment, the recombinant microorganism of the invention are combined in a preparation containing other live bacterial cells intended to serve as probiotics. In another embodiment, the food product is a beverage. In one embodiment, the beverage is a fruit juice-based beverage or a beverage containing plant or herbal extracts. In another embodiment, the food product is a jelly or a pudding. Other food products suitable for administration of the recombinant microorganisms of the invention are well known in the art. See, e.g., US 2015/0359894 and US 2015/0238545, the entire contents of each of which are expressly incorporated herein by reference. In yet another embodiment, the pharmaceutical composition of the invention is injected into, sprayed onto, or sprinkled onto a food product, such as bread, yogurt, or cheese.

In some embodiments, the composition is formulated for intraintestinal administration, intrajejunal administration, intraduodenal administration, intraileal administration, gastric shunt administration, or intracolic administration, via nanoparticles, nanocapsules, microcapsules, or microtablets, which are enterically coated or uncoated. The pharmaceutical compositions may also be formulated in rectal compositions such as suppositories or retention enemas, using, e.g., conventional suppository bases such as cocoa butter or other glycerides. The compositions may be suspensions, solutions, or emulsions in oily or aqueous vehicles, and may contain suspending, stabilizing and/or dispersing agents.

The genetically engineered microorganisms described herein may be administered intranasally, formulated in an aerosol form, spray, mist, or in the form of drops, and conveniently delivered in the form of an aerosol spray presentation from pressurized packs or a nebuliser, with the use of a suitable propellant (e.g., dichlorodifluoromethane, trichlorofluoromethane, dichlorotetrafluoroethane, carbon dioxide or other suitable gas). Pressurized aerosol dosage units may be determined by providing a valve to deliver a metered amount. Capsules and cartridges (e.g., of gelatin) for use in an inhaler or insufflator may be formulated containing a powder mix of the compound and a suitable powder base such as lactose or starch.

The genetically engineered microorganisms may be administered and formulated as depot preparations. Such long acting formulations may be administered by implantation or by injection, including intravenous injection, subcutaneous injection, local injection, direct injection, or infusion. For example, the compositions may be formulated with suitable polymeric or hydrophobic materials (e.g., as an emulsion in an acceptable oil) or ion exchange resins, or as sparingly soluble derivatives (e.g., as a sparingly soluble salt).

In some embodiments, disclosed herein are pharmaceutically acceptable compositions in single dosage forms. Single dosage forms may be in a liquid or a solid form. Single dosage forms may be administered directly to a patient without modification or may be diluted or reconstituted prior to administration. In certain embodiments, a single dosage form may be administered in bolus form, e.g., single injection, single oral dose, including an oral dose that comprises multiple tablets, capsule, pills, etc. In alternate embodiments, a single dosage form may be administered over a period of time, e.g., by infusion.

In other embodiments, the composition can be delivered in a controlled release or sustained release system. In one embodiment, a pump may be used to achieve controlled or sustained release. In another embodiment, polymeric materials can be used to achieve controlled or sustained release of the therapies of the present disclosure (see, e.g., U.S. Pat. No. 5,989,463). Examples of polymers used in sustained release formulations include, but are not limited to, poly(-hydroxy ethyl methacrylate), poly(methyl methacrylate), poly(acrylic acid), poly(ethylene-co-vinyl acetate), poly (methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. The polymer used in a sustained release formulation may be inert, free of leachable impurities, stable on storage, sterile, and biodegradable. In some embodiments, a controlled or sustained release system can be placed in proximity of the prophylactic or therapeutic target, thus requiring only a fraction of the systemic dose. Any suitable technique known to one of skill in the art may be used.

Dosage regimens may be adjusted to provide a therapeutic response. Dosing can depend on several factors, including severity and responsiveness of the disease, route of administration, time course of treatment (days to months to years), and time to amelioration of the disease. For example, a single bolus may be administered at one time, several divided doses may be administered over a predetermined period of time, or the dose may be reduced or increased as indicated by the therapeutic situation. The specification for the dosage is dictated by the unique characteristics of the active compound and the particular therapeutic effect to be achieved. Dosage values may vary with the type and severity of the condition to be alleviated. For any particular subject, specific dosage regimens may be adjusted over time according to the individual need and the professional judgment of the treating clinician. Toxicity and therapeutic efficacy of compounds provided herein can be determined by standard pharmaceutical procedures in cell culture or animal models. For example, $LD_{50}$, $ED_{50}$, $EC_{50}$, and $IC_{50}$ may be determined, and the dose ratio between toxic and therapeutic effects ($LD_{50}/ED_{50}$) may be calculated as the therapeutic index. Compositions that exhibit toxic side effects may be used, with careful modifications to minimize potential damage to reduce side effects. Dosing may be estimated initially from cell culture assays and animal models. The data obtained from in vitro and in vivo assays and animal studies can be used in formulating a range of dosage for use in humans.

The pharmaceutical compositions may be packaged in a hermetically sealed container such as an ampoule or sachet indicating the quantity of the agent. In one embodiment, one or more of the pharmaceutical compositions is supplied as a dry sterilized lyophilized powder or water-free concentrate in a hermetically sealed container and can be reconstituted (e.g., with water or saline) to the appropriate concentration for administration to a subject. In an embodiment, one or more of the prophylactic or therapeutic agents or pharmaceutical compositions is supplied as a dry sterile lyophilized powder in a hermetically sealed container stored between 2° C. and 8° C. and administered within 1 hour, within 3 hours, within 5 hours, within 6 hours, within 12 hours, within 24 hours, within 48 hours, within 72 hours, or within one week after being reconstituted. Cryoprotectants can be included for a lyophilized dosage form, principally 0-10% sucrose (optimally 0.5-1.0%). Other suitable cryoprotectants include trehalose and lactose. Other suitable bulking agents include glycine and arginine, either of which can be included at a concentration of 0-0.05%, and polysorbate-80 (optimally included at a concentration of 0.005-0.01%). Additional surfactants include but are not limited to polysorbate 20 and BRIJ surfactants. The pharmaceutical composition may be prepared as an injectable solution and can further comprise an agent useful as an adjuvant, such as those used to increase absorption or dispersion, e.g., hyaluronidase.

Methods of Treatment

Another aspect of the disclosure provides methods of treating a disease associated with hyperphenylalaninemia or symptom(s) associated with hyperphenylalaninemia. In some embodiments, the disclosure provides a method for treating a disease associated with hyperphenylalaninemia or symptom(s) associated with hyperphenylalaninemia comprising administering to a subject in need thereof a composition comprising an engineered microorganism, e.g., bacteria, disclosed herein. In some embodiments, the disclosure provides a method for treating a disease associated with hyperphenylalaninemia or symptom(s) associated with hyperphenylalaninemia comprising administering to a subject in need thereof a composition comprising an engineered microorganism comprising gene sequence encoding one or more PMEs, e.g., PAL including mutant PAL, PAH, and/or LAAD.

In some embodiments, the method of treatment comprises administering a microorganism, e.g., bacterium, comprising a mutant PAL derived from wild-type *Photorhabdus luminescens* PAL, e.g., SEQ ID NO: 1. In some embodiments, the method of treatment comprises administering a microorganism, e.g., bacterium, comprising a mutant PAL with mutations in one or more amino acid positions selected from 92, 133, 167, 432, 470, 433, 263, 366 and 396 compared to positions in wild type PAL, e.g., *Photorhabdus luminescens* PAL, e.g., SEQ ID NO: 1. In some embodiments, the method of treatment comprises administering a microorganism, e.g., bacterium, comprising a mutant PAL with mutations in one or more amino acid positions selected from S92, H133, I167, L432, V470, A433, A263, K366, and/or L396 compared to positions in wild type PAL, e.g., *Photorhabdus luminescens* PAL, e.g., SEQ ID NO: 1. In some embodiments, the method of treatment comprises administering a microorganism, e.g., bacterium, comprising a mutant PAL with mutations in one or more amino acid positions selected from S92G, H133M, H133F, I167K, L432I, V470A, A433S, A263T, K366K (e.g., silent mutation in polynucleotide sequence), and/or L396L (e.g., silent mutation in polynucleotide sequence) compared to positions in wild type PAL, e.g., *Photorhabdus luminescens* PAL, e.g., SEQ ID NO: 1.

In some embodiments, the method of treatment comprises administering a microorganism, e.g., bacterium, comprising a mutant PAL with mutations in one or more amino acid positions selected from S92G, H133M, I167K, L432I, and V470A compared to positions in wild type PAL, e.g., *Photorhabdus luminescens* PAL, e.g., SEQ ID NO: 1. In some embodiments, the method of treatment comprises administering a microorganism, e.g., bacterium, comprising a mutant PAL with mutations in one or more amino acid positions selected from S92G, H133F, A433S, and V470A compared to positions in wild type PAL, e.g., *Photorhabdus luminescens* PAL, e.g., SEQ ID NO: 1. In some embodiments, the method of treatment comprises administering a microorganism, e.g., bacterium, comprising a mutant PAL with mutations in one or more amino acid positions selected from S92G, H133F, A263T, K366K (e.g., silent mutation in polynucleotide sequence), L396L (e.g., silent mutation in polynucleotide sequence), and V470A compared to positions in wild type PAL, e.g., *Photorhabdus luminescens* PAL, e.g., SEQ ID NO: 1.

In some embodiments, the method of treatment comprises administering a microorganism, e.g., bacterium, comprising mPAL1. In some embodiments, the method of treatment comprises administering a microorganism, e.g., bacterium, comprising mPAL2. In some embodiments, the method of treatment comprises administering a microorganism, e.g., bacterium, comprising mPAL3.

In some embodiments, the method of treatment comprises administering a microorganism, e.g., bacterium, comprising a mutant PAL that exhibits increased stability compared to wild type PAL, e.g., *P. luminescens* PAL. In some embodiments, the method of treatment comprises administering a microorganism, e.g., bacterium, comprising a mutant PAL that exhibits increased activity or ability to metabolize phenylalanine and/or reduce hyperphenylalaninemia compared to a wild type PAL, e.g., *P. luminescens* PAL. In some embodiments, the method of treatment comprises administering a microorganism, e.g., bacterium, comprising a mutant PAL that exhibits at least a two-fold increase in activity compared to wild type PAL, e.g., *Photorhabdus luminescens* PAL. In some embodiments, the method of treatment comprises administering a microorganism, e.g., bacterium, comprising a mutant PAL that exhibits at least a three-fold increase in activity compared to the wild type PAL, e.g., *Photorhabdus luminescens* PAL. In some embodiments, the method of treatment comprises administering a microorganism, e.g., bacterium, comprising a mutant PAL that exhibits at least a four-fold increase in activity compared to the wild type PAL, e.g., *Photorhabdus luminescens* PAL. In some embodiments, the method of treatment comprises administering a microorganism, e.g., bacterium, comprising a mutant PAL that exhibits at least a five-fold increase in activity compared to the wild type PAL, e.g., *Photorhabdus luminescens* PAL.

In some embodiments, the method of treatment comprises administering a microorganism, e.g., bacterium, further comprising additional PME(s), e.g., PAH, LAAD, and/or phenylalanine transporter(s). Exemplary PMEs and combinations thereof are known the in art, see, e.g., PCT/US2016/032562 and PCT/US2016/062369, the contents of which are hereby incorporated by reference. In some embodiments, the method of treatment comprises administering a microorganism, e.g., bacterium, comprising a mutant PAL and a wild type PAL.

In some embodiments, the method of treatment comprises administering a microorganism, e.g., bacterium, further comprising a transcriptional regulator, e.g., a non-native transcriptional regulator as described herein. In these embodiments, the PME, e.g., mutant PAL, phenylalanine transporter, and/or transcriptional regulator may be operably linked to one or more promoters as disclosed herein, e.g., a constitutive promoter, an inducible promoter, a thermoregulated promoter, an oxygen-level dependent promoter, etc.

In some embodiments, the genetically engineered microorganism, e.g., bacteria, may also comprise one or more gene sequences relating to biosafety and/or biocontainment as described herein, e.g., a kill-switch, gene guard system, essential gene for cell growth and/or survival, thyA, dapA, auxotrophy, etc.

In some embodiments, the disease is selected from the group consisting of: phenylketonuria, classical or typical phenylketonuria, atypical phenylketonuria, permanent mild hyperphenylalaninemia, nonphenylketonuric hyperphenylalaninemia, phenylalanine hydroxylase deficiency, cofactor deficiency, dihydropteridine reductase deficiency, tetrahydropterin synthase deficiency, and Segawa's disease. In some embodiments, hyperphenylalaninemia is secondary to other conditions, e.g., liver diseases. In some embodiments, the invention provides methods for reducing, ameliorating, or eliminating one or more symptom(s) associated with these diseases, including but not limited to neurological deficits, mental retardation, encephalopathy, epilepsy, eczema, reduced growth, microcephaly, tremor, limb spasticity, and/or hypopigmentation. In some embodiments, the subject to be treated is a human patient.

In certain embodiments, the genetically engineered microorganisms are capable of metabolizing phenylalanine in the diet in order to treat a disease or disorder associated with hyperphenylalaninemia, e.g., PKU. In some embodiments, the genetically engineered microorganisms are delivered simultaneously with dietary protein. In other embodiments, the genetically engineered bacteria are not delivered simultaneously with dietary protein. Studies have shown that pancreatic and other glandular secretions into the intestine contain high levels of proteins, enzymes, and polypeptides, and that the amino acids produced as a result of their catabolism are reabsorbed back into the blood in a process known as "enterorecirculation" (Chang, 2007; Sarkissian et al., 1999). Thus, high intestinal levels of phenylalanine may be partially independent of food intake, and are available for breakdown by PAL. In some embodiments, the genetically engineered microorganisms and dietary protein are delivered after a period of fasting or phenylalanine-restricted dieting. In these embodiments, a patient suffering from hyperphenylalaninemia may be able to resume a substantially normal diet, or a diet that is less restrictive than a phenylalanine-free diet. In some embodiments, the genetically engineered microorganisms may be capable of metabolizing phenylalanine from additional sources, e.g., the blood, in order to treat a disease associated with hyperphenylalaninemia, e.g., PKU. In these embodiments, the genetically engineered microorganisms need not be delivered simultaneously with dietary protein, and a phenylalanine gradient is generated, e.g., from blood to gut, and the genetically engineered microorganisms metabolize phenylalanine and reduce hyperphenylalaninemia.

The method may comprise preparing a pharmaceutical composition with at least one genetically engineered species, strain, or subtype of microorganism, e.g., bacterium, described herein, and administering the pharmaceutical composition to a subject in a therapeutically effective amount. In some embodiments, the genetically engineered microorganisms of the invention are administered orally, e.g., in a liquid suspension. In some embodiments, the genetically engineered microorganisms of the invention are lyophilized in a gel cap and administered orally. In some embodiments, the genetically engineered microorganisms of the invention are administered via a feeding tube or gastric shunt. In some embodiments, the genetically engineered microorganism of the invention are administered rectally, e.g., by enema. In some embodiments, the genetically engineered microorganisms of the invention are administered topically, intraintestinally, intrajejunally, intraduodenally, intraileally, and/or intracolically.

In certain embodiments, the pharmaceutical composition described herein is administered to reduce phenylalanine levels in a subject. In some embodiments, the methods of the present disclosure reduce the phenylalanine levels in a subject by at least about 10%, 20%, 25%, 30%, 40%, 50%, 60%, 70%, 75%, 80%, 85%, 90%, 95%, or more as compared to levels in an untreated or control subject. In some embodiments, reduction is measured by comparing the phenylalanine level in a subject before and after administration of the pharmaceutical composition. In some embodiments, the method of treating or ameliorating hyperphenylalaninemia allows one or more symptoms of the condition or disorder to improve by at least about 10%, 20%, 30%, 40%, 50%, 60%, 70%, 80%, 90%, 95%, or more.

Before, during, and after the administration of the pharmaceutical composition, phenylalanine levels in the subject may be measured in a biological sample, such as blood, serum, plasma, urine, peritoneal fluid, cerebrospinal fluid, fecal matter, intestinal mucosal scrapings, a sample collected from a tissue, and/or a sample collected from the contents of one or more of the following: the stomach, duodenum, jejunum, ileum, cecum, colon, rectum, and anal canal. In some embodiments, the methods may include administration of the compositions of the invention to reduce phenylalanine. In some embodiments, the methods may include administration of the compositions of the invention to reduce phenylalanine to undetectable levels in a subject. In some embodiments, the methods may include administration of the compositions of the invention to reduce phenylalanine concentrations to undetectable levels, or to less than about 1%, 2%, 5%, 10%, 20%, 25%, 30%, 40%, 50%, 60%, 70%, 75%, or 80% of the subject's phenylalanine levels prior to treatment.

Hippurate levels in the subject may be measured in a biological sample, such as blood, serum, plasma, urine, peritoneal fluid, cerebrospinal fluid, fecal matter, intestinal mucosal scrapings, a sample collected from a tissue, and/or a sample collected from the contents of one or more of the following: the stomach, duodenum, jejunum, ileum, cecum, colon, rectum, and anal canal. In some embodiments, the methods described herein may include administration of the compositions of the invention to reduce phenylalanine and resulting in increased levels of hippurate production. In some embodiments, the methods may include administration of the compositions of the invention to reduce phenylalanine to undetectable levels in a subject, and concurrently and proportionately increase hippurate levels, e.g., in the urine. In some embodiments, the methods may include administration of the compositions of the invention, leading to an increase hippurate concentrations to more than about 1%, 2%, 5%, 10%, 20%, 25%, 30%, 40%, 50%, 60%, 70%, 75%, 80%, 90%, 95%, or up to 99% or up to 100% of the subject's urine hippurate levels prior to treatment.

In some embodiments, the activity (e.g., phenylalanine degrading activity) of genetically engineered microorganism expressing PAL, e.g., mutant PAL, can be detected in the urine of a mammalian subject, e.g., an animal model or a human, by measuring the amounts of hippurate produced and the rate of its accumulation. Hippurate is a PAL specific breakdown product, and is normally present in human urine at low concentrations. It is the end product of metabolism of phenylalanine via the PAL pathway. Phenylalanine ammonia lyase mediates the conversion of phenylalanine to cinnamate. When cinnamate is produced in the gut, is absorbed and quickly converted to hippurate in the liver and excreted in the liver (Hoskins JA and Gray Phenylalanine ammonia lyase in the management of phenylketonuria: the relationship between ingested cinnamate and urinary hippurate in humans. J Res Commun Chem Pathol Pharmacol. 1982 February; 35(2):275-82). Phenylalanine is converted to hippurate in a 1:1 ratio, i.e., 1 mole of Phe is converted into 1 mol of hippurate. Thus, changes in urinary hippurate levels can be used as a non-invasive measure of the effect of therapies that utilize this mechanism.

Hippuric acid thus has the potential to function as a biomarker allowing monitoring of dietary adherence and treatment effect in patients receiving PAL-based regimens. It can be used as an adjunct to measurement of blood Phe levels in the management of patients and because it is a urinary biomarker, it can have advantages particularly in children to adjust protein intake-which can be challenging as needs vary based on growth.

In this section, the term "PAL-based drug" refers to any drug, polypeptide, biologic, or treatment regimen that has PAL activity, for example, PEG-PAL, Kuvan, a composition comprising a microorganism of the present disclosure, e.g., microorganism encoding PAL and optionally PheP transporter. In some embodiments, the disclosure provides a method for measuring PAL activity in vivo by administering to a subject, e.g., a mammalian subject, a PAL-based drug and measuring the amount of hippurate produced in the subject as a measure of PAL activity. In some embodiments, the disclosure provides a method for monitoring the therapeutic activity of a PAL-based drug by administering to a subject, e.g., a mammalian subject, the PAL-based drug and measuring the amount of hippurate produced in the subject as a measure of PAL therapeutic activity. In some embodiments, the disclosure provides a method for adjusting the dosage of a PAL-based drug by administering to a subject, e.g., a mammalian subject, the PAL-based drug, measuring the amount of hippurate produced in the subject to determine PAL activity, and adjusting (e.g., increasing or decreasing) the dosage of the drug to increase or decrease the PAL activity in the subject. In some embodiments, the disclosure provides a method for adjusting the protein intake and/or diet of a subject having hyperphenylalaninemia comprising administering to the subject a PAL-based drug, measuring the amount of hippurate produced in the subject, and adjusting (e.g., increasing or decreasing) the protein intake or otherwise adjusting the diet of the subject to increase or decrease the PAL activity in the subject. In some embodiments, the disclosure provides a method for confirming adherence to a protein intake and/or diet regimen of a subject having hyperphenylalaninemia comprising administering to the subject a PAL-based drug, measuring the amount of hippurate produced in the subject, and measuring PAL activity in the subject.

In some embodiments of the methods disclosed herein, both blood phenylalanine levels and urine hippurate levels are monitored in a subject. In some embodiments, blood phenylalanine and hippurate in the urine are measured at multiple time points, to determine the rate of phenylalanine breakdown. In some embodiments, hippurate levels in the urine are used evaluate PAL activity or strain activity in animal models.

In some embodiments, hippuric acid measurements in the urine, alone or in combination with blood phenylalanine measurements, are used to the strain prove mechanism of action. In some embodiments, hippuric acid measurements in the urine, alone or in combination with blood phenylalanine measurements, are used as a tool to differentiate between PAL and LAAD activity in a strain, and allow to determine the contribution of each enzyme to the overall strain activity.

In some embodiments, hippuric acid measurements in the urine, alone or in combination with blood phenylalanine measurements, are used evaluate safety in animal models and human subjects. In some embodiments, hippuric acid measurements in the urine, alone or in combination with blood phenylalanine measurements, are used in the evaluation of dose-response and optimal regimen for the desired pharmacologic effect and safety. In some embodiments, hippuric acid measurements in the urine, alone or in combination with blood phenylalanine measurements, are used as surrogate endpoint for efficacy and/or toxicity. In some embodiments, hippuric acid measurements in the urine, alone or in combination with blood phenylalanine measurements, are used to predict patients' response to a regimen comprising a therapeutic strain. In some embodiments, hippuric acid measurements in the urine, alone or in combination with blood phenylalanine measurements, are used for the identification of certain patient populations that are more likely to respond to the drug therapy. In some embodiments, hippuric acid measurements in the urine, alone or in combination with blood phenylalanine measurements, are used to avoid specific adverse events. In some embodiments, hippuric acid measurements in the urine, alone or in combination with blood phenylalanine measurements, are useful for patient selection.

In some embodiments, hippuric acid measurements in the urine, alone or in combination with blood phenylalanine measurements, are used as one method for adjusting protein intake/diet of PKU patient on a regimen which includes the administration of a therapeutic PKU strain expressing PAL.

In some embodiments, measurement of urine levels of hippuric acid, alone or in combination with blood phenylalanine measurements, is used to measure and/or monitor the activity of recombinant PAL. In some embodiments, measurement of urine levels of hippuric acid is used to measure and/or monitor the activity of recombinant pegylated PAL (Peg-PAL). In some embodiments, measurement of urine levels of hippuric acid, alone or in combination with blood phenylalanine measurements, is used to measure and/or monitor the activity of recombinant PAL administered in combination with a therapeutic strain as described herein.

In some embodiments, hippuric acid measurements in the urine, alone or in combination with blood phenylalanine measurements, are used in combination with other biomarkers, e.g., clinical safety biomarkers. Non-limiting examples of such safety markers include physical examination, vital signs, and electrocardiogram (ECG). Other non-limiting examples include liver safety tests known in the art, e.g., serum aspartate transaminase (AST), alanine transaminase (ALT), alkaline phosphatase (ALP), gamma-glutamyl transferase (GGT), and bilirubin. Such biosafety markers also include renal safety tests, e.g., those known in the art, e.g., blood urea nitrogen (BUN), serum creatinine, glomerular filtration rate (GFR), creatinine clearance, serum electrolytes (sodium, potassium, chloride, and bicarbonate), and complete urine analysis (color, pH, specific gravity, glucose, proteins, ketone bodies, and microscopic exam for blood, leukocytes, casts), as well as Cystatin-c, β2-microglobulin, uric acid, clusterin, N-acetyl-beta-dglucosaminidase, neutrophil gelatinase-associated lipocalin (NGAL), N-acetyl-β-dglucosaminidase (NAG), and kidney injury molecule-1 (KIM-1). Other non-limiting examples include Hematology safety biomarkers known in the art, e.g., Complete blood count, total hemoglobin, hematocrit, red cell count, mean red cell volume, mean cell hemoglobin, red cell distribution width %, mean cell hemoglobin concentration, total white cell count, differential white cell count (Neutrophils, lymphocytes, basophils, esinophils, and monocytes), and platelets. Other no-liming examples include bone safety markers known in the art, e.g., Serum calcium and inorganic phosphates. Other non-limiting examples include basic metabolic safety biomarkers known in the art, e.g., blood glucose, triglycerides (TG), total cholesterol, low density lipoprotein cholesterol (LDLc), and high density lipoprotein cholesterol (HDL-c). Other specific safety biomarkers known in the art include, e.g., serum immunoglobulin levels, C-reactive protein (CRP), fibrinogen, thyroid stimulating hormone (TSH), thyroxine, testosterone, insulin, lactate dehydrogenase (LDH), creatine kinase (CK) and its isoenzymes, cardiac troponin (cTn), and methemoglobin.

The methods of the invention may comprise administration of the pharmaceutical composition alone or in combination with one or more additional therapeutic agents. In some embodiments, the pharmaceutical composition is administered in conjunction with the cofactor tetrahydrobiopterin (e.g., Kuvan/sapropterin), large neutral amino acids (e.g., tyrosine, tryptophan), glycomacropeptides, a probiotic (e.g., VSL3), an enzyme (e.g., pegylated-PAL), and/or other agents used in the treatment of phenylketonuria (Al Hafid and Christodoulou, 2015).

In some embodiments, the genetically engineered microorganisms are administered in combination with one or more recombinantly produced PME enzymes, e.g. recombinant PAL, LAAD or PAH. In some embodiments, the recombinant PAL is a mutant PAL. In some embodiments, the recombinant enzymes are further formulated for improved stability and/or delivery. In some embodiments, the one or more PME enzyme administered in combination with the genetically engineered bacteria is peggylated. In some embodiments, the one or more PME enzyme administered in combination with the genetically engineered bacteria is delivered as a fusion protein. A non-limiting example of such a fusion protein is a fusion between a PME and a transduction domain for uptake into cells. A non-limiting example of such transduction domain or cell penetrating peptide is the TAT peptide. In some embodiments, the one or more PME enzyme administered in combination with the genetically engineered bacteria is formulated in a nanoparticle. A non-limiting example of such a nanoparticle is a dextran sulfate/chitosan PME nanoparticle. In some embodiments, the one or more PME enzyme administered in combination with the genetically engineered bacteria is delivered as a PME microsphere. A non-limiting example of such a microsphere is a barium alginate PME microsphere. In some embodiments, the one or more PME enzyme administered in combination with the genetically engineered microorganism is delivered as amorphous silica PME particles.

EXAMPLES

Example 1. Construction of PAL Plasmids and Transforming Bacteria

To facilitate inducible production of PAL in *Escherichia coli* Nissle, the PAL gene of *Anabaena variabilis* or *Photorhabdus luminescens*, as well as transcriptional and translational elements, were synthesized (Gen9, Cambridge, Mass.) and cloned into vector pBR322. The PAL gene was placed under the control of an inducible promoter. Low-copy and high-copy plasmids were generated for each of PAL1 and PAL3 under the control of an inducible FNR promoter or a Tet promoter. Exemplary promoters are provided herein.

Each of the plasmids described herein was transformed into *E. coli* Nissle for the studies described herein according to the following steps. All tubes, solutions, and cuvettes were pre-chilled to 4° C. An overnight culture of *E. coli* Nissle was diluted 1:100 in 5 mL of lysogeny broth (LB) containing ampicillin and grown until it reached an $OD_{600}$ of 0.4-0.6. The *E. coli* cells were then centrifuged at 2,000 rpm for 5 min at 4° C., the supernatant was removed, and the cells were resuspended in 1 mL of 4° C. water. The *E. coli* were again centrifuged at 2,000 rpm for 5 min at 4° C., the supernatant was removed, and the cells were resuspended in 0.5 mL of 4° C. water. The *E. coli* were again centrifuged at 2,000 rpm for 5 min at 4° C., the supernatant was removed, and the cells were finally resuspended in 0.1 mL of 4° C. water. The electroporator was set to 2.5 kV. Plasmid (0.5 μg) was added to the cells, mixed by pipetting, and pipetted into a sterile, chilled cuvette. The dry cuvette was placed into the sample chamber, and the electric pulse was applied. One mL of room-temperature SOC media was added immediately, and the mixture was transferred to a culture tube and incubated at 37° C. for 1 hr. The cells were spread out on an LB plate containing ampicillin and incubated overnight.

To facilitate inducible production of mutant, mPAL1, mPAL2 and mPAL3 were cloned into low copy plasmids (pSC101 origin of replication) under control of an anhydrous tetracycline (aTc)-responsive promoter and transferred to Nissle bacteria.

Example 2. Screening Process, Including Identification of mPAL1, mPAL2 and mPAL3

To generate PAL activity in strains, cultures containing plasmids expressing wild type PAL3, mPAL1, mPAL2, and mPAL3 were first grown overnight. The next morning, overnight cultures were used to back-dilute into fresh media at an OD600=0.1 and cultures were grown to early log phase. Upon entry into early log phase, aTc was added at a concentration of 200 ng/mL for induction of PAL, and the induction proceeded for 5 hours. At the end of the induction phase, the cultures were centrifuged, the supernatant discarded, and the pellets resuspended in 15% glycerol. The cell material was stored at −80 degrees C. until the day of testing in vitro PAL activity (TCA production).

To test for PAL activity from activated cells, frozen cell aliquots were thawed and resuspended in sodium bicarbonate buffer at $5.0 \times 10^9$ CFU/mL. This solution was then mixed with equal parts of simulated gastric fluid (SGF) and incubated for 2 hours at 37° C. with shaking. After 2 hours, samples were removed and cells were pelleted by centrifugation. The supernatant was recovered and analyzed for trans-cinnamate (TCA) (see FIGS. 1 and 2).

Quantification of trans-cinnamic acid (TCA) was performed using a Shimadzu HPLC-PDA system. TCA standards were prepared in assay media with the following concentrations: 0.005, 0.03, 0.1, 0.7, 3.4, 6.7, 16.9, 33.7, 50.6 mM. Bacterial supernatant samples were thawed and centrifuged at 4000 rpm for 5 min. In a 96-well plate, 5 μL of the standards and samples were transferred, followed by the addition of 195 μL of water. The plate was heat-sealed with a ClearSeal cover and mixed.

Figure 2:
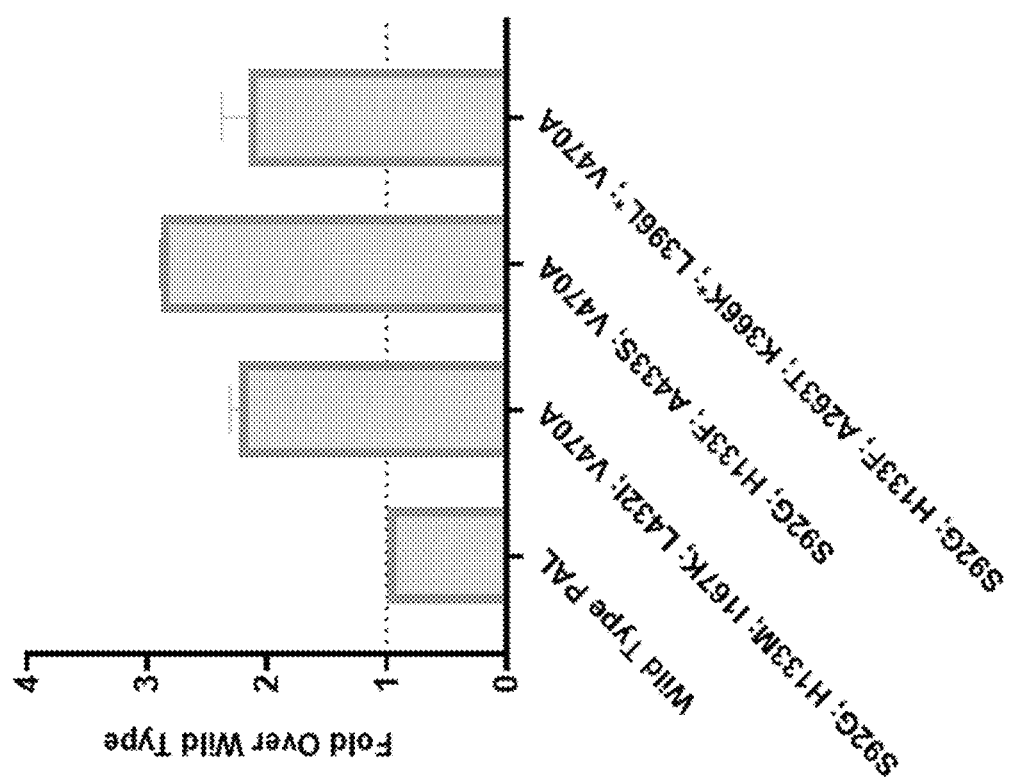
FIG. 2 depicts phenylalanine metabolism by mPAL1, mPAL2 and mPAL3 compared to wild type PAL3.

The injection volume used was 204 and the run time was 10 min at a flow rate of 0.35 mL/min. Mobile phase A was 0.1% Trifluoroacetic acid in water and mobile phase B was 0.1% Trifluoroacetic acid in acetonitrile. Chromatographic separation was carried out using a Thermo Scientific Hypersil Gold, 100×21 mm, 1.9μ, Part No. 25002-102130, with the following gradient: 5%435% B from 0 to 2 min, 35% B from 2 to 4 min, 90% B from 4.01 to 4.50 min, 5% B from 4.51 to 6 min, stop at 10 min. Retention time for TCA was 6.05 min, absorbing at 315 nm. (FIG. 1 and FIG. 2).

Example 3. Efficacy of Mutant PAL in a Mouse Model of PKU

For in vivo studies, BTBR-Pah$^{enu2}$ mice are obtained from Jackson Laboratory and bred to homozygosity for use as a model of PKU. Bacteria harboring the PAL mutant described herein are grown. Bacteria are resuspended in phosphate buffered saline (PBS) and administered to mice by oral gavage. The bacteria may be induced by ATC for 2 hours prior to administration.

At the beginning of the study, mice are given water that was supplemented with 100 micrograms/mL ATC and 5% sucrose. Mice are fasted by removing chow overnight (10 hrs), and blood samples are collected by mandibular bleeding the next morning in order to determine baseline phenylalanine levels. Blood samples are collected in heparinized tubes and spun at 2G for 20 min to produce plasma, which is then removed and stored at −80° C. Mice are given chow again, and are gavaged after 1 hr. with 100 μL ($5 \times 10^9$ CFU) of bacteria that had previously been induced for 2 hrs with ATC. Mice are put back on chow for 2 hrs. Plasma samples are prepared as described above. Phenylalanine levels before and after feeding are measured and compared to controls.

For subcutaneous phenylalanine challenge, beginning at least 3 days prior to the study (i.e., Days −6 to −3), homozygous BTBR-Pah$^{enu2}$ mice (approx. 6-12 weeks of age) are maintained on phenylalanine-free chow and water supplemented with 0.5 grams/L phenylalanine. On Day 1, mice are randomized into treatment groups and blood samples are collected by sub-mandibular skin puncture to determine baseline phenylalanine levels. Mice are also weighed to determine the average weight for each group. Mice are then administered single dose of phenylalanine by subcutaneous injection at 0.1 mg per gram body weight, according to the average group weight. At 30 and 90 min post-injection, 200 μL of $H_2O$ (n=30), control bacteria, or the bacteria comprising mutant PAL are administered to mice by oral gavage. Blood samples are collected at 2 hrs and 4 hrs following phenylalanine challenge, and phenylalanine levels in the blood are measured using mass spectrometry.

Additional assays of PAL activity, e.g., mutant PAL activity, are known in the art. See, e.g., PCT/US2016/032562 and PCT/US2016/062369, the contents of which are hereby incorporated by reference.

Example 4. Kinetic Measurements of PAL Variants

Figure 3A:
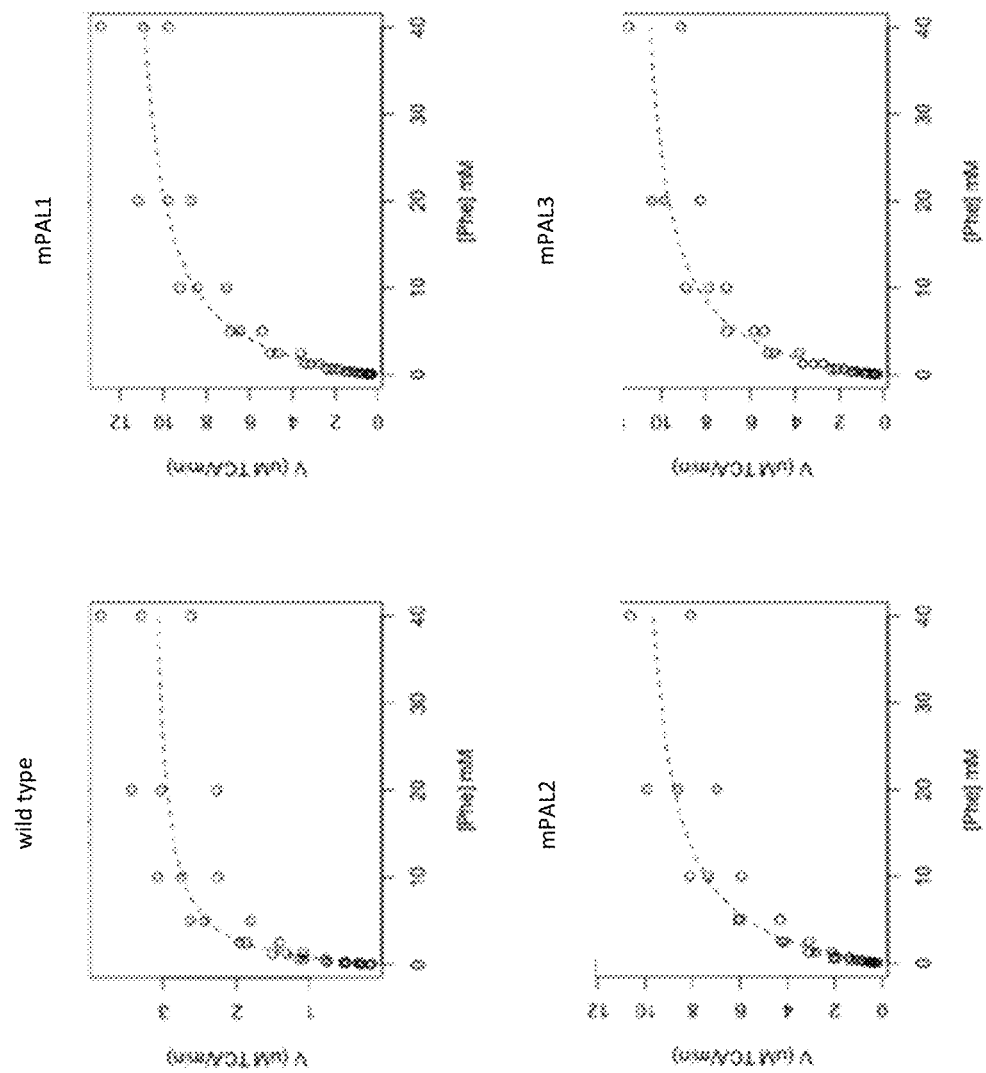

Michaelis-Menten graphs with rate V (µM TCA/min) as a function of Phe concentration [Phe] (mM) were generated for wild type PAL3, mPAL1, mPAL2, and mPAL3. Bacteria were inoculated 1:100 from a saturated overnight pre-culture, followed by induction with 200 ng/mL ATC two hours later. After four hours of induction, cells were pelleted, washed in PBS, normalized to $OD_{600}$=50 in PBS, and diluted 2-fold into 50% glycerol for storage at −80° C. Lysate from each strain was prepared via sonication using a Branson Digital Sonifier with microtip. The soluble fraction of the lysate samples was used for the kinetic assay. Total protein in the lysate samples was measured via Bradford Assay, and all samples were normalized to 10 µg total protein loading per well for the kinetic assay. The lysate samples were incubated in 1×M9 0.5% glucose with Phe concentrations ranging from 40 mM Phe down to 39 µM with 2-fold dilutions. The kinetic assay was performed in UV-star 96-well microplates (Greiner) with TCA quantified by A290 measurements every minute using a BioTek Synergy H1 microplate reader set to 37° C. static incubation. The data points on each graph are rate (V in µM TCA/min) calculated from the first hour of activity for each Phe concentration tested, where activity remained linear. (FIG. 3).

Example 5. Efficacy of Mutant PAL in a Cynomolgus Monkey Model

Figure 4B:
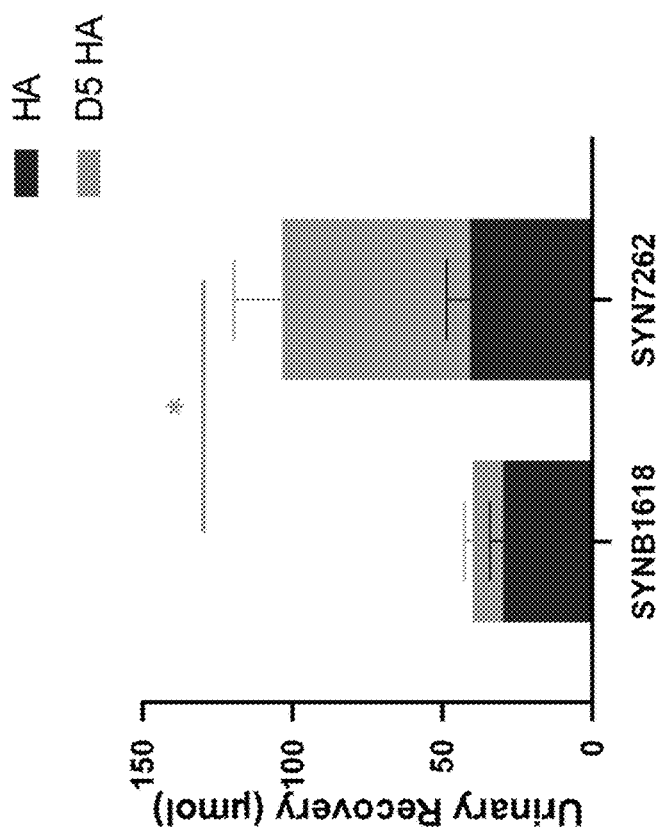
FIGS. 4A-C depict in vitro studies of mutant PAL efficacy in a cynomolgus monkey model. Activity of PAL variants was measured by assaying levels of plasma TCA and hippurate in urine.
Figure 4A:
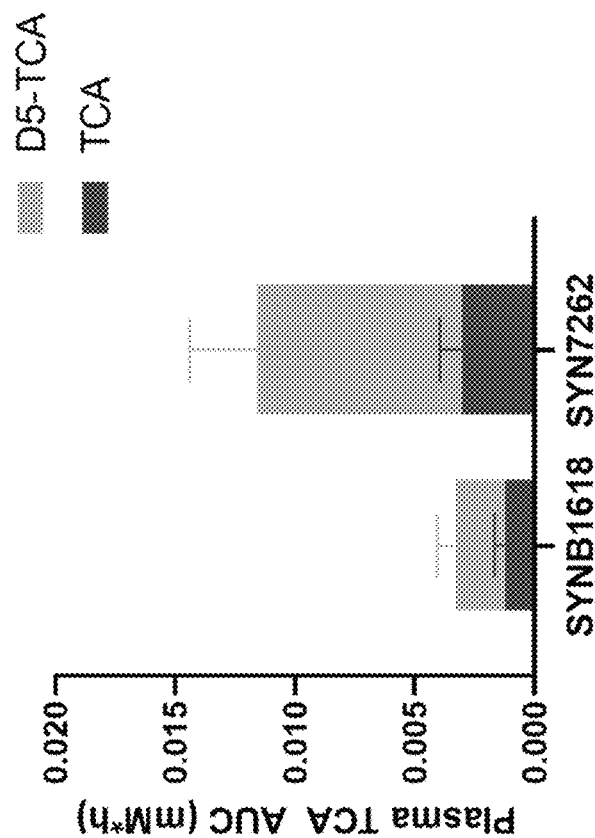
Figure 4C:
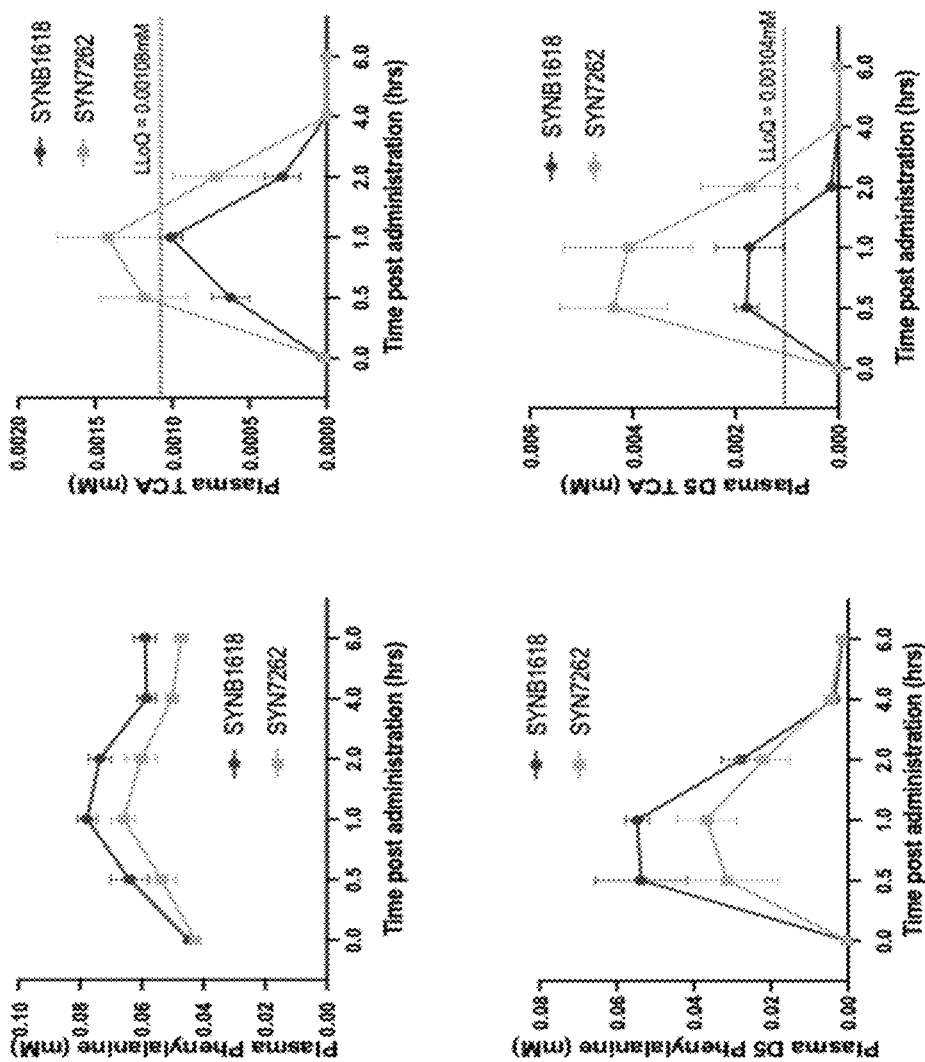

To evaluate the in vivo efficacy of the mutant PAL described herein, genetically engineered E. coli Nissle comprising mPAL2 (SYN7262) was administered via nasal gastric gavage as described in U.S. Pat. No. 10,610,546, the contents of which are hereby incorporated by reference in its entirety. Briefly, SYNB1618 and SYN7262 strains were grown in a bioreactor and PAL expression induced via addition of anaerobiosis/IPTG or ATC/IPTG, respectively. At the end of fermentation, cells were spun down and stored in 15% glycerol at −80 C. On the day of dosing, each animal was administered 5.5 g of protein in the form of peptone, and 250 mg of D5-Phe, followed by a 1e11 live cell dose of either SYNB1618 or SYN7262. Blood and urine were collected over a six-hour period. Plasma TCA areas under the curve, as well as excretion of urinary hippurate were analyzed via liquid chromatography coupled to tandem mass spectrometry (LC-MS/MS) using a Thermo TSQ Quantum Max triple quadrupole mass spectrometer. (FIG. 4).

Example 6. Whole Cell Activity of PKU Strains

Figure 5A:
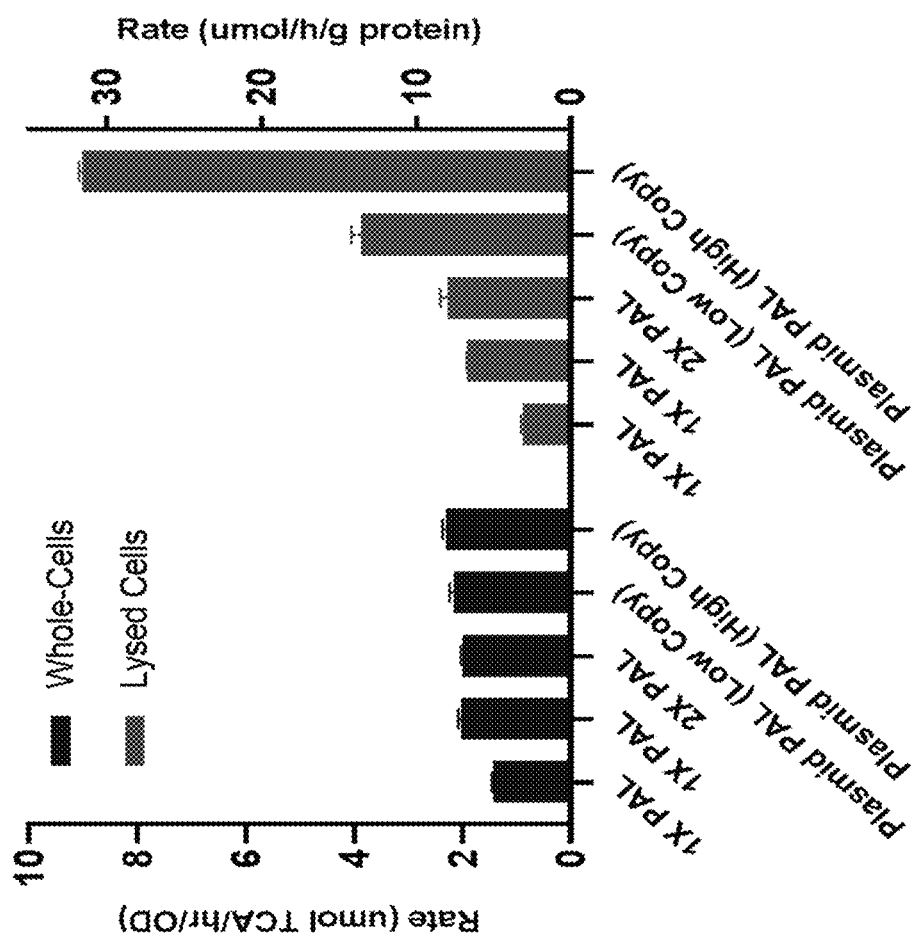
FIGS. 5A-C depict TCA feedback inhibition of wild type PAL3 activity as determined via whole cell and cell lysate assays.
Figures 5B, 5C:
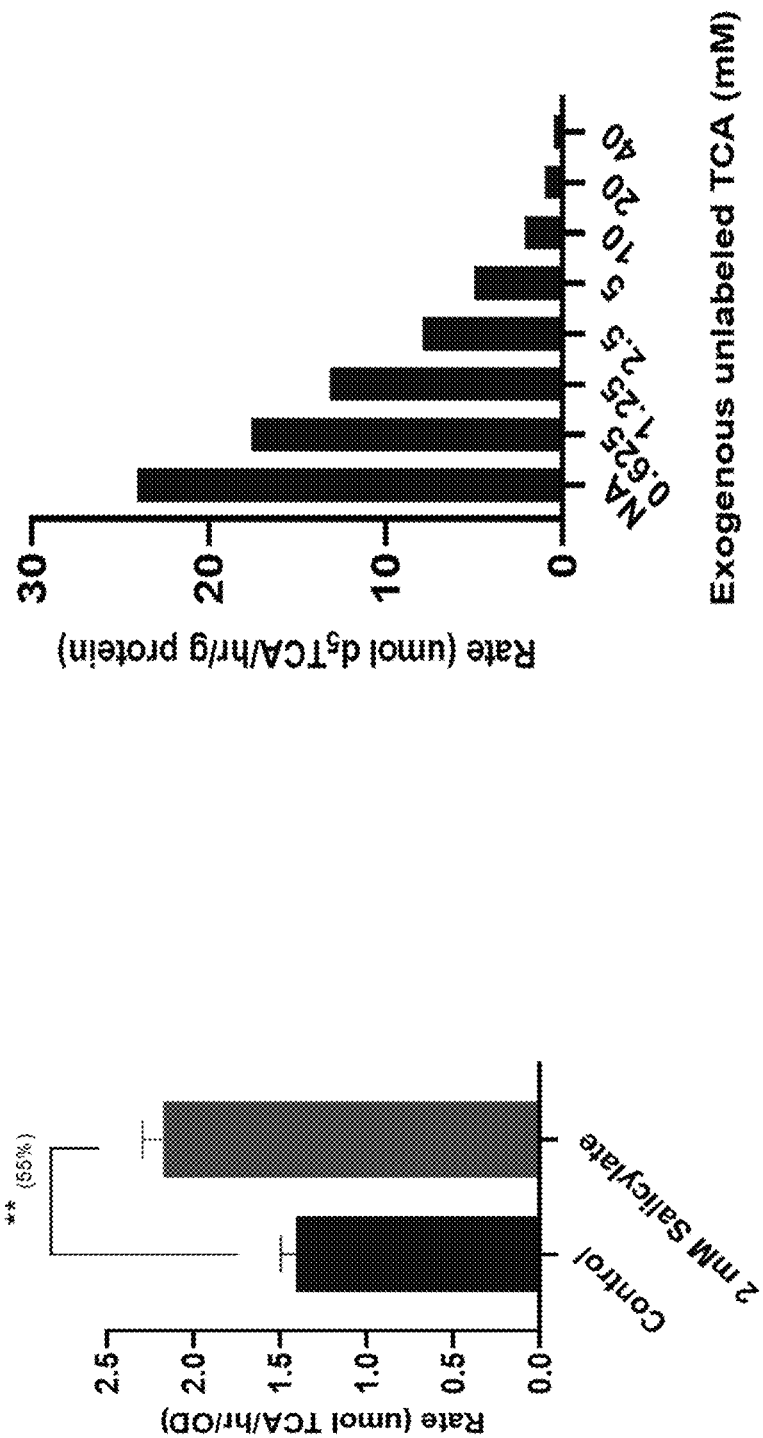

Bacterial strains comprising different copy numbers of wild type PAL3 were prepared as described herein. A portion of cells from each strain were then lysed. The soluble fraction of the lysate samples was used for the activity assay. PAL3 activity of intact bacteria and lysates was measured as described previously. Increased copy number (expression) of PAL3 has little effect on whole-cell rate of TCA production. In contrast, when the same cell material is lysed, increased copy number (expression) corresponds to increased activity. Lysate PAL activity, measured by conversion of $d_5$-Phe to $d_5$-TCA, decreases in the presence of increasing exogenous unlabeled TCA, demonstrating that the enzyme is feedback inhibited by its product. Addition of salicylate, an inducer of efflux pumps in E. coli, during induction of PAL led to increased rates of whole-cell PAL activity in vitro. (FIG. 5).

The invention claimed is:

1. A mutant phenylalanine ammonia lyase (PAL) polypeptide comprising one or more mutations at amino acid positions selected from S92, H133, I167, L432, V470, A433, A263, K366 and L396 compared to a wildtype *Photorhabdus luminescens* PAL comprising SEQ ID NO: 1.

2. The mutant PAL polypeptide of claim 1, wherein the mutations comprise:

(a) S92G; H133M; I167K; L432I; V470A;

(b) S92G; H133F; A433S; V470A; or (c) S92G; H133F; A263T; V470A.

3. The mutant PAL polypeptide of claim 1, wherein the polypeptide exhibits increased ability to metabolize phenylalanine compared to the wildtype PAL.

4. The mutant PAL polypeptide of claim 1, wherein the polypeptide exhibits at least two-fold increase in the ability to metabolize phenylalanine compared to the wildtype PAL.

5. The mutant PAL polypeptide of claim 1, wherein the polypeptide exhibits at least three-fold increase in the ability to metabolize phenylalanine compared to the wildtype PAL.

6. The mutant PAL polypeptide of claim 1, wherein the polypeptide exhibits at least four-fold increase in the ability to metabolize phenylalanine compared to the wildtype PAL.

7. The mutant PAL polypeptide of claim 1, wherein the polypeptide exhibits at least five-fold increase in the ability to metabolize phenylalanine compared to the wildtype PAL.

8. A composition comprising the mutant PAL polypeptide of claim 1.

* * * * *

SEQUENCE LISTING

<160> NUMBER OF SEQ ID NOS: 26

<210> SEQ ID NO 1
<211> LENGTH: 532
<212> TYPE: PRT
<213> ORGANISM: Photorhabdus luminescens

<400> SEQUENCE: 1

```
Met Lys Ala Lys Asp Val Gln Pro Thr Ile Ile Ile Asn Lys Asn Gly
1               5                   10                  15

Leu Ile Ser Leu Glu Asp Ile Tyr Asp Ile Ala Ile Lys Gln Lys Lys
                20                  25                  30

Val Glu Ile Ser Thr Glu Ile Thr Glu Leu Leu Thr His Gly Arg Glu
            35                  40                  45

Lys Leu Glu Glu Lys Leu Asn Ser Gly Glu Val Ile Tyr Gly Ile Asn
        50                  55                  60

Thr Gly Phe Gly Gly Asn Ala Asn Leu Val Val Pro Phe Glu Lys Ile
65                  70                  75                  80

Ala Glu His Gln Gln Asn Leu Leu Thr Phe Leu Ser Ala Gly Thr Gly
                85                  90                  95

Asp Tyr Met Ser Lys Pro Cys Ile Lys Ala Ser Gln Phe Thr Met Leu
                100                 105                 110

Leu Ser Val Cys Lys Gly Trp Ser Ala Thr Arg Pro Ile Val Ala Gln
                115                 120                 125
```

```
Ala Ile Val Asp His Ile Asn His Asp Ile Val Pro Leu Val Pro Arg
    130                 135                 140

Tyr Gly Ser Val Gly Ala Ser Gly Asp Leu Ile Pro Leu Ser Tyr Ile
145                 150                 155                 160

Ala Arg Ala Leu Cys Gly Ile Gly Lys Val Tyr Tyr Met Gly Ala Glu
                165                 170                 175

Ile Asp Ala Ala Glu Ala Ile Lys Arg Ala Gly Leu Thr Pro Leu Ser
                180                 185                 190

Leu Lys Ala Lys Glu Gly Leu Ala Leu Ile Asn Gly Thr Arg Val Met
        195                 200                 205

Ser Gly Ile Ser Ala Ile Thr Val Ile Lys Leu Glu Lys Leu Phe Lys
        210                 215                 220

Ala Ser Ile Ser Ala Ile Ala Leu Ala Val Glu Ala Leu Leu Ala Ser
225                 230                 235                 240

His Glu His Tyr Asp Ala Arg Ile Gln Gln Val Lys Asn His Pro Gly
                245                 250                 255

Gln Asn Ala Val Ala Ser Ala Leu Arg Asn Leu Leu Ala Gly Ser Thr
                260                 265                 270

Gln Val Asn Leu Leu Ser Gly Val Lys Glu Gln Ala Asn Lys Ala Cys
        275                 280                 285

Arg His Gln Glu Ile Thr Gln Leu Asn Asp Thr Leu Gln Glu Val Tyr
        290                 295                 300

Ser Ile Arg Cys Ala Pro Gln Val Leu Gly Ile Val Pro Glu Ser Leu
305                 310                 315                 320

Ala Thr Ala Arg Lys Ile Leu Glu Arg Glu Val Ile Ser Ala Asn Asp
                325                 330                 335

Asn Pro Leu Ile Asp Pro Glu Asn Gly Asp Val Leu His Gly Gly Asn
                340                 345                 350

Phe Met Gly Gln Tyr Val Ala Arg Thr Met Asp Ala Leu Lys Leu Asp
        355                 360                 365

Ile Ala Leu Ile Ala Asn His Leu His Ala Ile Val Ala Leu Met Met
        370                 375                 380

Asp Asn Arg Phe Ser Arg Gly Leu Pro Asn Ser Leu Ser Pro Thr Pro
385                 390                 395                 400

Gly Met Tyr Gln Gly Phe Lys Gly Val Gln Leu Ser Gln Thr Ala Leu
                405                 410                 415

Val Ala Ala Ile Arg His Asp Cys Ala Ala Ser Gly Ile His Thr Leu
                420                 425                 430

Ala Thr Glu Gln Tyr Asn Gln Asp Ile Val Ser Leu Gly Leu His Ala
        435                 440                 445

Ala Gln Asp Val Leu Glu Met Glu Gln Lys Leu Arg Asn Ile Val Ser
450                 455                 460

Met Thr Ile Leu Val Val Cys Gln Ala Ile His Leu Arg Gly Asn Ile
465                 470                 475                 480

Ser Glu Ile Ala Pro Glu Thr Ala Lys Phe Tyr His Ala Val Arg Glu
                485                 490                 495

Ile Ser Ser Pro Leu Ile Thr Asp Arg Ala Leu Asp Glu Asp Ile Ile
                500                 505                 510

Arg Ile Ala Asp Ala Ile Ile Asn Asp Gln Leu Pro Leu Pro Glu Ile
        515                 520                 525

Met Leu Glu Glu
    530
```

<210> SEQ ID NO 2
<211> LENGTH: 532
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 2

```
Met Lys Ala Lys Asp Val Gln Pro Thr Ile Ile Asn Lys Asn Gly
1               5                   10                  15

Leu Ile Ser Leu Glu Asp Ile Tyr Asp Ile Ala Ile Lys Gln Lys Lys
            20                  25                  30

Val Glu Ile Ser Thr Glu Ile Thr Glu Leu Leu Thr His Gly Arg Glu
        35                  40                  45

Lys Leu Glu Glu Lys Leu Asn Ser Gly Glu Val Ile Tyr Gly Ile Asn
    50                  55                  60

Thr Gly Phe Gly Gly Asn Ala Asn Leu Val Val Pro Phe Glu Lys Ile
65              70                  75                  80

Ala Glu His Gln Gln Asn Leu Leu Thr Phe Leu Gly Ala Gly Thr Gly
                85                  90                  95

Asp Tyr Met Ser Lys Pro Cys Ile Lys Ala Ser Gln Phe Thr Met Leu
            100                 105                 110

Leu Ser Val Cys Lys Gly Trp Ser Ala Thr Arg Pro Ile Val Ala Gln
        115                 120                 125

Ala Ile Val Asp Met Ile Asn His Asp Ile Val Pro Leu Val Pro Arg
    130                 135                 140

Tyr Gly Ser Val Gly Ala Ser Gly Asp Leu Ile Pro Leu Ser Tyr Ile
145                 150                 155                 160

Ala Arg Ala Leu Cys Gly Lys Gly Lys Val Tyr Tyr Met Gly Ala Glu
                165                 170                 175

Ile Asp Ala Ala Glu Ala Ile Lys Arg Ala Gly Leu Thr Pro Leu Ser
            180                 185                 190

Leu Lys Ala Lys Glu Gly Leu Ala Leu Ile Asn Gly Thr Arg Val Met
        195                 200                 205

Ser Gly Ile Ser Ala Ile Thr Val Ile Lys Leu Glu Lys Leu Phe Lys
    210                 215                 220

Ala Ser Ile Ser Ala Ile Ala Leu Ala Val Glu Ala Leu Leu Ala Ser
225                 230                 235                 240

His Glu His Tyr Asp Ala Arg Ile Gln Gln Val Lys Asn His Pro Gly
                245                 250                 255

Gln Asn Ala Val Ala Ser Ala Leu Arg Asn Leu Leu Ala Gly Ser Thr
            260                 265                 270

Gln Val Asn Leu Leu Ser Gly Val Lys Glu Gln Ala Asn Lys Ala Cys
        275                 280                 285

Arg His Gln Glu Ile Thr Gln Leu Asn Asp Thr Leu Gln Glu Val Tyr
    290                 295                 300

Ser Ile Arg Cys Ala Pro Gln Val Leu Gly Ile Val Pro Glu Ser Leu
305                 310                 315                 320

Ala Thr Ala Arg Lys Ile Leu Glu Arg Glu Val Ile Ser Ala Asn Asp
                325                 330                 335

Asn Pro Leu Ile Asp Pro Glu Asn Gly Asp Val Leu His Gly Gly Asn
            340                 345                 350

Phe Met Gly Gln Tyr Val Ala Arg Thr Met Asp Ala Leu Lys Leu Asp
```

```
            355                 360                 365
Ile Ala Leu Ile Ala Asn His Leu His Ala Ile Val Ala Leu Met Met
    370                 375                 380

Asp Asn Arg Phe Ser Arg Gly Leu Pro Asn Ser Leu Ser Pro Thr Pro
385                 390                 395                 400

Gly Met Tyr Gln Gly Phe Lys Gly Val Gln Leu Ser Gln Thr Ala Leu
                405                 410                 415

Val Ala Ala Ile Arg His Asp Cys Ala Ala Ser Gly Ile His Thr Ile
            420                 425                 430

Ala Thr Glu Gln Tyr Asn Gln Asp Ile Val Ser Leu Gly Leu His Ala
        435                 440                 445

Ala Gln Asp Val Leu Glu Met Glu Gln Lys Leu Arg Asn Ile Val Ser
    450                 455                 460

Met Thr Ile Leu Val Ala Cys Gln Ala Ile His Leu Arg Gly Asn Ile
465                 470                 475                 480

Ser Glu Ile Ala Pro Glu Thr Ala Lys Phe Tyr His Ala Val Arg Glu
                485                 490                 495

Ile Ser Ser Pro Leu Ile Thr Asp Arg Ala Leu Asp Glu Asp Ile Ile
            500                 505                 510

Arg Ile Ala Asp Ala Ile Ile Asn Asp Gln Leu Pro Leu Pro Glu Ile
        515                 520                 525

Met Leu Glu Glu
    530

<210> SEQ ID NO 3
<211> LENGTH: 532
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 3

Met Lys Ala Lys Asp Val Gln Pro Thr Ile Ile Asn Lys Asn Gly
1               5                   10                  15

Leu Ile Ser Leu Glu Asp Ile Tyr Asp Ile Ala Ile Lys Gln Lys Lys
            20                  25                  30

Val Glu Ile Ser Thr Glu Ile Thr Glu Leu Leu Thr His Gly Arg Glu
        35                  40                  45

Lys Leu Glu Glu Lys Leu Asn Ser Gly Glu Val Ile Tyr Gly Ile Asn
    50                  55                  60

Thr Gly Phe Gly Gly Asn Ala Asn Leu Val Val Pro Phe Glu Lys Ile
65                  70                  75                  80

Ala Glu His Gln Gln Asn Leu Leu Thr Phe Leu Gly Ala Gly Thr Gly
                85                  90                  95

Asp Tyr Met Ser Lys Pro Cys Ile Lys Ala Ser Gln Phe Thr Met Leu
            100                 105                 110

Leu Ser Val Cys Lys Gly Trp Ser Ala Thr Arg Pro Ile Val Ala Gln
        115                 120                 125

Ala Ile Val Asp Phe Ile Asn His Asp Ile Val Pro Leu Val Pro Arg
    130                 135                 140

Tyr Gly Ser Val Gly Ala Ser Gly Asp Leu Ile Pro Leu Ser Tyr Ile
145                 150                 155                 160

Ala Arg Ala Leu Cys Gly Ile Gly Lys Val Tyr Tyr Met Gly Ala Glu
                165                 170                 175
```

```
Ile Asp Ala Ala Glu Ala Ile Lys Arg Ala Gly Leu Thr Pro Leu Ser
            180                 185                 190

Leu Lys Ala Lys Glu Gly Leu Ala Leu Ile Asn Gly Thr Arg Val Met
        195                 200                 205

Ser Gly Ile Ser Ala Ile Thr Val Ile Lys Leu Glu Lys Leu Phe Lys
    210                 215                 220

Ala Ser Ile Ser Ala Ile Ala Leu Ala Val Glu Ala Leu Leu Ala Ser
225                 230                 235                 240

His Glu His Tyr Asp Ala Arg Ile Gln Gln Val Lys Asn His Pro Gly
                245                 250                 255

Gln Asn Ala Val Ala Ser Ala Leu Arg Asn Leu Leu Ala Gly Ser Thr
            260                 265                 270

Gln Val Asn Leu Leu Ser Gly Val Lys Glu Gln Ala Asn Lys Ala Cys
        275                 280                 285

Arg His Gln Glu Ile Thr Gln Leu Asn Asp Thr Leu Gln Glu Val Tyr
    290                 295                 300

Ser Ile Arg Cys Ala Pro Gln Val Leu Gly Ile Val Pro Glu Ser Leu
305                 310                 315                 320

Ala Thr Ala Arg Lys Ile Leu Glu Arg Glu Val Ile Ser Ala Asn Asp
                325                 330                 335

Asn Pro Leu Ile Asp Pro Glu Asn Gly Asp Val Leu His Gly Gly Asn
            340                 345                 350

Phe Met Gly Gln Tyr Val Ala Arg Thr Met Asp Ala Leu Lys Leu Asp
        355                 360                 365

Ile Ala Leu Ile Ala Asn His Leu His Ala Ile Val Ala Leu Met Met
    370                 375                 380

Asp Asn Arg Phe Ser Arg Gly Leu Pro Asn Ser Leu Ser Pro Thr Pro
385                 390                 395                 400

Gly Met Tyr Gln Gly Phe Lys Gly Val Gln Leu Ser Gln Thr Ala Leu
                405                 410                 415

Val Ala Ala Ile Arg His Asp Cys Ala Ala Ser Gly Ile His Thr Leu
            420                 425                 430

Ser Thr Glu Gln Tyr Asn Gln Asp Ile Val Ser Leu Gly Leu His Ala
        435                 440                 445

Ala Gln Asp Val Leu Glu Met Glu Gln Lys Leu Arg Asn Ile Val Ser
    450                 455                 460

Met Thr Ile Leu Val Ala Cys Gln Ala Ile His Leu Arg Gly Asn Ile
465                 470                 475                 480

Ser Glu Ile Ala Pro Glu Thr Ala Lys Phe Tyr His Ala Val Arg Glu
                485                 490                 495

Ile Ser Ser Pro Leu Ile Thr Asp Arg Ala Leu Asp Glu Asp Ile Ile
            500                 505                 510

Arg Ile Ala Asp Ala Ile Ile Asn Asp Gln Leu Pro Leu Pro Glu Ile
        515                 520                 525

Met Leu Glu Glu
    530

<210> SEQ ID NO 4
<211> LENGTH: 532
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

<400> SEQUENCE: 4

```
Met Lys Ala Lys Asp Val Gln Pro Thr Ile Ile Ile Asn Lys Asn Gly
1               5                   10                  15

Leu Ile Ser Leu Glu Asp Ile Tyr Asp Ile Ala Ile Lys Gln Lys Lys
            20                  25                  30

Val Glu Ile Ser Thr Glu Ile Thr Glu Leu Leu Thr His Gly Arg Glu
        35                  40                  45

Lys Leu Glu Glu Lys Leu Asn Ser Gly Glu Val Ile Tyr Gly Ile Asn
    50                  55                  60

Thr Gly Phe Gly Gly Asn Ala Asn Leu Val Val Pro Phe Glu Lys Ile
65                  70                  75                  80

Ala Glu His Gln Gln Asn Leu Leu Thr Phe Leu Gly Ala Gly Thr Gly
                85                  90                  95

Asp Tyr Met Ser Lys Pro Cys Ile Lys Ala Ser Gln Phe Thr Met Leu
            100                 105                 110

Leu Ser Val Cys Lys Gly Trp Ser Ala Thr Arg Pro Ile Val Ala Gln
        115                 120                 125

Ala Ile Val Asp Phe Ile Asn His Asp Ile Val Pro Leu Val Pro Arg
    130                 135                 140

Tyr Gly Ser Val Gly Ala Ser Gly Asp Leu Ile Pro Leu Ser Tyr Ile
145                 150                 155                 160

Ala Arg Ala Leu Cys Gly Ile Gly Lys Val Tyr Tyr Met Gly Ala Glu
                165                 170                 175

Ile Asp Ala Ala Glu Ala Ile Lys Arg Ala Gly Leu Thr Pro Leu Ser
            180                 185                 190

Leu Lys Ala Lys Glu Gly Leu Ala Leu Ile Asn Gly Thr Arg Val Met
        195                 200                 205

Ser Gly Ile Ser Ala Ile Thr Val Ile Lys Leu Glu Lys Leu Phe Lys
    210                 215                 220

Ala Ser Ile Ser Ala Ile Ala Leu Ala Val Glu Ala Leu Leu Ala Ser
225                 230                 235                 240

His Glu His Tyr Asp Ala Arg Ile Gln Gln Val Lys Asn His Pro Gly
                245                 250                 255

Gln Asn Ala Val Ala Ser Thr Leu Arg Asn Leu Leu Ala Gly Ser Thr
            260                 265                 270

Gln Val Asn Leu Leu Ser Gly Val Lys Glu Gln Ala Asn Lys Ala Cys
        275                 280                 285

Arg His Gln Glu Ile Thr Gln Leu Asn Asp Thr Leu Gln Glu Val Tyr
    290                 295                 300

Ser Ile Arg Cys Ala Pro Gln Val Leu Gly Ile Val Pro Glu Ser Leu
305                 310                 315                 320

Ala Thr Ala Arg Lys Ile Leu Glu Arg Glu Val Ile Ser Ala Asn Asp
                325                 330                 335

Asn Pro Leu Ile Asp Pro Glu Asn Gly Asp Val Leu His Gly Gly Asn
            340                 345                 350

Phe Met Gly Gln Tyr Val Ala Arg Thr Met Asp Ala Leu Lys Leu Asp
        355                 360                 365

Ile Ala Leu Ile Ala Asn His Leu His Ala Ile Val Ala Leu Met Met
    370                 375                 380

Asp Asn Arg Phe Ser Arg Gly Leu Pro Asn Ser Leu Ser Pro Thr Pro
385                 390                 395                 400

Gly Met Tyr Gln Gly Phe Lys Gly Val Gln Leu Ser Gln Thr Ala Leu
```

```
            405                 410                 415
Val Ala Ala Ile Arg His Asp Cys Ala Ala Ser Gly Ile His Thr Leu
        420                 425                 430

Ala Thr Glu Gln Tyr Asn Gln Asp Ile Val Ser Leu Gly Leu His Ala
            435                 440                 445

Ala Gln Asp Val Leu Glu Met Glu Gln Lys Leu Arg Asn Ile Val Ser
        450                 455                 460

Met Thr Ile Leu Val Ala Cys Gln Ala Ile His Leu Arg Gly Asn Ile
465                 470                 475                 480

Ser Glu Ile Ala Pro Glu Thr Ala Lys Phe Tyr His Ala Val Arg Glu
            485                 490                 495

Ile Ser Ser Pro Leu Ile Thr Asp Arg Ala Leu Asp Glu Asp Ile Ile
        500                 505                 510

Arg Ile Ala Asp Ala Ile Ile Asn Asp Gln Leu Pro Leu Pro Glu Ile
    515                 520                 525

Met Leu Glu Glu
    530

<210> SEQ ID NO 5

<400> SEQUENCE: 5

000

<210> SEQ ID NO 6

<400> SEQUENCE: 6

000

<210> SEQ ID NO 7

<400> SEQUENCE: 7

000

<210> SEQ ID NO 8

<400> SEQUENCE: 8

000

<210> SEQ ID NO 9
<211> LENGTH: 117
<212> TYPE: DNA
<213> ORGANISM: Unknown
<220> FEATURE:
<221> NAME/KEY: source
<223> OTHER INFORMATION: /note="Description of Unknown:
      FNR-responsive regulatory region sequence"

<400> SEQUENCE: 9
atccccatca ctcttgatgg agatcaattc cccaagctgc tagagcgtta ccttgccctt     60
aaacattagc aatgtcgatt tatcagaggg ccgacaggct cccacaggag aaaaccg      117

<210> SEQ ID NO 10
<211> LENGTH: 108
<212> TYPE: DNA
<213> ORGANISM: Unknown
<220> FEATURE:
<221> NAME/KEY: source
<223> OTHER INFORMATION: /note="Description of Unknown:
      FNR-responsive regulatory region sequence"
```

```
<400> SEQUENCE: 10
ctcttgatcg ttatcaattc ccacgctgtt tcagagcgtt accttgccct taaacattag      60
caatgtcgat ttatcagagg gccgacaggc tcccacagga gaaaaccg                  108

<210> SEQ ID NO 11
<211> LENGTH: 290
<212> TYPE: DNA
<213> ORGANISM: Unknown
<220> FEATURE:
<221> NAME/KEY: source
<223> OTHER INFORMATION: /note="Description of Unknown:
      nirB1 sequence"

<400> SEQUENCE: 11
gtcagcataa caccctgacc tctcattaat tgttcatgcc gggcggcact atcgtcgtcc      60
ggccttttcc tctcttactc tgctacgtac atctatttct ataaatccgt tcaatttgtc     120
tgttttttgc acaaacatga aatatcagac aattccgtga cttaagaaaa tttatacaaa     180
tcagcaatat accccttaag gagtatataa aggtgaattt gatttacatc aataagcggg     240
gttgctgaat cgttaaggta ggcggtaata gaaaagaaat cgaggcaaaa                290

<210> SEQ ID NO 12
<211> LENGTH: 433
<212> TYPE: DNA
<213> ORGANISM: Unknown
<220> FEATURE:
<221> NAME/KEY: source
<223> OTHER INFORMATION: /note="Description of Unknown:
      nirB2 sequence"

<400> SEQUENCE: 12
cggcccgatc gttgaacata gcggtccgca ggcggcactg cttacagcaa acggtctgta      60
cgctgtcgtc tttgtgatgt gcttcctgtt aggtttcgtc agccgtcacc gtcagcataa     120
caccctgacc tctcattaat tgctcatgcc ggacggcact atcgtcgtcc ggccttttcc     180
tctcttcccc cgctacgtgc atctatttct ataaacccgc tcattttgtc tattttttgc     240
acaaacatga aatatcagac aattccgtga cttaagaaaa tttatacaaa tcagcaatat     300
acccattaag gagtatataa aggtgaattt gatttacatc aataagcggg gttgctgaat     360
cgttaaggta ggcggtaata gaaaagaaat cgaggcaaaa atgtttgttt aactttaaga     420
aggagatata cat                                                        433

<210> SEQ ID NO 13
<211> LENGTH: 290
<212> TYPE: DNA
<213> ORGANISM: Unknown
<220> FEATURE:
<221> NAME/KEY: source
<223> OTHER INFORMATION: /note="Description of Unknown:
      nirB3 sequence"

<400> SEQUENCE: 13
gtcagcataa caccctgacc tctcattaat tgctcatgcc ggacggcact atcgtcgtcc      60
ggccttttcc tctcttcccc cgctacgtgc atctatttct ataaacccgc tcattttgtc     120
tattttttgc acaaacatga aatatcagac aattccgtga cttaagaaaa tttatacaaa     180
tcagcaatat acccattaag gagtatataa aggtgaattt gatttacatc aataagcggg     240
gttgctgaat cgttaaggta ggcggtaata gaaaagaaat cgaggcaaaa                290
```

<210> SEQ ID NO 14
<211> LENGTH: 173
<212> TYPE: DNA
<213> ORGANISM: Unknown
<220> FEATURE:
<221> NAME/KEY: source
<223> OTHER INFORMATION: /note="Description of Unknown:
    ydfZ sequence"

<400> SEQUENCE: 14
atttcctctc atcccatccg gggtgagagt cttttcccccc gacttatggc tcatgcatgc      60
atcaaaaaag atgtgagctt gatcaaaaac aaaaaatatt tcactcgaca ggagtattta     120
tattgcgccc gttacgtggg cttcgactgt aaatcagaaa ggagaaaaca cct            173

<210> SEQ ID NO 15
<211> LENGTH: 305
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 15
gtcagcataa caccctgacc tctcattaat tgttcatgcc gggcggcact atcgtcgtcc      60
ggccttttcc tctcttactc tgctacgtac atctatttct ataaatccgt tcaatttgtc     120
tgttttttgc acaaacatga aatatcagac aattccgtga cttaagaaaa tttatacaaa     180
tcagcaatat accccttaag gagtatataa aggtgaattt gatttacatc aataagcggg     240
gttgctgaat cgttaaggat ccctctagaa ataattttgt ttaactttaa gaaggagata     300
tacat                                                                 305

<210> SEQ ID NO 16
<211> LENGTH: 180
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 16
catttcctct catcccatcc ggggtgagag tcttttcccc cgacttatgg ctcatgcatg      60
catcaaaaaa gatgtgagct tgatcaaaaa caaaaaatat ttcactcgac aggagtattt     120
atattgcgcc cggatccctc tagaaataat tttgtttaac tttaagaagg agatatacat     180

<210> SEQ ID NO 17
<211> LENGTH: 199
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 17
agttgttctt attggtggtg ttgctttatg gttgcatcgt agtaaatggt tgtaacaaaa      60 gcaattttc cggctgtctg tatacaaaaa cgccgtaaag tttgagcgaa gtcaataaac      120
tctctaccca ttcagggcaa tatctctctt ggatccctct agaaataatt ttgtttaact     180
ttaagaagga gatatacat                                                  199

```
<210> SEQ ID NO 18
<211> LENGTH: 207
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 18
agttgttctt attggtggtg ttgctttatg gttgcatcgt agtaaatggt tgtaacaaaa      60 gcaattttc cggctgtctg tatacaaaaa cgccgcaaag tttgagcgaa gtcaataaac     120
tctctaccca ttcagggcaa tatctctctt ggatccaaag tgaactctag aaataatttt    180
gtttaacttt aagaaggaga tatacat                                         207

<210> SEQ ID NO 19
<211> LENGTH: 390
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 19
tcgtctttgt gatgtgcttc ctgttaggtt tcgtcagccg tcaccgtcag cataacaccc      60
tgacctctca ttaattgctc atgccggacg gcactatcgt cgtccggcct tttcctctct    120 tccccgcta cgtgcatcta tttctataaa cccgctcatt ttgtctattt tttgcacaaa    180
catgaaatat cagacaattc cgtgacttaa gaaaatttat acaaatcagc aatataccca    240
ttaaggagta tataaggtg aatttgattt acatcaataa gcggggttgc tgaatcgtta     300
aggtagaaat gtgatctagt tcacatttgc ggtaatagaa aagaaatcga ggcaaaaatg    360
tttgtttaac tttaagaagg agatatacat                                     390

<210> SEQ ID NO 20
<211> LENGTH: 200
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 20
agttgttctt attggtggtg ttgctttatg gttgcatcgt agtaaatggt tgtaacaaaa      60 gcaattttc cggctgtctg tatacaaaaa cgccgcaaag tttgagcgaa gtcaataaac     120
tctctaccca ttcagggcaa tatctctcaa atgtgatcta gttcacattt ttgtttaac    180 tttaagaagg agatatacat                                                200

<210> SEQ ID NO 21
<211> LENGTH: 567
<212> TYPE: PRT
<213> ORGANISM: Anabaena variabilis

<400> SEQUENCE: 21

Met Lys Thr Leu Ser Gln Ala Gln Ser Lys Thr Ser Ser Gln Gln Phe
1               5                   10                  15

Ser Phe Thr Gly Asn Ser Ser Ala Asn Val Ile Ile Gly Asn Gln Lys
```

```
                20                  25                  30
Leu Thr Ile Asn Asp Val Ala Arg Val Ala Arg Asn Gly Thr Leu Val
             35                  40                  45
Ser Leu Thr Asn Asn Thr Asp Ile Leu Gln Gly Ile Gln Ala Ser Cys
 50                  55                  60
Asp Tyr Ile Asn Asn Ala Val Glu Ser Gly Glu Pro Ile Tyr Gly Val
 65                  70                  75                  80
Thr Ser Gly Phe Gly Gly Met Ala Asn Val Ala Ile Ser Arg Glu Gln
                 85                  90                  95
Ala Ser Glu Leu Gln Thr Asn Leu Val Trp Phe Leu Lys Thr Gly Ala
            100                 105                 110
Gly Asn Lys Leu Pro Leu Ala Asp Val Arg Ala Ala Met Leu Leu Arg
            115                 120                 125
Ala Asn Ser His Met Arg Gly Ala Ser Gly Ile Arg Leu Glu Leu Ile
            130                 135                 140
Lys Arg Met Glu Ile Phe Leu Asn Ala Gly Val Thr Pro Tyr Val Tyr
145                 150                 155                 160
Glu Phe Gly Ser Ile Gly Ala Ser Gly Asp Leu Val Pro Leu Ser Tyr
                165                 170                 175
Ile Thr Gly Ser Leu Ile Gly Leu Asp Pro Ser Phe Lys Val Asp Phe
            180                 185                 190
Asn Gly Lys Glu Met Asp Ala Pro Thr Ala Leu Arg Gln Leu Asn Leu
            195                 200                 205
Ser Pro Leu Thr Leu Leu Pro Lys Glu Gly Leu Ala Met Met Asn Gly
            210                 215                 220
Thr Ser Val Met Thr Gly Ile Ala Ala Asn Cys Val Tyr Asp Thr Gln
225                 230                 235                 240
Ile Leu Thr Ala Ile Ala Met Gly Val His Ala Leu Asp Ile Gln Ala
                245                 250                 255
Leu Asn Gly Thr Asn Gln Ser Phe His Pro Phe Ile His Asn Ser Lys
            260                 265                 270
Pro His Pro Gly Gln Leu Trp Ala Ala Asp Gln Met Ile Ser Leu Leu
            275                 280                 285
Ala Asn Ser Gln Leu Val Arg Asp Glu Leu Asp Gly Lys His Asp Tyr
            290                 295                 300
Arg Asp His Glu Leu Ile Gln Asp Arg Tyr Ser Leu Arg Cys Leu Pro
305                 310                 315                 320
Gln Tyr Leu Gly Pro Ile Val Asp Gly Ile Ser Gln Ile Ala Lys Gln
                325                 330                 335
Ile Glu Ile Glu Ile Asn Ser Val Thr Asp Asn Pro Leu Ile Asp Val
            340                 345                 350
Asp Asn Gln Ala Ser Tyr His Gly Gly Asn Phe Leu Gly Gln Tyr Val
            355                 360                 365
Gly Met Gly Met Asp His Leu Arg Tyr Tyr Ile Gly Leu Leu Ala Lys
            370                 375                 380
His Leu Asp Val Gln Ile Ala Leu Leu Ala Ser Pro Glu Phe Ser Asn
385                 390                 395                 400
Gly Leu Pro Pro Ser Leu Leu Gly Asn Arg Glu Arg Lys Val Asn Met
                405                 410                 415
Gly Leu Lys Gly Leu Gln Ile Cys Gly Asn Ser Ile Met Pro Leu Leu
            420                 425                 430
Thr Phe Tyr Gly Asn Ser Ile Ala Asp Arg Phe Pro Thr His Ala Glu
            435                 440                 445
```

```
Gln Phe Asn Gln Asn Ile Asn Ser Gln Gly Tyr Thr Ser Ala Thr Leu
    450                 455                 460

Ala Arg Arg Ser Val Asp Ile Phe Gln Asn Tyr Val Ala Ile Ala Leu
465                 470                 475                 480

Met Phe Gly Val Gln Ala Val Asp Leu Arg Thr Tyr Lys Lys Thr Gly
                485                 490                 495

His Tyr Asp Ala Arg Ala Cys Leu Ser Pro Ala Thr Glu Arg Leu Tyr
            500                 505                 510

Ser Ala Val Arg His Val Val Gly Gln Lys Pro Thr Ser Asp Arg Pro
            515                 520                 525

Tyr Ile Trp Asn Asp Asn Glu Gln Gly Leu Asp Glu His Ile Ala Arg
            530                 535                 540

Ile Ser Ala Asp Ile Ala Ala Gly Gly Val Ile Val Gln Ala Val Gln
545                 550                 555                 560

Asp Ile Leu Pro Cys Leu His
                565

<210> SEQ ID NO 22
<211> LENGTH: 514
<212> TYPE: PRT
<213> ORGANISM: Photorhabdus luminescens

<400> SEQUENCE: 22

Met Lys Gln Leu Thr Ile Tyr Pro Gly Lys Leu Thr Leu Asp Glu Leu
1               5                   10                  15

Arg Gln Val Tyr Leu Gln Pro Val Lys Ile Thr Leu Asp Ser Gln Ile
            20                  25                  30

Phe Pro Ala Ile Glu Arg Ser Val Glu Cys Val Asn Ala Ile Leu Ala
        35                  40                  45

Glu Asn Arg Thr Ala Tyr Gly Ile Asn Thr Gly Phe Gly Leu Leu Ala
    50                  55                  60

Ser Thr Arg Ile Glu Glu Asp Asn Leu Glu Lys Leu Gln Arg Ser Leu
65                  70                  75                  80

Val Val Ser His Ala Ala Gly Val Gly Lys Ala Leu Asp Asp Asn Met
                85                  90                  95

Thr Arg Leu Ile Met Val Leu Lys Ile Asn Ser Leu Ser Arg Gly Tyr
            100                 105                 110

Ser Gly Ile Arg Leu Ala Val Ile Gln Ala Leu Ile Ala Leu Val Asn
        115                 120                 125

Ala Glu Ile Tyr Pro His Ile Pro Cys Lys Gly Ser Val Gly Ala Ser
    130                 135                 140

Gly Asp Leu Ala Pro Leu Ala His Met Ser Leu Leu Leu Leu Gly Glu
145                 150                 155                 160

Gly Gln Ala Arg Tyr Gln Gly Glu Trp Leu Pro Ala Lys Glu Ala Leu
                165                 170                 175

Ala Lys Ala Asn Leu Gln Pro Ile Thr Leu Ala Ala Lys Glu Gly Leu
            180                 185                 190

Ala Leu Leu Asn Gly Thr Gln Val Ser Thr Ala Phe Ala Leu Arg Gly
        195                 200                 205

Leu Phe Glu Ala Glu Asp Leu Leu Ala Ala Ile Val Cys Gly Ser
    210                 215                 220

Leu Ser Val Glu Ala Ala Leu Gly Ser Arg Lys Pro Phe Asp Ala Arg
225                 230                 235                 240

Val His Val Val Arg Gly Gln Gln Gly Gln Ile Asp Val Ala Ala Leu
```

```
            245                 250                 255
Tyr Arg His Val Leu Glu Glu Ser Ser Glu Leu Ser Asp Ser His Ile
            260                 265                 270

Asn Cys Pro Lys Val Gln Asp Pro Tyr Ser Leu Arg Cys Gln Pro Gln
        275                 280                 285

Val Met Gly Ala Cys Leu Thr Gln Leu Arg His Ala Ala Asp Val Ile
    290                 295                 300

Leu Thr Glu Ala Asn Ala Val Ser Asp Asn Pro Leu Val Phe Ala Glu
305                 310                 315                 320

Gln Gly Glu Val Ile Ser Gly Gly Asn Phe His Ala Glu Pro Val Ala
                325                 330                 335

Met Ala Ser Asp Asn Leu Ala Leu Val Leu Ala Glu Ile Gly Ala Leu
            340                 345                 350

Ser Glu Arg Arg Ile Ala Leu Leu Met Asp Ser His Met Ser Gln Leu
        355                 360                 365

Pro Pro Phe Leu Val Glu Asn Gly Gly Val Asn Ser Gly Phe Met Ile
    370                 375                 380

Ala Gln Val Thr Ala Ala Ala Leu Ala Ser Glu Asn Lys Ala Leu Ala
385                 390                 395                 400

His Pro Ala Ser Val Asp Ser Leu Pro Thr Ser Ala Asn Gln Glu Asp
                405                 410                 415

His Val Ser Met Ala Pro Ala Ala Gly Arg Arg Leu Trp Glu Met Ala
            420                 425                 430

Glu Asn Thr Arg Gly Ile Leu Ala Ile Glu Trp Leu Ser Ala Cys Gln
        435                 440                 445

Gly Ile Asp Phe Arg Asn Gly Leu Lys Ser Ser Pro Ile Leu Glu Glu
    450                 455                 460

Ala Arg Val Ile Leu Arg Ala Lys Val Asp Tyr Tyr Asp Gln Asp Arg
465                 470                 475                 480

Phe Phe Ala Pro Asp Ile Asp Ala Ala Val Lys Leu Leu Ala Glu Gln
                485                 490                 495

His Leu Ser Ser Leu Leu Pro Ser Gly Gln Ile Leu Gln Arg Lys Asn
            500                 505                 510

Asn Arg

<210> SEQ ID NO 23
<211> LENGTH: 471
<212> TYPE: PRT
<213> ORGANISM: Proteus mirabilis

<400> SEQUENCE: 23

Met Ala Ile Ser Arg Arg Lys Phe Ile Leu Gly Gly Thr Val Val Ala
1               5                   10                  15

Val Ala Ala Gly Ala Gly Val Leu Thr Pro Met Leu Thr Arg Glu Gly
            20                  25                  30

Arg Phe Val Pro Gly Thr Pro Arg His Gly Phe Val Glu Gly Thr Gly
        35                  40                  45

Gly Pro Leu Pro Lys Gln Asp Asp Val Val Ile Gly Ala Gly Ile
    50                  55                  60

Leu Gly Ile Met Thr Ala Ile Asn Leu Ala Glu Arg Gly Leu Ser Val
65                  70                  75                  80

Thr Ile Val Glu Lys Gly Asn Ile Ala Gly Glu Gln Ser Ser Arg Phe
                85                  90                  95

Tyr Gly Gln Ala Ile Ser Tyr Lys Met Pro Asp Glu Thr Phe Leu Leu
```

```
                    100                 105                 110
His His Leu Gly Lys His Arg Trp Arg Glu Met Asn Ala Lys Val Gly
            115                 120                 125

Ile Asp Thr Thr Tyr Arg Thr Gln Gly Arg Val Glu Val Pro Leu Asp
130                 135                 140

Glu Glu Asp Leu Glu Asn Val Arg Lys Trp Ile Asp Ala Lys Ser Lys
145                 150                 155                 160

Asp Val Gly Ser Asp Ile Pro Phe Arg Thr Lys Met Ile Glu Gly Ala
            165                 170                 175

Glu Leu Lys Gln Arg Leu Arg Gly Ala Thr Thr Asp Trp Lys Ile Ala
            180                 185                 190

Gly Phe Glu Glu Asp Ser Gly Ser Phe Asp Pro Glu Val Ala Thr Phe
            195                 200                 205

Val Met Ala Glu Tyr Ala Lys Lys Met Gly Ile Lys Ile Phe Thr Asn
            210                 215                 220

Cys Ala Ala Arg Gly Leu Glu Thr Gln Ala Gly Val Ile Ser Asp Val
225                 230                 235                 240

Val Thr Glu Lys Gly Pro Ile Lys Thr Ser Arg Val Val Ala Gly
            245                 250                 255

Gly Val Gly Ser Arg Leu Phe Met Gln Asn Leu Asn Val Asp Val Pro
            260                 265                 270

Thr Leu Pro Ala Tyr Gln Ser Gln Leu Ile Ser Ala Ala Pro Asn
            275                 280                 285

Ala Pro Gly Gly Asn Val Ala Leu Pro Gly Gly Ile Phe Phe Arg Asp
290                 295                 300

Gln Ala Asp Gly Thr Tyr Ala Thr Ser Pro Arg Val Ile Val Ala Pro
305                 310                 315                 320

Val Val Lys Glu Ser Phe Thr Tyr Gly Tyr Lys Tyr Leu Pro Leu Leu
            325                 330                 335

Ala Leu Pro Asp Phe Pro Val His Ile Ser Leu Asn Glu Gln Leu Ile
            340                 345                 350

Asn Ser Phe Met Gln Ser Thr His Trp Asp Leu Asn Glu Glu Ser Pro
            355                 360                 365

Phe Glu Lys Tyr Arg Asp Met Thr Ala Leu Pro Asp Leu Pro Glu Leu
            370                 375                 380

Asn Ala Ser Leu Glu Lys Leu Lys Lys Glu Phe Pro Ala Phe Lys Glu
385                 390                 395                 400

Ser Thr Leu Ile Asp Gln Trp Ser Gly Ala Met Ala Ile Ala Pro Asp
            405                 410                 415

Glu Asn Pro Ile Ile Ser Asp Val Lys Glu Tyr Pro Gly Leu Val Ile
            420                 425                 430

Asn Thr Ala Thr Gly Trp Gly Met Thr Glu Ser Pro Val Ser Ala Glu
            435                 440                 445

Ile Thr Ala Asp Leu Leu Leu Gly Lys Lys Pro Val Leu Asp Ala Lys
450                 455                 460

Pro Phe Ser Leu Tyr Arg Phe
465                 470

<210> SEQ ID NO 24
<211> LENGTH: 473
<212> TYPE: PRT
<213> ORGANISM: Proteus mirabilis

<400> SEQUENCE: 24
```

-continued

```
Met Asn Ile Ser Arg Arg Lys Leu Leu Leu Gly Val Gly Ala Ala Gly
1               5                   10                  15

Val Leu Ala Gly Gly Ala Ala Leu Val Pro Met Val Arg Arg Asp Gly
            20                  25                  30

Lys Phe Val Glu Ala Lys Ser Arg Ala Ser Phe Val Glu Gly Thr Gln
        35                  40                  45

Gly Ala Leu Pro Lys Glu Ala Asp Val Val Ile Ile Gly Ala Gly Ile
    50                  55                  60

Gln Gly Ile Met Thr Ala Ile Asn Leu Ala Glu Arg Gly Met Ser Val
65                  70                  75                  80

Thr Ile Leu Glu Lys Gly Gln Ile Ala Gly Glu Gln Ser Gly Arg Ala
                85                  90                  95

Tyr Ser Gln Ile Ile Ser Tyr Gln Thr Ser Pro Glu Ile Phe Pro Leu
            100                 105                 110

His His Tyr Gly Lys Ile Leu Trp Arg Gly Met Asn Glu Lys Ile Gly
        115                 120                 125

Ala Asp Thr Ser Tyr Arg Thr Gln Gly Arg Val Glu Ala Leu Ala Asp
    130                 135                 140

Glu Lys Ala Leu Asp Lys Ala Gln Ala Trp Ile Lys Thr Ala Lys Glu
145                 150                 155                 160

Ala Ala Gly Phe Asp Thr Pro Leu Asn Thr Arg Ile Ile Lys Gly Glu
                165                 170                 175

Glu Leu Ser Asn Arg Leu Val Gly Ala Gln Thr Pro Trp Thr Val Ala
            180                 185                 190

Ala Phe Glu Glu Asp Ser Gly Ser Val Asp Pro Glu Thr Gly Thr Pro
        195                 200                 205

Ala Leu Ala Arg Tyr Ala Lys Gln Ile Gly Val Lys Ile Tyr Thr Asn
    210                 215                 220

Cys Ala Val Arg Gly Ile Glu Thr Ala Gly Gly Lys Ile Ser Asp Val
225                 230                 235                 240

Val Ser Glu Lys Gly Ala Ile Lys Thr Ser Gln Val Val Leu Ala Gly
                245                 250                 255

Gly Ile Trp Ser Arg Leu Phe Met Gly Asn Met Gly Ile Asp Ile Pro
            260                 265                 270

Thr Leu Asn Val Tyr Leu Ser Gln Gln Arg Val Ser Gly Val Pro Gly
        275                 280                 285

Ala Pro Arg Gly Asn Val His Leu Pro Asn Gly Ile His Phe Arg Glu
    290                 295                 300

Gln Ala Asp Gly Thr Tyr Ala Val Ala Pro Arg Ile Phe Thr Ser Ser
305                 310                 315                 320

Ile Val Lys Asp Ser Phe Leu Leu Gly Pro Lys Phe Met His Leu Leu
                325                 330                 335

Gly Gly Gly Glu Leu Pro Leu Glu Phe Ser Ile Gly Glu Asp Leu Phe
            340                 345                 350

Asn Ser Phe Lys Met Pro Thr Ser Trp Asn Leu Asp Glu Lys Thr Pro
        355                 360                 365

Phe Glu Gln Phe Arg Val Ala Thr Ala Thr Gln Asn Thr Gln His Leu
    370                 375                 380

Asp Ala Val Phe Gln Arg Met Lys Thr Glu Phe Pro Val Phe Glu Lys
385                 390                 395                 400

Ser Glu Val Val Glu Arg Trp Gly Ala Val Ser Pro Thr Phe Asp
                405                 410                 415

Glu Leu Pro Ile Ile Ser Glu Val Lys Glu Tyr Pro Gly Leu Val Ile
```

```
                420              425              430
Asn Thr Ala Thr Val Trp Gly Met Thr Glu Gly Pro Ala Ala Gly Glu
            435              440              445

Val Thr Ala Asp Ile Val Met Gly Lys Lys Pro Val Ile Asp Pro Thr
450              455              460

Pro Phe Ser Leu Asp Arg Phe Lys Lys
465              470

<210> SEQ ID NO 25
<211> LENGTH: 471
<212> TYPE: PRT
<213> ORGANISM: Proteus vulgaris

<400> SEQUENCE: 25

Met Ala Ile Ser Arg Arg Lys Phe Ile Ile Gly Gly Thr Val Val Ala
1               5                   10                  15

Val Ala Ala Gly Ala Gly Ile Leu Thr Pro Met Leu Thr Arg Glu Gly
                20                  25                  30

Arg Phe Val Pro Gly Thr Pro Arg His Gly Phe Val Glu Gly Thr Glu
            35                  40                  45

Gly Ala Leu Pro Lys Gln Ala Asp Val Val Val Gly Ala Gly Ile
        50                  55                  60

Leu Gly Ile Met Thr Ala Ile Asn Leu Val Glu Arg Gly Leu Ser Val
65                  70                  75                  80

Val Ile Val Glu Lys Gly Asn Ile Ala Gly Glu Gln Ser Ser Arg Phe
                85                  90                  95

Tyr Gly Gln Ala Ile Ser Tyr Lys Met Pro Asp Glu Thr Phe Leu Leu
            100                 105                 110

His His Leu Gly Lys His Arg Trp Arg Glu Met Asn Ala Lys Val Gly
        115                 120                 125

Ile Asp Thr Thr Tyr Arg Thr Gln Gly Arg Val Glu Val Pro Leu Asp
130                 135                 140

Glu Glu Asp Leu Val Asn Val Arg Lys Trp Ile Asp Glu Arg Ser Lys
145                 150                 155                 160

Asn Val Gly Ser Asp Ile Pro Phe Lys Thr Arg Ile Ile Glu Gly Ala
                165                 170                 175

Glu Leu Asn Gln Arg Leu Arg Gly Ala Thr Thr Asp Trp Lys Ile Ala
            180                 185                 190

Gly Phe Glu Glu Asp Ser Gly Ser Phe Asp Pro Glu Val Ala Thr Phe
        195                 200                 205

Val Met Ala Glu Tyr Ala Lys Lys Met Gly Val Arg Ile Tyr Thr Gln
210                 215                 220

Cys Ala Ala Arg Gly Leu Glu Thr Gln Ala Gly Val Ile Ser Asp Val
225                 230                 235                 240

Val Thr Glu Lys Gly Ala Ile Lys Thr Ser Gln Val Val Ala Gly
                245                 250                 255

Gly Val Trp Ser Arg Leu Phe Met Gln Asn Leu Asn Val Asp Val Pro
            260                 265                 270

Thr Leu Pro Ala Tyr Gln Ser Gln Gln Leu Ile Ser Gly Ser Pro Thr
        275                 280                 285

Ala Pro Gly Gly Asn Val Ala Leu Pro Gly Gly Ile Phe Phe Arg Glu
        290                 295                 300

Gln Ala Asp Gly Thr Tyr Ala Thr Ser Pro Arg Val Ile Val Ala Pro
305                 310                 315                 320
```

```
Val Val Lys Glu Ser Phe Thr Tyr Gly Tyr Lys Tyr Leu Pro Leu Leu
            325                 330                 335

Ala Leu Pro Asp Phe Pro Val His Ile Ser Leu Asn Glu Gln Leu Ile
            340                 345                 350

Asn Ser Phe Met Gln Ser Thr His Trp Asn Leu Asp Glu Val Ser Pro
            355                 360                 365

Phe Glu Gln Phe Arg Asn Met Thr Ala Leu Pro Asp Leu Pro Glu Leu
            370                 375                 380

Asn Ala Ser Leu Glu Lys Leu Lys Ala Glu Phe Pro Ala Phe Lys Glu
385                 390                 395                 400

Ser Lys Leu Ile Asp Gln Trp Ser Gly Ala Met Ala Ile Ala Pro Asp
            405                 410                 415

Glu Asn Pro Ile Ile Ser Glu Val Lys Glu Tyr Pro Gly Leu Val Ile
            420                 425                 430

Asn Thr Ala Thr Gly Trp Gly Met Thr Glu Ser Pro Val Ser Ala Glu
            435                 440                 445

Leu Thr Ala Asp Leu Leu Gly Lys Lys Pro Val Leu Asp Pro Lys
            450                 455                 460

Pro Phe Ser Leu Tyr Arg Phe
465                 470

<210> SEQ ID NO 26
<211> LENGTH: 452
<212> TYPE: PRT
<213> ORGANISM: Homo sapiens

<400> SEQUENCE: 26

Met Ser Thr Ala Val Leu Glu Asn Pro Gly Leu Gly Arg Lys Leu Ser
1               5                   10                  15

Asp Phe Gly Gln Glu Thr Ser Tyr Ile Glu Asp Asn Cys Asn Gln Asn
            20                  25                  30

Gly Ala Ile Ser Leu Ile Phe Ser Leu Lys Glu Glu Val Gly Ala Leu
        35                  40                  45

Ala Lys Val Leu Arg Leu Phe Glu Glu Asn Asp Val Asn Leu Thr His
    50                  55                  60

Ile Glu Ser Arg Pro Ser Arg Leu Lys Lys Asp Glu Tyr Glu Phe Phe
65                  70                  75                  80

Thr His Leu Asp Lys Arg Ser Leu Pro Ala Leu Thr Asn Ile Ile Lys
                85                  90                  95

Ile Leu Arg His Asp Ile Gly Ala Thr Val His Glu Leu Ser Arg Asp
            100                 105                 110

Lys Lys Lys Asp Thr Val Pro Trp Phe Pro Arg Thr Ile Gln Glu Leu
        115                 120                 125

Asp Arg Phe Ala Asn Gln Ile Leu Ser Tyr Gly Ala Glu Leu Asp Ala
    130                 135                 140

Asp His Pro Gly Phe Lys Asp Pro Val Tyr Arg Ala Arg Arg Lys Gln
145                 150                 155                 160

Phe Ala Asp Ile Ala Tyr Asn Tyr Arg His Gly Gln Pro Ile Pro Arg
                165                 170                 175

Val Glu Tyr Met Glu Glu Gly Lys Lys Thr Trp Gly Thr Val Phe Lys
            180                 185                 190

Thr Leu Lys Ser Leu Tyr Lys Thr His Ala Cys Tyr Glu Tyr Asn His
        195                 200                 205

Ile Phe Pro Leu Leu Glu Lys Tyr Cys Gly Phe His Glu Asp Asn Ile
    210                 215                 220
```

-continued

```
Pro Gln Leu Glu Asp Val Ser Gln Phe Leu Gln Thr Cys Thr Gly Phe
225                 230                 235                 240

Arg Leu Arg Pro Val Ala Gly Leu Leu Ser Ser Arg Asp Phe Leu Gly
                245                 250                 255

Gly Leu Ala Phe Arg Val Phe His Cys Thr Gln Tyr Ile Arg His Gly
            260                 265                 270

Ser Lys Pro Met Tyr Thr Pro Glu Pro Asp Ile Cys His Glu Leu Leu
        275                 280                 285

Gly His Val Pro Leu Phe Ser Asp Arg Ser Phe Ala Gln Phe Ser Gln
    290                 295                 300

Glu Ile Gly Leu Ala Ser Leu Gly Ala Pro Asp Glu Tyr Ile Glu Lys
305                 310                 315                 320

Leu Ala Thr Ile Tyr Trp Phe Thr Val Glu Phe Gly Leu Cys Lys Gln
                325                 330                 335

Gly Asp Ser Ile Lys Ala Tyr Gly Ala Gly Leu Leu Ser Ser Phe Gly
            340                 345                 350

Glu Leu Gln Tyr Cys Leu Ser Glu Lys Pro Lys Leu Leu Pro Leu Glu
        355                 360                 365

Leu Glu Lys Thr Ala Ile Gln Asn Tyr Thr Val Thr Glu Phe Gln Pro
    370                 375                 380

Leu Tyr Tyr Val Ala Glu Ser Phe Asn Asp Ala Lys Glu Lys Val Arg
385                 390                 395                 400

Asn Phe Ala Ala Thr Ile Pro Arg Pro Phe Ser Val Arg Tyr Asp Pro
                405                 410                 415

Tyr Thr Gln Arg Ile Glu Val Leu Asp Asn Thr Gln Gln Leu Lys Ile
            420                 425                 430

Leu Ala Asp Ser Ile Asn Ser Glu Ile Gly Ile Leu Cys Ser Ala Leu
        435                 440                 445

Gln Lys Ile Lys
    450
```